US008273875B2

(12) United States Patent
Smith et al.

(10) Patent No.: US 8,273,875 B2
(45) Date of Patent: Sep. 25, 2012

(54) HIGH PERFORMANCE LUMINESCENT COMPOUNDS

(75) Inventors: Bradley Smith, Granger, IN (US); Arunkumar Easwaran, Media, PA (US)

(73) Assignees: University of Notre Dame du Lac, Notre Dame, IN (US); Molecular Targeting Technologies, Inc., West Chester, PA (US)

( * ) Notice: Subject to any disclaimer, the term of this patent is extended or adjusted under 35 U.S.C. 154(b) by 305 days.

(21) Appl. No.: 12/619,536

(22) Filed: Nov. 16, 2009

(65) Prior Publication Data
US 2011/0118459 A1    May 19, 2011

(51) Int. Cl.
C07D 245/04    (2006.01)
C07D 225/04    (2006.01)
(52) U.S. Cl. .................................... 540/460; 540/461
(58) Field of Classification Search ............................. None
See application file for complete search history.

(56) References Cited

FOREIGN PATENT DOCUMENTS

| WO | 0016810 | 3/2000 |
|---|---|---|
| WO | 0224816 A1 | 3/2002 |
| WO | 03074091 A2 | 9/2003 |
| WO | 2008 094637 A2 | 8/2008 |

OTHER PUBLICATIONS

Mujumdar, Swati R., et al., "Cyanine-Labeling Reagents: Sulfobenzindocyanine Succinimidyl Esters," Bioconjugate Chemistry, 1996, 7, pp. 356-362, American Chemical Society, 1155 Sixteenth Street NW, Washington, DC.
Gruber, Hermann J. et al., "Preparation of Thiol-Reactive Cy5 Derivatives from Commercial Cy5 Succinimidyl Ester," Bioconjugate Chemistry, 2000, 11, pp. 161-166, American Chemical Society, 1155 Sixteenth Street NW, Washington, DC.
Jose, Jiney et al., "Water-Soluble Nile Blue Derivatives: Syntheses and Photophysical Properties," Chemistry, A European Journal, 2008, Wiley-VCH Verlag GmbH & Co. KGaA, Weinheim, Germany.
Wu, Liangxing et al., "Syntheses of Highly Fluorescent GFP-Chromophore Analogues," Journal of the American.Chemistry Society, 2008, 130 (12), pp. 4089-4096, American Chemical Society, 1155 Sixteenth Street NW, Washington, DC.
Niu, Song Lin et al., "Water-Soluble BODIPY Derivatives," Organic Letters, Apr. 2009, American Chemical Society, 1155 Sixteenth Street NW, Washington, DC.
Ho, Nan-hui et al., "Development of Water-Soluble Far-Red Flurogenic Dyes for Enzyme Sensing," Science Direct, Tetrahedron, 2006, 62, pp. 578-585, Elsevier Ltd., Amsterdam, The Netherlands.
Romieu, Anthony et al., "Postsynthetic Derivatization of Fluorophores with alpha-Sulfo-beta-alanine Dipeptide Linker Application to the Preparation of Water-Soluble Cyanine and Rhodamine Dyes," Bioconjugate Chemistry, 2008, 19, pp. 279-289, American Chemical Society, 1155 Sixteenth Street NW, Washington, DC.
Marme, Nicole et al., "Inter- and Intramolecular Fluorescence Quenching of Organic Dyes by Tryptophan," Bioconjugate Chemistry, 2003, 14, pp. 1133-1139, American Chemical Society, 1155 Sixteenth Street NW, Washington, DC.
Bouteiller, Cedric et al., "Novel Water-Soluble Near-Infrared Cyanine Dyes: Synthesis, Spectral Properties, and Use in the Preparation of Internally Quenched Fluorescent Probes," Bioconjugate Chemistry, 2007, 18, pp. 1303-1317, American Chemical Society, 1155 Sixteenth Street NW, Washington, DC.
Ryu, Eui-Hyun et al., "Efficient Synthesis of Water-Soluble Calixarenes Using Click Chemistry," Organic Letters, 2005, vol. 7, pp. 1035-1037, American Chemical Society, 1155 Sixteenth Street NW, Washington, DC.
Ornelas, Catia et al., "Sulphonated "Click" Dendrimer-Stabilized Palladium Nanoparticles as Highly Efficient Catalysts for Olefin Hydrogenation and Suzuki Coupling Reactions Under Ambient Conditions in Aqueous Media," Advanced Synthesis Catalysis, 2008, 350, pp. 837-845, Wiley-VCH Verlag GmbH & Co. KGaA, Weinheim, Germany.
Sousa-Herves, Ana et al., "Synthesis and Supramolecular Assembly of Clicked Anionic Dendritic Polymers Into Polyion Complex Micelles," Chemical Communications, 2008, pp. 3136-3138, The Royal Society of Chemistry, London, England.
Sreejith, Sivaramapanicker et al., "Squaraine Dyes: a Mine of Molecular Materials," Journal of Materials Chemistry, 2008, 18, pp. 264-274, The Royal Society of Chemistry, London, England.
Ajayaghosh, Ayyappanpillai, "Chemistry of Squaraine-Derived Materials: Near-IR Dyes, Low Band Gap Systems, and Cation Sensors," Accounts of Chemical Research, Apr. 8, 2005, pp. 449-459, vol. 38, No. 6, American Chemical Society, 1155 Sixteenth Street NW, Washington, DC.
Halton, Brian, "From Small Rings to Big Things: Xerography, Sensors, and the Squaraines," Chemistry in New Zealand, Apr. 2008, pp. 57-59, 62, New Zealand Institute of Chemistry, Christchurch, New Zealand.
Vadakkancheril, S. Jisha et al., "Site-Selective Binding and Dual Mode Recognition of Serum Albumin by a Squaraine Dye," Journal of American Chemistry Society, 2006, 128, pp. 6024-6025, American Chemical Society, 1155 Sixteenth Street NW, Washington, DC.
Suzuki, Yoshio, et al., "A Protein-Responsive Chromophore Based on Squaraine and Its Application to Visual Protein Detection on a Gel for SDS-PAGE," Angewandte Chemie Int. Ed., 2007, 46, pp. 4097-4099, Wiley-VCH Verlag GmbH & Co. KGaA, Weinheim, Germany.
Pham, Wellington et al., "An Azulene Dimer as a Near-Infrared Quencher," Angewandte Chemie Int. Ed., 2002, pp. 3659-3662, vol. 41, No. 19, Wiley-VCH Verlag GmbH & Co. KGaA, Weinheim, Germany.
Volkova, Kateryna D. et al., "Spectroscopic Study of Squaraines as Protein-Sensitive Fluorescent Dyes," Dyes and Pigments, 2007, 72, pp. 285-292, Elsevier Ltd., Amsterdam, The Netherlands. Thomas, Joseph et al., "Synthesis and Biosensor Performance of a Near-IR Thiol-Reactive Fluorophore Based on Benzothiazolium Squarine," Bioconjugate Chemistry, 2007, 18, pp. 1841-1846, American Chemical Society, 1155 Sixteenth Street NW, Washington, DC.
Ioffe, Valeriya M. et al., "A New Fluorescent Squaraine Probe for the Measurement of Membrane Polarity," Journal of Fluorescence, Jan. 2006, pp. 47-52, Vol. 16, No. 1, Springer Science+Business Media, Inc., Berlin, Germany.

(Continued)

Primary Examiner — Noble Jarrell
(74) Attorney, Agent, or Firm — Schwabe, Williamson & Wyatt

(57) ABSTRACT

Embodiments relate to the field of chemistry and biochemistry, and, more specifically, to novel near-infrared dyes that are photostable and resistant to quenching. The dyes belong to a novel family of squaraine rotaxanes, and they are particularly well-suited for use in biological applications. Also disclosed are methods of synthesizing the dyes and methods of using the dyes.

19 Claims, 20 Drawing Sheets

OTHER PUBLICATIONS

Ohira, Shino et al., "Electronic and Vibronic Contributions to Two-Photon Absorption in Donor-Acceptor-Donor Squaraine Chromophores," Chemistry, a European Journal, 2008, pp. 1-11, Wiley-VCH Verlag GmbH & Co. KGaA, Weinheim, Germany.

Climent, Estela et al., "Selective Chromofluorogenic Sensing of Heparin by using Functionalised Silica Nanoparticles Containing Binding Sites and a Signalling Reporter," Chemistry, a European Journal, 2009, 15, pp. 1816-1820, Wiley-VCH Verlag GmbH & Co. KGaA, Weinheim, Germany.

Eldo, J. et al., "New Low Band Gap Polymers: Control of Optical and Electronic Properties in near Infrared Absorbing Pi-Congugated Polysquaraines," Chemistry of Materials, 2002, 14(1), pp. 410-418, American Chemical Society, 1155 Sixteenth Street NW, Washington DC 20036.

Alex, Saji et al., "Dye Sensitization of Nanocrystalline TiO2: Enhanced Efficiency of Unsymmetrical Versus Symmetrical Squaraine Dyes," Journal of Photochemistry and Photobiology A:Chemistry, 172 (2005) pp. 63-71, Elsevier Ltd., Amsterdam, The Netherlands.

Bello, K.A. et al., Near-Infrared Absorbing Squarylium Dyes:, Dyes and Pigments, 1996, vol. 31, No. 2, pp. 79-87, Elsevier Ltd., Amsterdam, The Netherlands.

Arunkumar, Easwaran et al., "Selective Calcium Ion Sensing with a Bichromophoric Squaraine Foldamer," Journal of American Chemistry Society, 2005, 127, pp. 3156-3164, American Chemical Society, 1155 Sixteenth Street NW, Washington, DC.

Ros-Lis, Jose V. et al., "Squaraines as Reporter Units: Insights into their Photophysics, Protonation, and Metal-Ion Coordination Behaviour," Chemistry, a European Journal, 2008, Wiley-VCH Verlag GmbH & Co. KGaA, Weinheim, Germany.

Basheer, M.C. et al., "Design and Synthesis of Squaraine Based Near Infrared Fluorescent Probes," Science Direct, Tetrahedron 63 (2007, pp. 1617-1623, Elsevier Ltd., Amsterdam, The Netherlands.

Ramaiah, Danaboyina et al., "Halogenated Squaraine Dyes as Potential Photochemotherapeutic Agents. Synthesis and Study of Photophysical Properties and Quantum Efficiencies of Singlet Oxygen Generation," Photochemistry and Photobiology, 1997, 65(5); pp. 783-790, American Society for Photobiology, P.O. Box 7065, Lawrence, KS 66044.

Ramaiah, Danaboyina et al., "Squaraine Dyes for Photodynamic Therapy: Study of Their Cytotoxicity and Genotoxicity in Bacteria and Mammalian Cells," Photochemistry and Photobiology, 2002, 76(6); pp. 672-677, American Society for Photobiology, P.O. Box 7065, Lawrence, KS 66044.

Arunkumar, Easwaran et al., "Singlet Oxygen Generation Using Iodinated Squaraine and Squaraine-Rotaxane Dyes," New Journal of Chemistry, 2007, 31, pp. 677-683, The Royal Society of Chemistry, London, England.

Ros-Lis, Jose V. et al., "Squaraines as Fluro-Chromogenic Probes for Thiol-Containing Compounds and Their Application to the Detection of Biorelevant Thiols," Journal of American Chemistry Society, 2004, 126, pp. 4064-4065, American Chemical Society, 1155 Sixteenth Street NW, Washington, DC.

Sreejith, Sivaramapanicker et al., "A Near-Infrared Squaraine Dye as a Latent Ratiometric Flurophore for the Detection of Aminothiol Content in Blood Plasma," Angewandte Chemie Int. Ed., 2008, 47, pp. 7883-7887, Wiley-VCH Verlag GmbH & Co. KGaA, Weinheim, Germany.

Ros-Lis, Jose V. et al., "A Selective Chromogenic Reagent for Cyanide Determenation," ChemComm, 2002, pp. 2248-2249, The Royal Society of Chemistry, London, England.

Chen, Huijuan et al., "Aggregation of Surfactant Squaraine Dyes in Aqueous Solution and Microheterogeneous Media: Correlation of Aggregation Behavior with Molecular Structure," Journal of American Chemistry Society, 1996, 118, pp. 2584-2594, American Chemical Society, 1155 Sixteenth Street NW, Washington, DC.

Chen, Huijuan et al., "Aggregation of a Surfactant Squaraine in Langmuir-Blodgett Films, Solids, and Solution," Journal of Physical Chemistry, 1994, 98, pp. 5138-5146, American Chemical Society, 1155 Sixteenth Street NW, Washington, DC.

Das, Suresh et al., "Aggregation Behavior of Water Soluble Bis(benzothiazolylidene)squaraine Derivatives in Aqueous Media," Journal of Physical Chemistry, 1996, 100, pp. 17310-17315, American Chemical Society, 1155 Sixteenth Street NW, Washington, DC.

Das, Suresh et al., Photochemistry of Squaraine Dyes. 5. Aggregation of Bis(2,4-dihydroxyphenyl)squaraine and Bis (2,4,6-trihydroxyphenyl)squaraine and Their Photodissociation in Acetonitrile Solutions, Journal of Physical Chemistry, 1993, 97, pp. 13620-13624, American Chemical Society, 1155 Sixteenth Street NW, Washington, DC.

Arun, Kalliat T. et al., "Aggregation Behavior of Halogenated Squaraine Dyes in Buffer, Electrolytes, Organized Media and DNA," Journal of Physical Chemistry B, 2002, 106, pp. 11622-11627, American Chemical Society, 1155 Sixteenth Street NW, Washington, DC.

Arunkumar, Easwaran et al., "Squaraine-Derived Rotaxanes: Sterically Protected Fluorescent Near-IR Dyes," Journal of American Chemistry Society, 2005, 127, pp. 3288-3289, American Chemical Society, 1155 Sixteenth Street NW, Washington, DC.

Arunkumar, Easwaran et al., "Squaraine-Derived Rotaxanes: Highly Stable, Fluorescent Near-IR Dyes," Chemistry, A European Journal, 2006, 12, pp. 4684-4690, Wiley-VCH Verlag GmbH & Co. KGaA, Weinheim, Germany.

Johnson, James R. et al., "Squaraine Rotaxanes: Superior Substitutes for Cy-5 in Molecular Probes for Near-Infrared Fluorescence Cell Imaging," Angewandte Chemie Int. Ed., 2007, 46, pp. 5528-5531, Wiley-VCH Verlag GmbH & Co. KGaA, Weinheim, Germany.

Fu, Na et al., "Synthesis of New Generation Near-IR Fluorescent Squaraine-Rotaxanes," 232nd ACS National.Meeting, Sep. 10-14, 2006, San Francisco, CA, American Chemical Society, 1155 Sixteenth Street NW, Washington, DC.

Gassensmith, Jeremiah J., "Mix and Play Squaraine-Rotaxanes," 234th ACS National Meeting, Aug. 19-23, 2007, Boston, MA, American Chemical Society, 1155 Sixteenth Street NW, Washington, DC.

Smith, Bradley D., "Squaraine-Rotaxanes as Novel Fluorescent Bioimaging Probes," 234th ACS National Meeting, Aug. 19-23, 2007, Boston, MA, American Chemical Society, 1155 Sixteenth Street NW, Washington, DC.

Smith, Bradley D., "Squaraine-Rotaxanes as Fluorescent Imaging Probes for Cells and Whole Animals," 236th ACS National Meeting, Aug. 17-21, 2008, Philadelphia, PA, American Chemical Society, 1155 Sixteenth Street NW, Washington, DC.

Fu, Na, "Modification of Fluorescent Squaraine Rotaxane Structure," 237th ACS National Meeting, Mar. 22-26, 2009, Salt Lake City, UT, American Chemical Society, 1155 Sixteenth Street NW, Washington, DC.

Fu, Na et al., "Effect of Stopper Size on Squaraine Rotaxane Stability," Supramolecular Chemistry, Jan. 1, 2009, 21:1, pp. 118-124, Taylor & Francis, Mortimer House, 37-41 Mortimer Street, London W1T 3JH, UK.

Fu, Na et al., "Squaraine Rotaxanes with Boat Conformation Macrocycles," Journal of Organic Chemistry, 2009, 74, pp. 6462-6468, American Chemical Society, 1155 Sixteenth Street NW, Washington, DC.

Baumes, Jeffrey M. et al., "Using Mechanical Bond Strain to Control Chemical Reactivitity," 238th ACS National Meeting, Aug. 16-20, 2009, Washington, DC, American Chemical Society, 1155 Sixteenth Street NW, Washington, DC.

Gassensmith, Jeremiah J. et al., "Discovery and Early Development of Squaraine Rotaxanes," Chemical Communications, 2009, The Royal Society of Chemistry, London, England.

Xue, Min et al., "Triptycene-based Tetralactam Macrocycles: Synthesis, Structure and Complexation with Squaraine," Chemical Communications, 2008, pp. 6128-6130, The Royal Society of Chemistry, London, England.

Hsueh, Sheng-Yao et al., "Protecting a Squaraine Near-IR Dye Through its Incorporation in a Slippage-Derived [2].Rotaxane," Organic Letters, 2007, vol. 9, No. 22, pp. 4523-4526, American Chemical Society, 1155 Sixteenth Street NW, Washington, DC.

Oswald, Bernhard et al., "Red Laser-Induced Fluorescence Energy Transfer in an Immunosystem," Analytical Biochemistry, 2000, 280, pp. 272-277, Academic Press, Elsevier Ltd., Amsterdam, The Netherlands.

Tatarets, Anatoliy L., et al., "Synthesis of Water-Soluble, Ring-Substituted Squaraine Dyes and their Evaluation as Fluorescent Probes and Labels," Analytica Chimica Acta, 2006, 570, pp. 214-223, Elsevier Ltd., Amsterdam, The Netherlands.

Oswald, Bernhard et al., "Synthesis, Spectral Properties, and Detection Limits of Reactive Squaraine Dyes, a New Class of Diode Laser Compatible Fluorescent Protein Labels," Bioconjugate Chemistry, 1999, 10, pp. 925-931, American Chemical Society, 1155 Sixteenth Street NW, Washington, DC.

Reddington, Mark V., "Synthesis and Properties of Phosphonic Acid Containing Cyanine and Squaraine Dyes for Use as Fluorescent Labels," Bioconjugate Chemistry, 2007, 18, pp. 2178-2190, American Chemical Society, 1155 Sixteenth Street NW, Washington, DC.

Umezawa, Keitaro et al., "Water-soluble NIR Fluorescent Probes Based on Squaraine and Their Application for Protein Labeling," Analytical Sciences, Feb. 2008, vol. 24, pp. 213-217, The Japan Society for Analytical Chemistry, 1-26-2 Nishigotanda, Shinagawa, Tokyo, 141-0031 Japan.

Patsenker, Leonid et al., "Fluorescent Probes and Labels for Biomedical Applications," Ann. NY Academy of Sciences, 2008, 1130, pp. 179-187, New York Academy of Sciences, 250 Greenwich Street, New York, NY 10007-2157.

Toutchkine, Alexei et al., "Facile Synthesis of Thiol-Reactive Cy3 and Cy5 Derivatives with Enhanced Water Solubility," Bioconjugate Chemistry, 2002, vol. 13, No. 3, pp. 387-391, American Chemical Society, 1155 Sixteenth Street NW, Washington, DC.

Toutchkine, Alexei et al., "Simple One-Pot Preparation of Water-Soluble, Cysteine-Reactive Cyanine and Merocyanine Dyes for Biological Imaging," Bioconjugate Chemistry, 2007, 18, pp. 1344-1348, American Chemical Society, 1155 Sixteenth Street NW, Washington, DC.

Gassensmith, Jeremiah et al., "Self-Assembly of Fluorescent Inclusion Complexes in Competitive Media Including the Interior of Living Cells," Journal of American Chemical Society, 2007, vol. 129, pp. 15054-15059, American Chemical Society, 1155 Sixteenth Street NW, Washington, DC.

Smith, Bradley et al., "Squaraine-Derived Rotaxanes: Highly Stable, Fluorescent Near-IR Dyes," Chemistry, A European Journal, 2006, vol. 12, pp. 4684-4690, Wiley-VCH Verlag GmbH & Co., KGaA, Weinheim, Germany.

Gassensmith, Jeremiah J. et al., Synthesis and Photophysical Investigation of Squaraine Rotaxanes by "Clicked Capping," Organic Letters, 2008, vol. 10, No. 15, pp. 3343-3346, American Chemical Society, 1155 Sixteenth Street NW, Washington, DC.

Figure 7 (cont.)

| ND 0040 | |
|---|---|
| ND 0041 | |

Figure 7 (cont.)

| ND 0044 | |
| ND 0045 | |

HIGH PERFORMANCE LUMINESCENT COMPOUNDS

GOVERNMENT INTERESTS

This invention was made with Government support under Grants GM059078 and EB009266 awarded by the National Institutes of Health. The Government has certain rights in the invention.

TECHNICAL FIELD

Embodiments herein relate to the field of chemistry, and, more specifically, to novel luminescent compounds, synthesis thereof, and methods of using same.

BACKGROUND

Squaraine dyes are organic dyes with very intense fluorescence spectra, typically in the red and near infrared region, which makes them attractive for biological applications. They are characterized by an aromatic four-membered ring system derived from squaric acid.

Some squaraine dyes may be conjugated to biomolecules through a free carboxylic acid group. However, these lipophilic squaraine dyes suffer from three problems in physiological solutions: poor solubility, massive aggregation-induced loss of fluorescence signal, and poor stability. Even sulfonated squaraine derivatives that are water-soluble are still unstable in PBS.

Most squaraines are encumbered by nucleophilic attack of the central four-membered ring, which is highly electron deficient. This encumbrance may be attenuated by trapping the squaraine inside a macrocycle to form a permanently interlocked molecule called a squaraine rotaxane. Formation of a rotaxane around the dye helps to protect it from nucleophiles, which improves the stability of squaraine dyes in physiological solutions like phosphate buffered saline (PBS). However, squaraine rotaxanes still lose fluorescence signal under very strong aggregation conditions such as phosphate buffered saline, which limits their usefulness in biological applications.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

DETAILED DESCRIPTION OF DISCLOSED EMBODIMENTS

Figure 1:
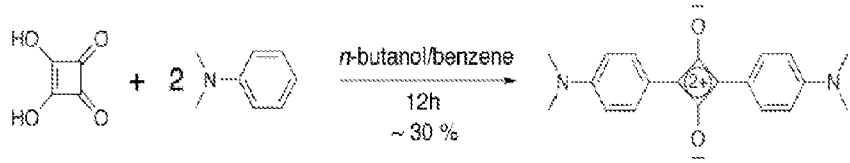
FIG. 1 illustrates the synthesis of symmetric and unsymmetric squaraine dyes, according to various embodiments.
Figure 1:
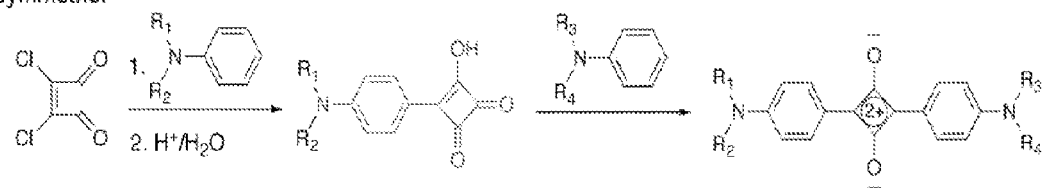

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

As used herein, the term "halogen" refers to fluoro, bromo, chloro and iodo substituents.

As used herein, the term "alkyl" refers to a cyclic, branched, or straight chain alkyl group containing only carbon and hydrogen, and unless otherwise mentioned contains one to twelve carbon atoms. This term may be further exemplified by groups such as methyl, ethyl, n-propyl, isopropyl, isobutyl, t-butyl, pentyl, hexyl, heptyl, adamantyl, and cyclopentyl. Alkyl groups may either be unsubstituted or substituted with one or more substituents, for instance, halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality.

As used herein, the term "substituted alkyl" refers to an alkyl moiety including 1-4 substituents selected from halogen, het, cycloalkyl, cycloalkenyl, aryl, amino, cyano, nitro, $-OQ_{10}$, $-S(O)_2Q_{10}$, $-S(O)Q_{10}$, $-OS(O)_2Q_{10}$, $-C(=NQ_{10})Q_{10}$, $-C(=NOQ_{10})Q_{10}$, $-S(O)_2-N=S(O)(Q_{10})_2$, $-S(O)_2-N=S(Q_{10})_2$, $-NQ_{10}Q_{10}$, $-C(O)Q_{10}$, $-C(S)Q_{10}$, $-C(O)OQ_{10}$, $-OC(O)Q_{10}$, $-C(O)NQ_{10}Q_{10}$, $-C(S)NQ_{10}Q_{10}$, $-N(Q_{10})C(S)NQ_{10}Q_{10}$, $-C(O)NQ_{10}Q_{10}$, $-C(S)NQ_{10}Q_{10}$, $-C(O)C(Q_{16})_2OC(O)Q_{10}$, $-CN$, $=S$, $-NQ_{10}C(O)Q_{10}$, $-NQ_{10}C(O)NQ_{10}Q_{10}$, $-S(O)_2NQ_{10}Q_{10}$, $-NQ_{10}S(O)_2Q_{10}$, $-NQ_{10}S(O)Q_{10}$, $-NQ_{10}SQ_{10}$, and $-SNQ_{10}Q_{10}$. Each of the het, cycloalkyl, cycloalkenyl, and aryl being optionally substituted with 1-4 substituents independently selected from halogen and $Q_{15}$.

As used herein, the term "cycloalkyl" refers to a cyclic alkyl moiety. Unless otherwise stated, cycloalkyl moieties include between 3 and 8 carbon atoms.

Each $Q_{10}$ is independently selected from H, alkyl, cycloalkyl, het, cycloalkenyl, and aryl. The het, cycloalkyl, cycloalkenyl, and aryl being optionally substituted with 1-3 substitutents selected from halo and $Q_{13}$.

Each $Q_{11}$ is independently selected from H, halogen, alkyl, aryl, cycloalkyl, and het. The alkyl, aryl, cycloalkyl, and het being optionally substituted with 1-3 substituents independently selected from halogen, nitro, cyano, =S, =O, and $Q_{14}$.

Each $Q_{13}$ is independently selected from $Q_{11}$, —$OQ_{11}$, —$SQ_{11}$, —$S(O)_2Q_{11}$, —$S(O)Q_{ii}$, —$OS(O)_2Q_{11}$, —$C(=NQ_{11})Q_{11}$, —$S(O)_2$—N=$S(O)(Q_{11})_2$, —$S(O)_2$—N=$S(Q_{11})_2$, —$SC(O)Q_{11}$, —$C(O)Q_{11}$, —$C(S)Q_{11}$, —$C(O)OQ_{11}$, —$OC(O)Q_{11}$, —$C(O)NQ_{11}Q_{11}$, —$(S)NQ_{11}Q_{11}$, —$C(O)C(Q_{16})_2OC(O)Q_{10}$, —CN, =O, =S, —$NQ_{11}C(O)Q_{11}$, —$NQ_{11}C(S)Q_{11}$, —$NQ_{11}C(O)NQ_{11}Q_{11}$, —$NQ_{11}C(S)NQ_{11}Q_{11}$, —$S(O)_2NQ_{11}Q_{11}$, —$NQ_{11}S(O)_2Q_{11}$, —$NQ_{11}S(O)Q_{11}$, —$NQ_{11}SQ_{11}$, —$NO_2$, and —$SNQ_{11}Q_{11}$.

Each $Q_{14}$ is independently selected from H, alkyl, cycloalkyl, phenyl, or naphthyl, each optionally substituted with 1-4 substituents independently selected from F, Cl, Br, I, —$OQ_{16}$, —$SQ_{16}$, —$S(O)_2Q_{16}$, —$S(O)Q_{16}$, —$OS(O)_2Q_{16}$, —$C(O)Q_{16}$, —$C(S)Q_{16}$, —$C(O)OQ_{16}$, —$NO_2$, —$C(O)NQ_{16}Q_{16}$, —$C(S)NQ_{16}Q_{16}$, —CN, —$NQ_{16}C(O)Q_{16}$, —$NQ_{16}C(S)Q_{16}$, —$NQ_{16}C(O)NQ_{16}Q_{16}$, —$NQ_{16}C(S)NQ_{16}Q_{16}$, —$S(O)_2NQ_{16}Q_{16}$, and —$NQ_{16}S(O)_2Q_{16}$. The alkyl, cycloalkyl, and cycloalkenyl being further optionally substituted with =O or =S.

Each $Q_{15}$ is independently selected from H, alkyl, cycloalkyl, heteroaryl, phenyl, or naphthyl, each optionally substituted with 1-4 substituents independently selected from F, Cl, Br, I, —$OQ_{16}$, —$SQ_{16}$, —$S(O)_2Q_{16}$, —$S(O)Q_{16}$, —$OS(O)_2Q_{16}$, —$C(=NQ_{16})Q_{16}$, —$S(O)_2$—N=$S(O)(Q_{16})_2$, —$S(O)_2$—N=$S(Q_{16})_2$, —$SC(O)Q_{16}$, —$C(O)Q_{16}$, —$C(S)Q_{16}$, —$C(O)OQ_{16}$, —$OC(O)Q_{16}$, —$C(S)NQ_{16}Q_{16}$, —$C(O)C(Q_{16})_2OC(O)Q_{16}$, —CN, —$NQ_{16}C(O)Q_{16}$, —$NQ_{16}C(S)Q_{16}$, —$NQ_{16}C(O)NQ_{16}Q_{16}$, —$NQ_{16}C(S)NQ_{16}Q_{16}$, —$S(O)_2NQ_{16}Q_{16}$, —$NQ_{16}S(O)_2Q_{16}$, —$NQ_{16}S(O)Q_{16}$, —$NQ_{16}SQ_{16}$, —$NO_2$, and —$SNQ_{16}Q_{16}$. The alkyl, cycloalkyl, and cycloalkenyl being further optionally substituted with =O or =S.

Each $Q_{16}$ is independently selected from H, alkyl, and cycloalkyl. The alkyl and cycloalkyl optionally including 1-3 halogens.

As used herein, the term "sulfone" refers to a chemical compound containing a sulfonyl functional group attached to two carbon atoms. The central sulfur atom is twice double bonded to oxygen and has two further hydrocarbon substituents. The general structural formula is R—S(=O)(=O)—R' where R and R' are the organic groups.

As used herein, the term "aryl" refers to phenyl and naphthyl.

As used herein, the term "heteroaryl" refers to a mono- or bicyclic het in which one or more cyclic ring is aromatic.

As used herein, the term "substituted heteroaryl" refers to a heteroaryl moiety substituted with one or more functional groups selected from halogen, alkyl, hydroxyl, amino, alkoxy, cyano, and nitro.

As used herein, the term "triazole" refers to either one of a pair of isomeric chemical compounds with molecular formula $C_2H_3N_3$, having a five-member ring of two carbon atoms and three nitrogen atoms.

As used herein, the term "sulfonate" refers to an anion with the general formula $RSO_2O$—. Sulfonates are the conjugate bases of sulfonic acids with formula $RSO_2OH$.

As used herein, the term "phosphonate" refers to organic compounds containing C—$PO(OH)_2$ or C—$PO(OR)_2$ groups (where R=alkyl or aryl).

As used herein, the term "succinimide" refers to a cyclic imide with the formula $C_4H_5NO_2$.

As used herein, the term "maleimide" refers to, the chemical compound with the formula $H_2C_2(CO)_2NH$.

As used herein, the term "polyethylene glycol" refers to a chemical compound composed of one or more ethoxy units (—$OCH_2CH_2$—) in a repeating linear series. The series may begin or end with a hydroxyl group (—OH groups) or other functionality.

As used herein, the term "biotin" refers to a water-soluble B-complex vitamin which is composed of an ureido (tetrahydroimidizalone) ring fused with a tetrahydrothiophene ring. A valeric acid substituent is attached to one of the carbon atoms of the tetrahydrothiophene ring.

As used herein, the term "dimethylammonium" refers to organic compounds that have four carbons, two of them methyl carbons, attached to a nitrogen atom that has a formal positive charge. Depending on the rest of the molecule there may or may not be a counter anion. It is also understood that in some embodiments the methyl groups may be substituted with longer chain alkyl groups.

As used herein, the term "zwitterionic group" refers to a group that has both a positive charge and a negative charge when the molecule is in an environment that is close to neutral pH. A molecule may have several attached "zwitterionic groups" Embodiments of the present disclosure provide a new family of squaraine rotaxane dyes that solve all major problems that known squaraine rotaxanes exhibit in physiological solutions, including: poor solubility, aggregation-induced loss of fluorescence signal, poor stability, only moderate brightness, poor biodistribution in animals, or bioconjugates with greatly altered charge patterns. The novel squaraine rotaxane dyes have photophysical properties that are very similar to the commonly used Cy-5 fluorophore, however, the new dyes are substantially more photostable and they resist quenching. This makes them superior substitutes for Cy-5 in many biotechnological and imaging applications. In some embodiments, the dyes may be conjugated to small and large biological molecules to make fluorescent molecular probes for various imaging applications.

In some embodiments, the squaraine rotaxanes may include one or more sulfonate or phosphonate groups and also may include one or more reactive sites for bioconjugation. In other embodiments, the squaraine rotaxanes may be uncharged or nearly uncharged overall, but may include one or more zwitterionic groups for water solubility and also may include one or more reactive sites for bioconjugation. Embodiments of the present disclosure encompass any racemic, optically-active, polymorphic, tautomeric, or stereoisomeric form or mixture thereof, of a compound of the disclosure that possesses the useful properties described herein. Other embodiments include bioconjugates of the squaraine rotaxane dyes disclosed herein. Still other embodiments provide methods of synthesizing the squaraine rotaxane compounds described herein.

In embodiments, squaraine rotaxanes are made in three major steps; (1) fabrication of the central squaraine thread component, (2) encapsulation of this thread component inside a macrocycle to make a rotaxane, and (3) covalent modification of the rotaxane. As described herein, sulfonate, phosphonate, or zwitterionic groups are added after the second step since their presence diminishes the synthetic yields in the second step. Reactions that directly attach sulfonate groups via electrophilic addition mechanisms do not produce high yields of products. Embodiments disclose herein a much better approach for attaching a sulfonate or a phosphate group or a zwitterionic group to the squaraine rotaxane.

In some embodiments, attaching a sulfonate, phosphonate, or zwitterionic group to the squaraine rotaxane via amide bond formation is undesirable for bioimaging probes because amide bonds may be broken by enzymatic action. Preferred embodiments involve the conjugation method of forming triazole linkages using a copper catalyzed azide/alkyne cycloaddition reaction. In embodiments, triazoles are excellent linkages because they are resistant to protease enzyme cleavage and their formation does not produce by-products.

In an embodiment, a squaraine rotaxane may have at least one sulfonate/phosphonate group and/or at least one zwitterionic group, and may have the formula:

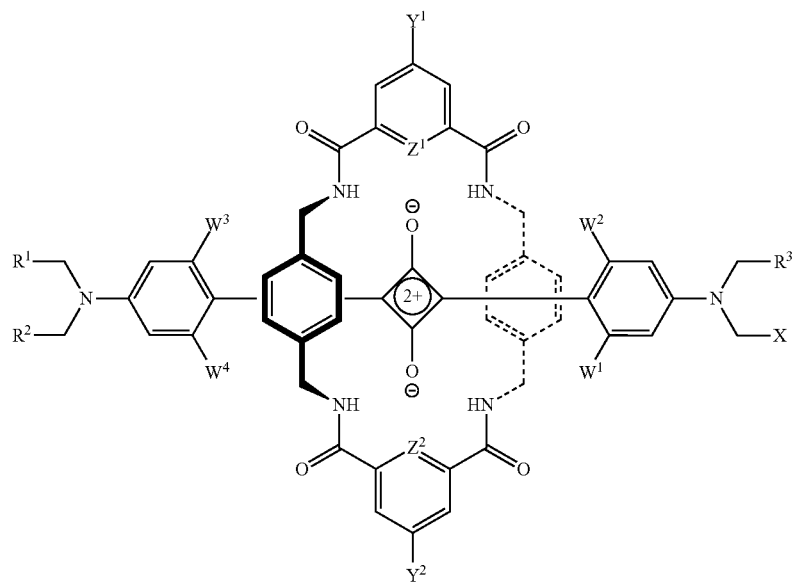

or a pharmaceutically acceptable salt thereof, wherein: $R^1$, $R^2$, and $R^3$ are each independently alkyl, phenyl, polyethylene glycol, alkyl-phosphonate, alkyl-sulfonate, methylene-triazole-alkyl-sulfonate, methylene-triazole-alkyl-phosphonate, methylene-triazole-methylene-dimethylammonium-alkyl-sulfonate, or methylene-dimethylammonium-alkyl-phosphonate; X=alkyl, phenyl, alkyl-carboxylic acid, alkyl ester, alkyl hydroxysuccinimde ester, alkyl maleimide, alkyl isothiocyanate, alkyl azide, alky alkyne, alkyl haloacetamido, aryl ester, aryl hydroxysuccinimde ester, aryl maleimide, aryl isothiocyanate, aryl azide, aryl alkyne, or aryl haloacetamido; $Y^1$ and $Y^2$ are each independently H, alkoxy-triazole-methylene-sulfonate, alkoxy-triazole-methylene-dimethylammonium-alkyl-sulfonate, alkoxy-triazole-methylene-phosphonate, alkoxy-triazole-methylene-dimethylammonium-alkyl-phosphonate, triazole-methylene-sulfonate, triazole-methylene-phosphonate, triazole-methylene-dimethylammonium-alkyl-sulfonate, triazole-methylene-methylene-dimethylammonium-alkyl-phosphonate, or one of the reactive groups listed as X; $Z^1$ and $Z^2$ are each independently CH or N; and $W^1$, $W^2$, $W^3$, and $W^4$ are each independently H or OH.

In certain embodiments, the squaraine rotaxane may have the formula:

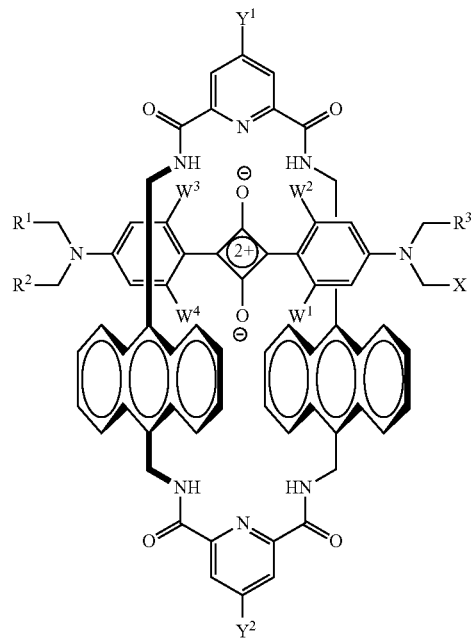

or a pharmaceutically acceptable salt thereof, wherein: $R^1$, $R^2$, and $R^3$ are each independently alkyl, phenyl, polyethylene glycol, alkyl-phosphonate, alkyl-sulfonate, methylene-triazole-alkyl-sulfonate, methylene-triazole-alkyl-phosphonate, methylene-triazole-methylene-dimethylammonium-alkyl-sulfonate, or methylene-dimethylammonium-alkyl-phosphonate; X=alkyl, phenyl, alkyl-carboxylic acid, alkyl ester, alkyl hydroxysuccinimde ester, alkyl maleimide, alkyl isothiocyanate, alkyl azide, alky alkyne, alkyl haloacetamido, aryl ester, aryl hydroxysuccinimde ester, aryl maleimide, aryl isothiocyanate, aryl azide, aryl alkyne, or aryl haloacetamido; $Y^1$ and $Y^2$ are each independently H, alkoxy-triazole-methylene-sulfonate, alkoxy-triazole-methylene-dimethylammonium-alkyl-sulfonate, alkoxy-triazole-methylene-phosphonate, alkoxy-triazole-methylene-dimethylammonium-alkyl-phosphonate, triazole-methylene-sulfonate, triazole-methylene-phosphonate, triazole-methylene-dimethylammonium-alkyl-sulfonate, triazole-methylene-methylene-dimethylammonium-alkyl-phosphonate, or one of the reactive groups listed as X; and $W^1$, $W^2$, $W^3$, and $W^4$ are each independently H or OH.

In certain embodiments, the squaraine rotaxane may have the formula:

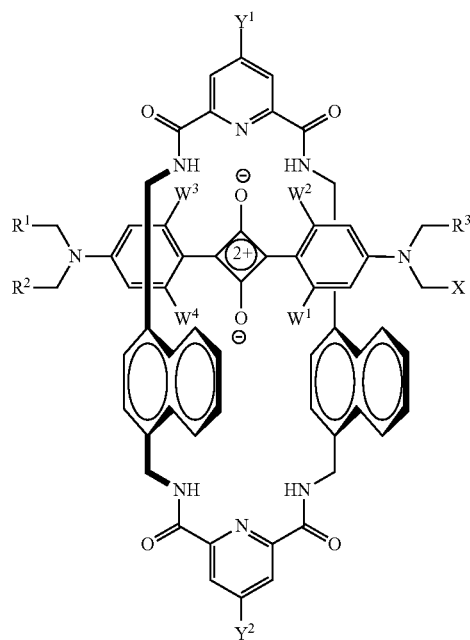

or a pharmaceutically acceptable salt thereof, wherein: $R^1$, $R^2$, and $R^3$ are each independently alkyl, phenyl, polyethylene glycol, alkyl-phosphonate, alkyl-sulfonate, methylene-triazole-alkyl-sulfonate, methylene-triazole-alkyl-phosphonate, methylene-triazole-methylene-dimethylammonium-alkyl-sulfonate, or methylene-dimethylammonium-alkyl-phosphonate; X=alkyl, phenyl, alkyl-carboxylic acid, alkyl ester, alkyl hydroxysuccinimde ester, alkyl maleimide, alkyl isothiocyanate, alkyl azide, alky alkyne, alkyl haloacetamido, aryl ester, aryl hydroxysuccinimde ester, aryl maleimide, aryl isothiocyanate, aryl azide, aryl alkyne, or aryl haloacetamido, $Y^1$ and $Y^2$ are each independently H, alkoxy-triazole-methylene-sulfonate, alkoxy-triazole-methylene-dimethylammonium-alkyl-sulfonate, alkoxy-triazole-methylene-phosphonate, alkoxy-triazole-methylene-dimethylammonium-alkyl-phosphonate, triazole-methylene-sulfonate, triazole-methylene-phosphonate; triazole-methylene-dimethylammonium-alkyl-sulfonate, triazole-methylene-methylene-dimethylammonium-alkyl-phosphonate; or one of the reactive groups listed as X; and $W^1$, $W^2$, $W^3$, and $W^4$ are each independently H or OH.

In embodiments, the exemplary compounds described above may be synthesized according to the following general procedures. In some embodiments, symmetrical squaraine dyes are prepared in one step by heating two equivalents of the appropriate aniline derivative with squaric acid. In other embodiments, unsymmetrical squaraines are prepared in two steps via a stable semi squaraine intermediate (see, e.g., FIG. 1).

In some embodiments, a subsequent template macrocyclization step yields a squaraine rotaxane dye, as shown in the example below using an aniline-based squaraine.

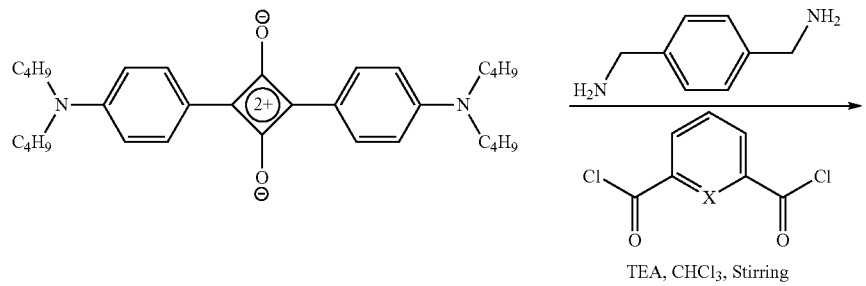

TEA, CHCl$_3$, Stirring

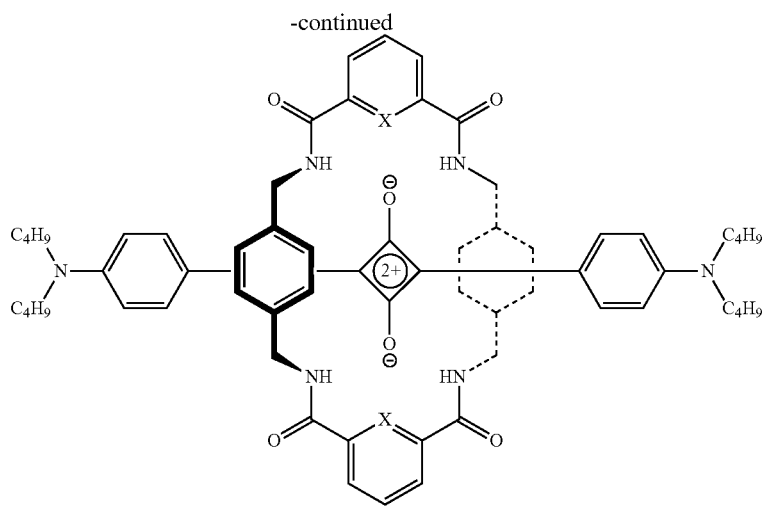
It was not known prior to the present disclosure that this procedure may be used to prepare aniline-based squaraine rotaxanes with ortho-hydroxyl groups on the aniline rings, such as the following example.
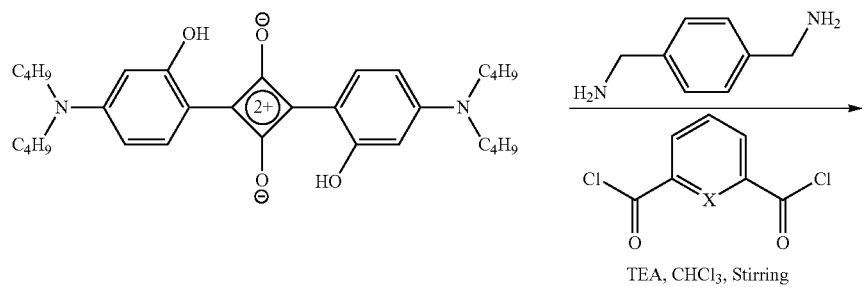
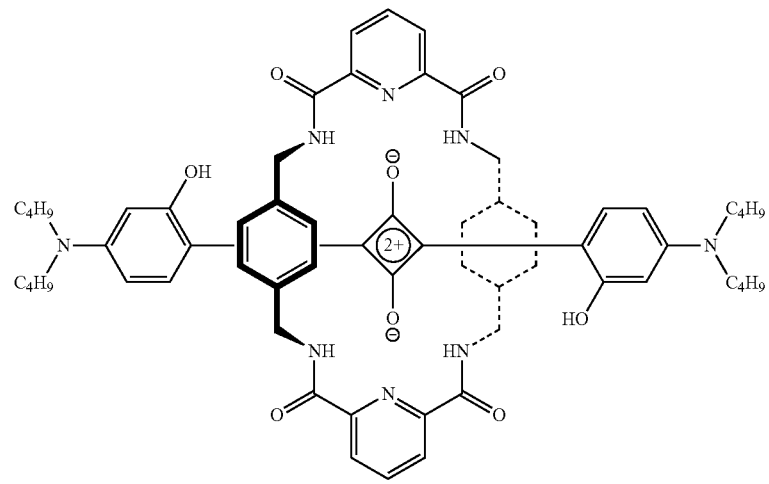

The product of this reaction has the following spectral data. $^1$H NMR: 0.96 (t, J=7.4 Hz, 12H), 1.30 (dd, J=7.4 Hz, 7.0 Hz, 8H), 1.52 (br s, 8H), 3.22 (t, J=6.6 Hz, 8H), 3.93 (d, J=14.0 Hz, 4H), 5.08 (m, 6H), 5.98 (d, J=2.0 Hz, 2H), 6.73 (d, J=9.0 Hz, 4H), 6.93 (d, J=9.0 Hz, 4H), 7.73 (d, J=9.2 Hz, 2H), 8.1 (t, J=8.0 Hz, 2H), 8.50 (d, J=7.8 Hz, 4H), 9.88 (d, J=8.8 Hz, 4H), 11.2 (s, 2H); Abs: 651 nm; Em: 672 nm.

Aniline-based squaraine rotaxanes with ortho-hydroxyl groups are a novel set of squaraine rotaxanes that exhibit highly favorable chemical and photophysical performance, due in part to the hydrogen bonding between the ortho-hydroxyl groups and the squaraine oxygens which provides structural rigidity and blocks chemical attack. Another favorable attribute gained by the presence of ortho-hydroxyl groups is reduced fluorescence quenching by water. This may be demonstrated by comparing compound 1, which has no ortho-hydroxyls attached to the anilines, with compound 2, which has two ortho-hydroxyls attached to one of the anilines. Photophysical measurements in two solvents, tetrahydrofuran (THF) and THF:water (1:1), show that the fluorescence quantum yield of compound 1 decreases by 33% when the solvent is changed from THF to THF:Water (1:1). This is due to the squaraine quenching effect of water. In contrast, the fluorescence quantum yield of compound 2 is not altered when the solvent is changed from THF to THF:water (1:1). This demonstrates that the fluorescence brightness of squaraine rotaxanes with ortho-hydroxyl groups is insensitive to solvent and local environment, a valuable property in quantitative imaging and sensing technologies.

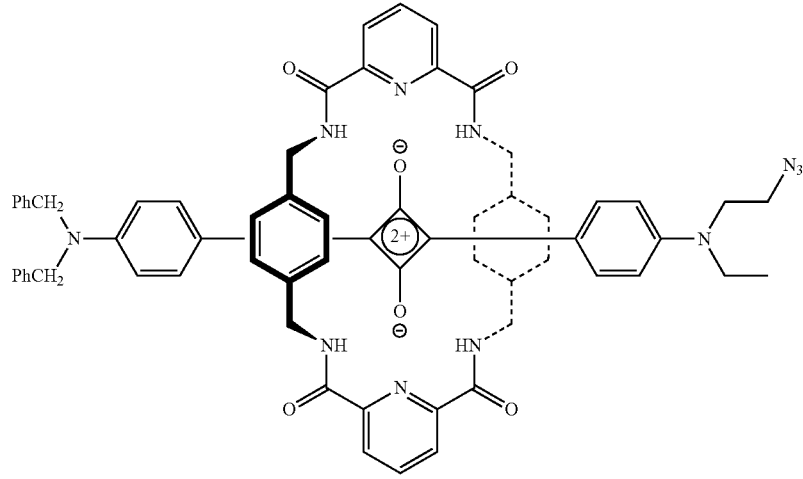

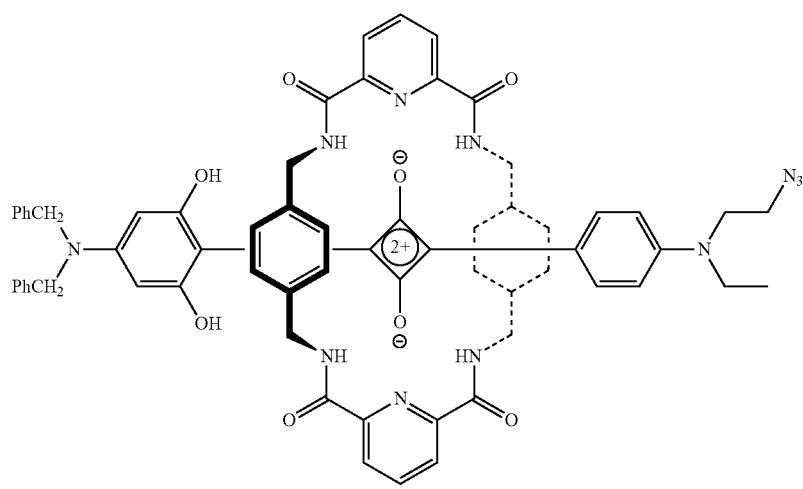

Compound 1: In THF; Abs 637 nm; Em 655 nm, QY=0.58. In THF:water (1:1); Abs 644 nm; Em 664 nm, QY=0.39.
Compound 2: In THF: Abs 640 nm; Em 666 nm, QY=0.33. In THF:water (1:1); Abs 651 nm; Em 677 nm, QY=0.33.

With anthracene containing macrocycles, a new class of squaraine rotaxane dyes may be formed by a slippage process that involves mixing the squaraine and the macrocycle components and using heat, or microwave radiation to induce the squaraine dye to slip inside the macrocycle to form a squaraine rotaxane intermediate that may be further modified. One embodiment of this synthesis is as follows.

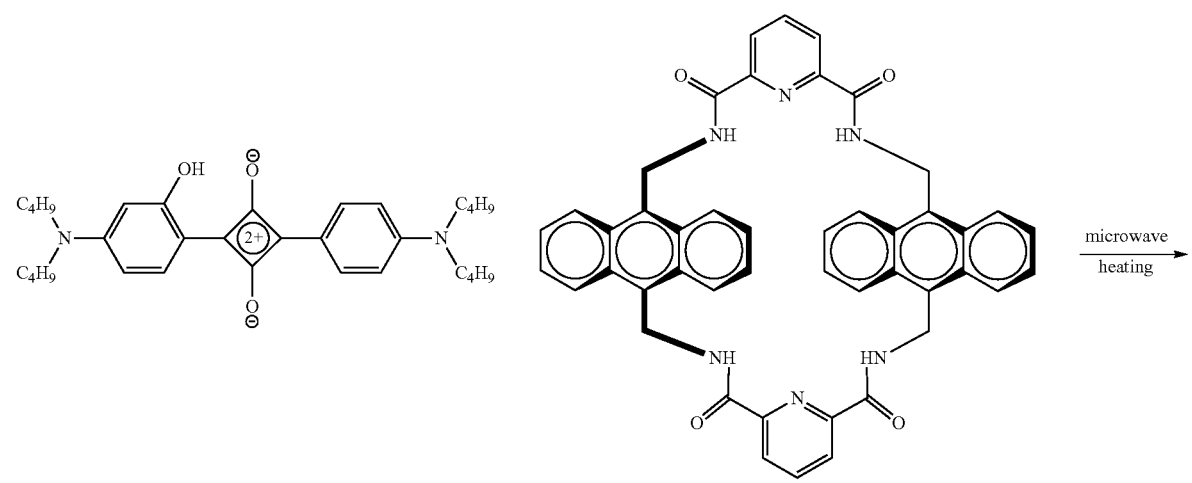

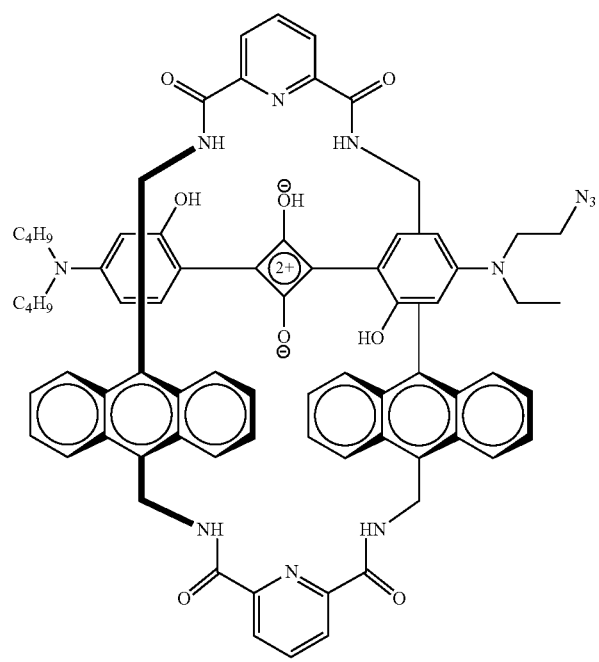

The product of this reaction has the following spectral data. $^1$H NMR (600 MHz, CDCl$_3$) 0.89 (m, 6H), 1.07 (t, J=7.8 Hz, 3H), 1.20 (m, 4H), 1.46 (m, 4H), 1.71 (m, 2H), 3.42 (m, 8H), 6.53 (d, J=9.0 Hz, 2H), 6.61 (d, J=9.0 Hz, 2H), 6.72 (d, J=9.0 Hz, 1H), 6.83 (d, J=8.4 Hz, 1H), 7.35 (m, 8H), 6.94 (d, J=8.4 Hz, 1H), 7.76 (d, J=9.0 Hz, 4H), 7.82 (d, J=9.0 Hz, 4H), 8.67 (d, J=7.8 Hz, 4H), 8.22 (dd, J=7.8, 4.2 Hz, 2H), 9.76 (t, J=4.8 Hz, 4H), 11.25 (s, 1H), 5.37 (d, J=10 Hz, 8H); Abs: 653 nm; Em: 703 nm.

Exemplary squaraine rotaxanes with one or more sulfonate or zwitterionic groups attached and one or more reactive sites for bioconjugation were generated and tested. Efficient and effective methods for attaching sulfonate groups or zwitterionic groups to squaraine rotaxanes were not known prior to the present disclosure. In embodiments, the squaraine rotaxane may be modified and groups may be introduced that provide water solubility and reactivity using the conjugation method of forming triazole linkages using a copper catalyzed azide alkyne cycloaddition reaction, as shown in the following exemplary reaction.

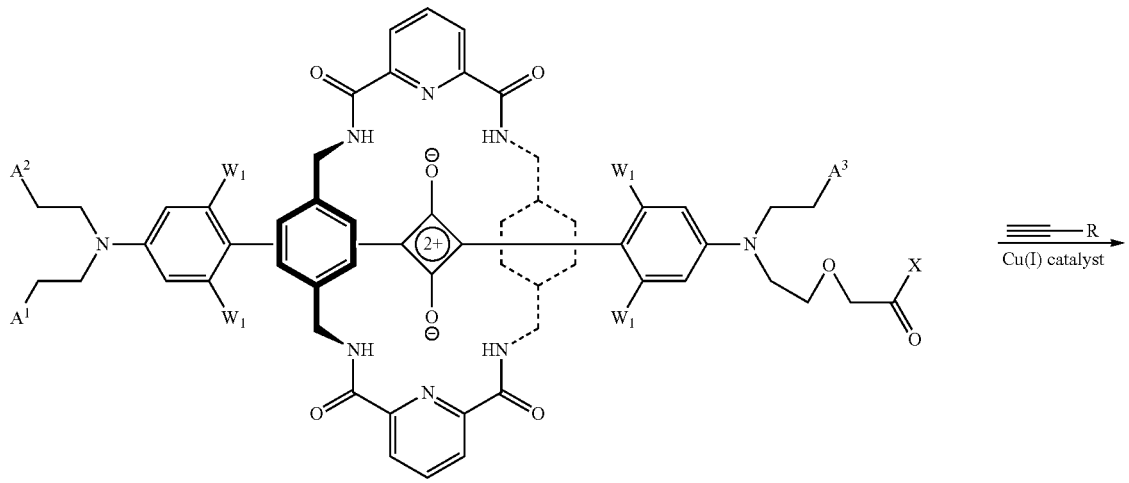

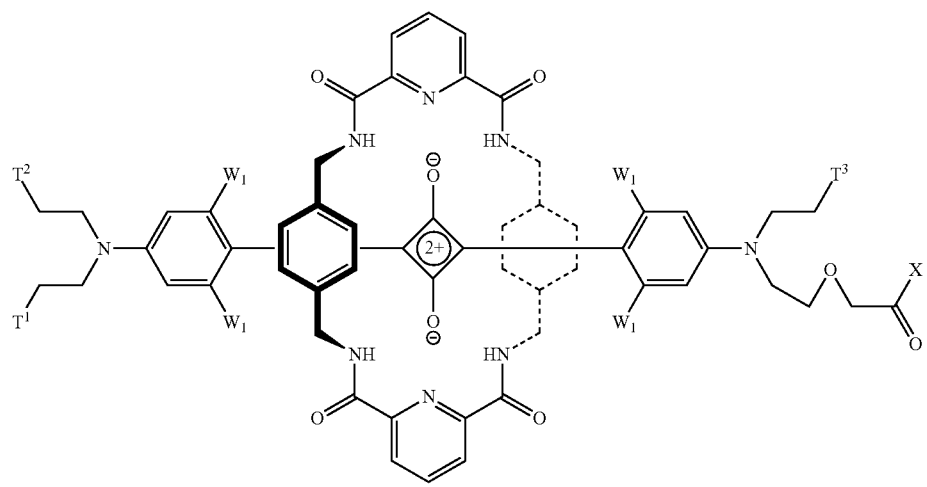

17
Where $A^1$, $A^2$, $A^3$, $A^4$, and $A^5$ are each independently H or azido ($N_3$); $T^1$, $T^2$, $T^3$, $T^4$, and $T^5$ are each independently H or
18
1,3-triazole rings; and $W^1$, $W^2$, $W^3$, and $W^4$ are each independently H or OH.
One embodiment of this synthesis is as follows.
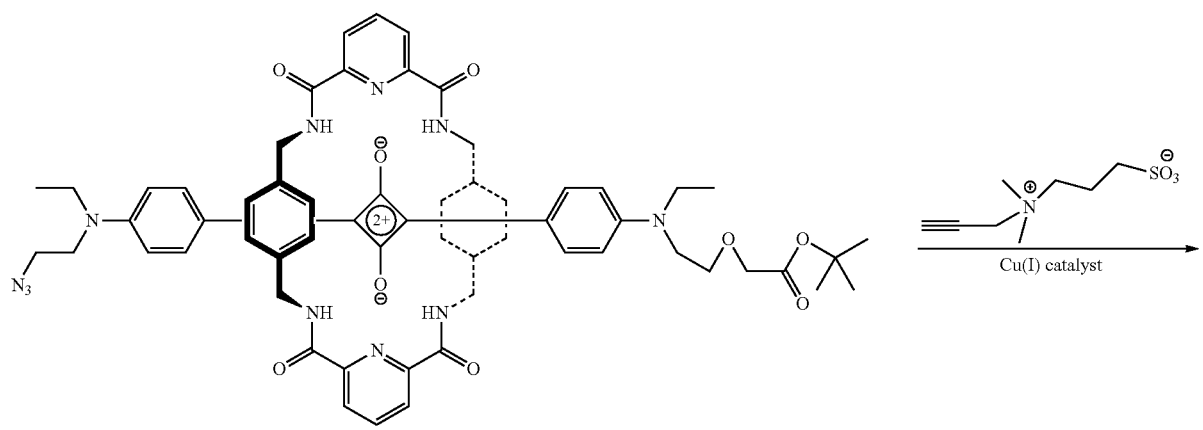
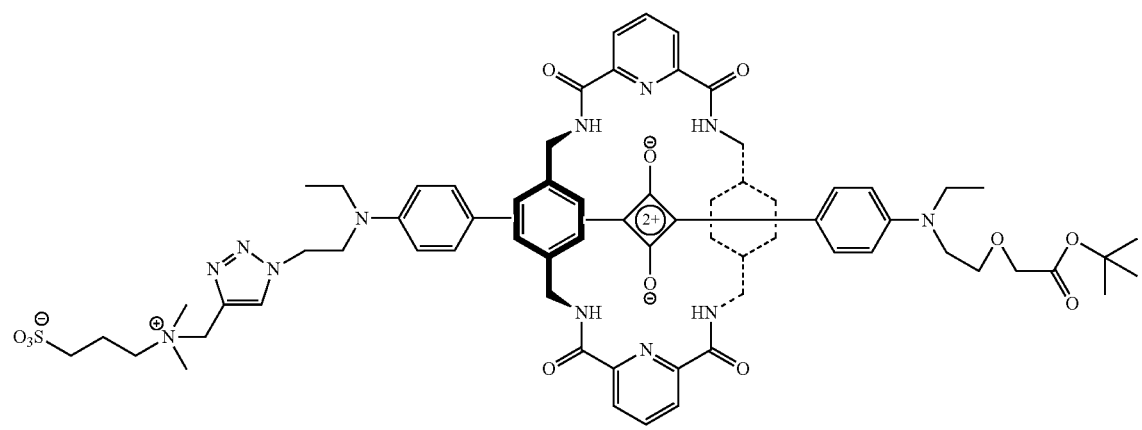

Figure 2:
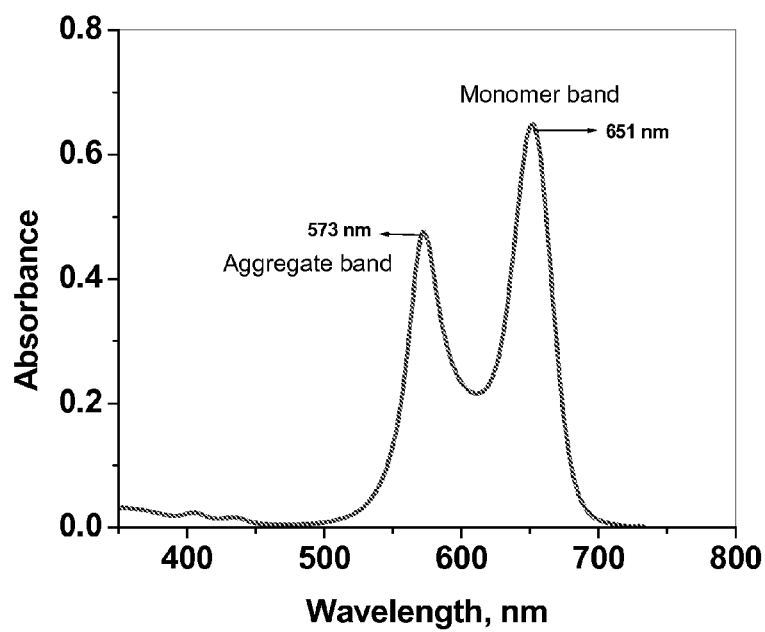
FIG. 2 illustrates absorption spectra of an aggregated squaraine rotaxane 3 in DMSO:PBS (1:4), and illustrates a strong aggregate band at 573 nm, in accordance with various embodiments.

It was not known prior to the present disclosure that particular modifications prevent aggregation of the squaraine rotaxanes in physiological fluids such as phosphate buffered saline (PBS). FIG. 2 shows an exemplary absorption spectrum of unmodified, lipophilic squaraine rotaxane 3 in a DMSO/PBS solvent mixture that promotes aggregation. Aggregates that exhibit the absorption band at 573 nm are not fluorescent.

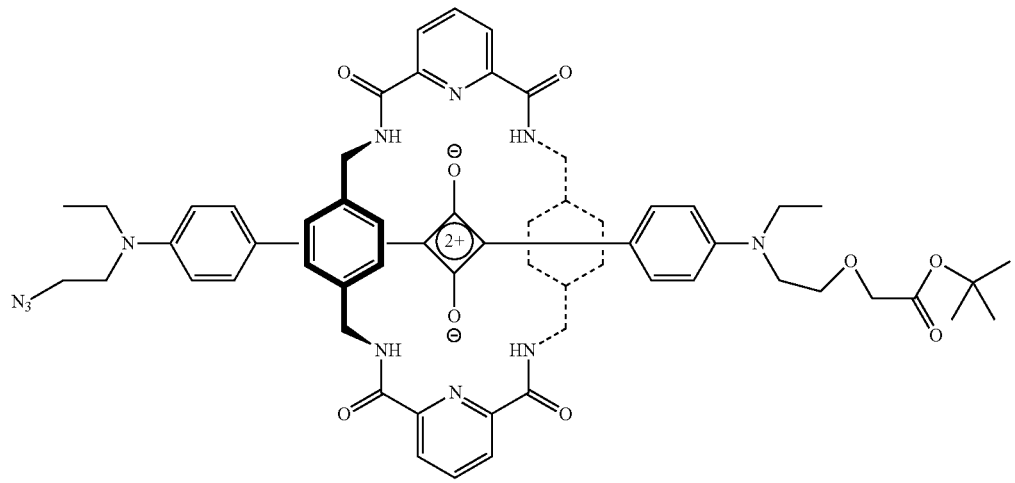

3

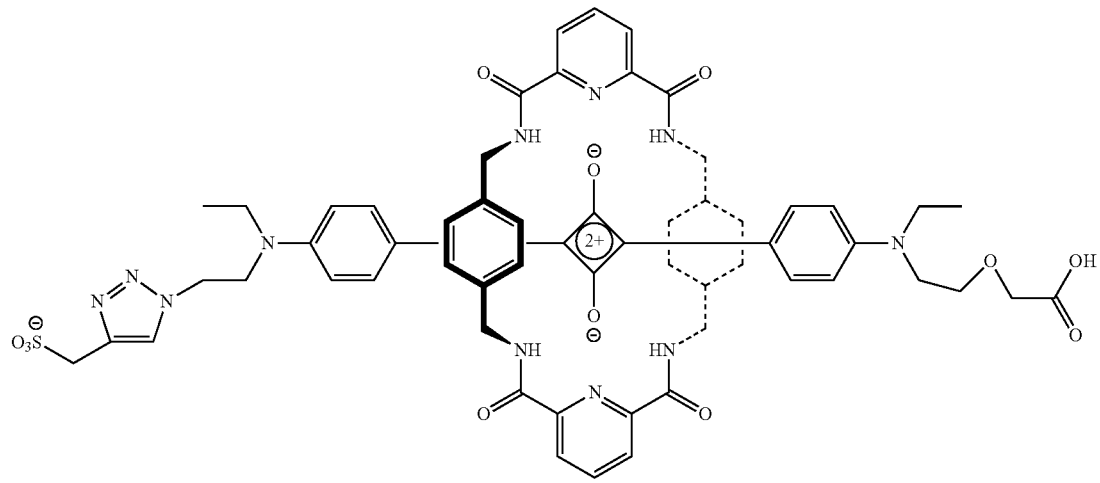

4

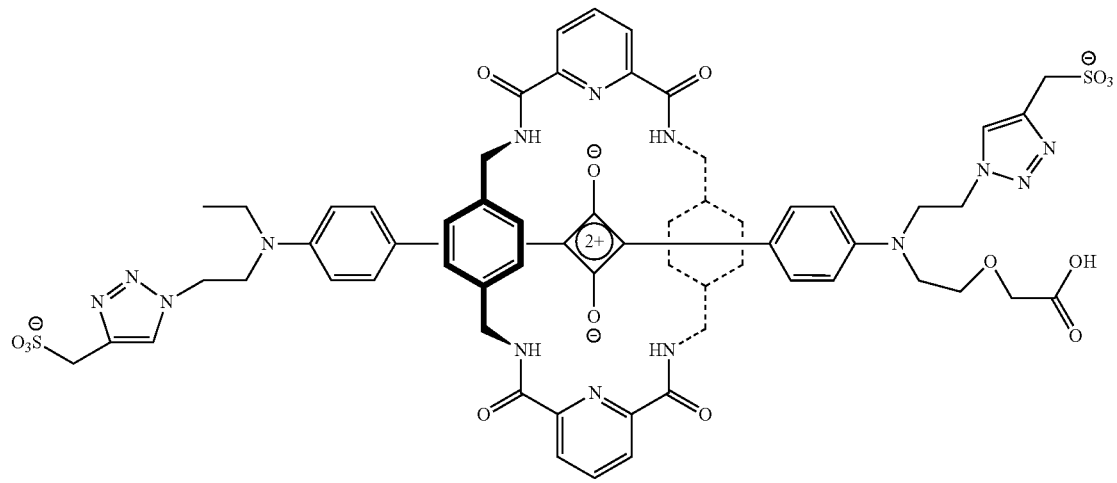

5

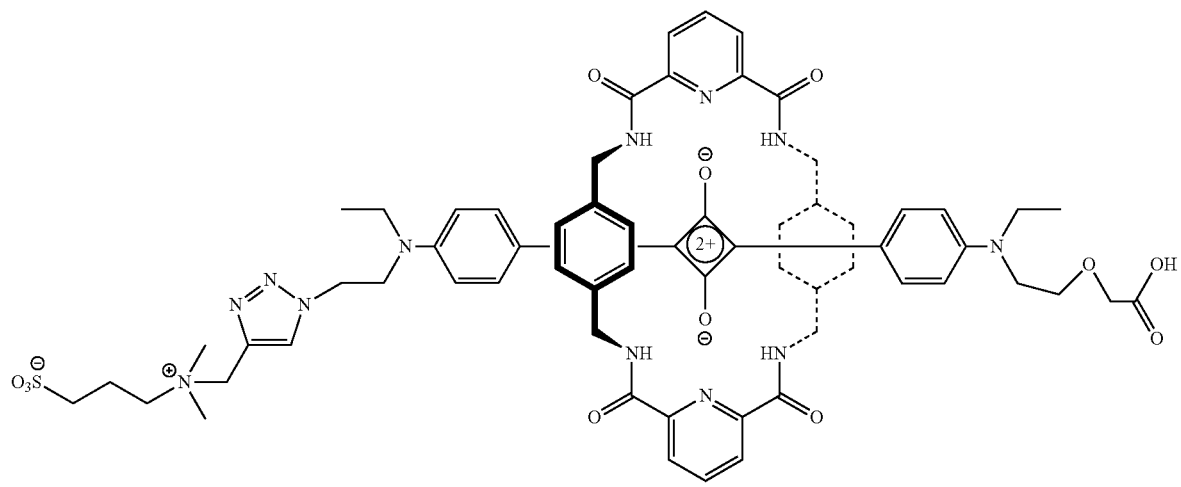

6

Figure 3:
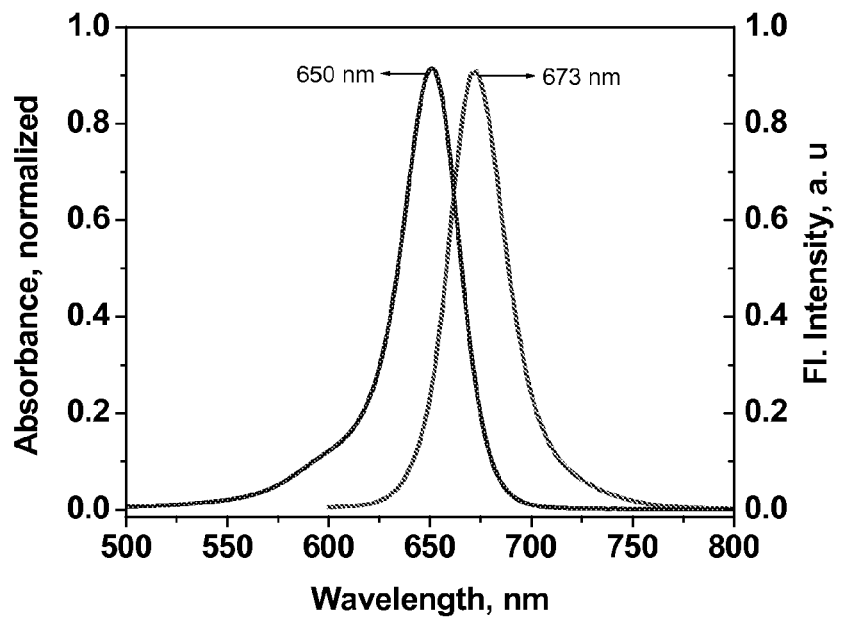
FIG. 3 illustrates a typical example of absorption (left peak) and emission (right peak) spectra of a non-aggregated squaraine rotaxane 4 in PBS attached with a single sulfonate group, in accordance with various embodiments.
Figure 4:
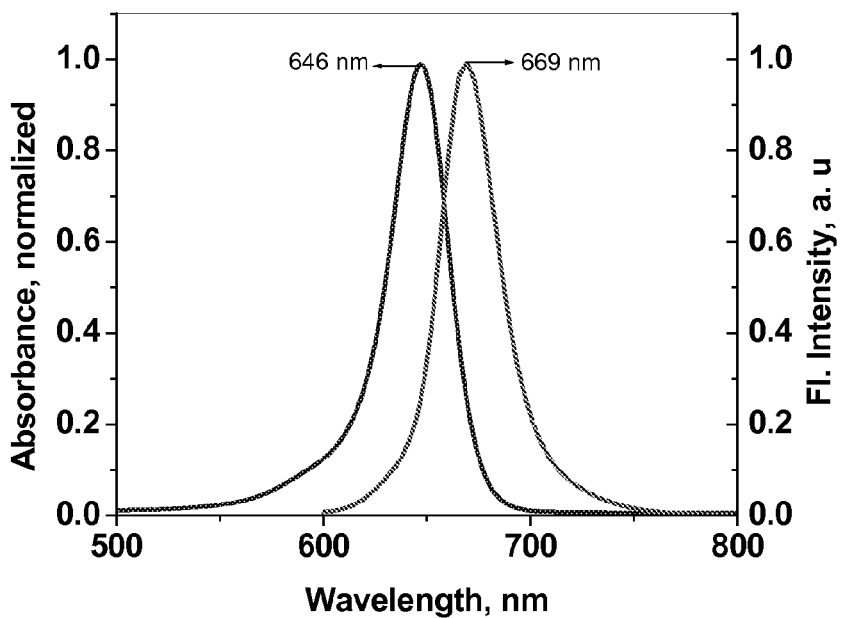
FIG. 4 illustrates a typical example of absorption (left peak) and emission (right peak) spectra of a non-aggregated squaraine rotaxane 5 in PBS attached with two sulfonate groups, in accordance with various embodiments.
Figure 5:
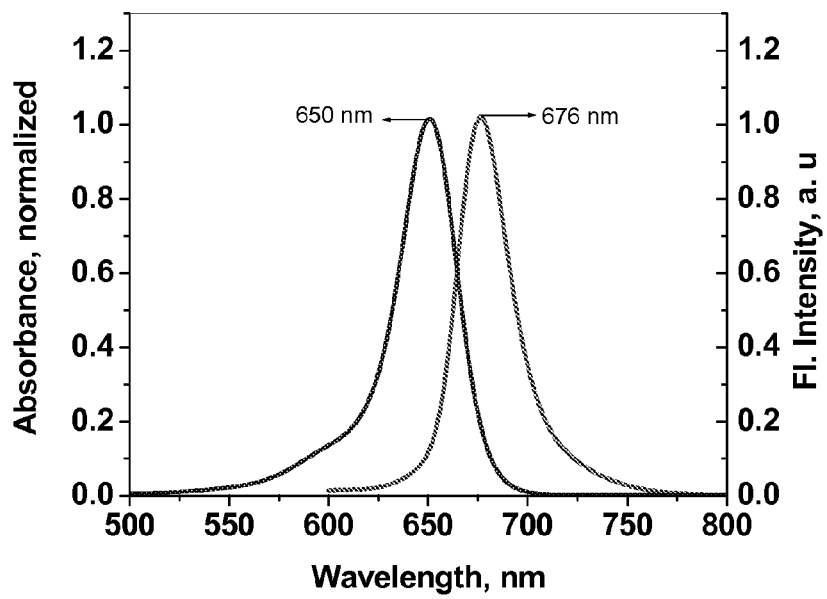
FIG. 5 illustrates a typical example of absorption (left peak) and emission (right peak) spectra of a non-aggregated squaraine rotaxane 6 in PBS attached with a-zwitterionic group, in accordance with various embodiments.

FIG. 3 illustrates an example of absorption (left peak) and emission (right peak) spectra in PBS of a squaraine rotaxane 4 attached with a single sulfonate group. There is no evidence of non-fluorescent aggregates. Similarly, FIG. 4 shows an example of absorption (left peak) and emission (right peak) spectra in PBS of a squaraine rotaxane 5 attached with two sulfonate groups. In further embodiments, squaraine rotaxanes with one or more zwitterionic groups may not form aggregates in PBS. For instance, FIG. 5 shows an example of absorption (left peak) and emission (right peak) spectra of a squaraine rotaxane 6 in PBS attached with a zwitterionic group.

In some embodiments, the squaraine rotaxanes are water soluble but overall uncharged because they have one or more attached polyethylene glycol or zwitterionic groups for water solubility and one or more reactive sites for bioconjugation. The attachment of a dye with many anionic or cationic groups to a biological molecule sometimes changes the charge pattern of the biological molecule to such an extent that its chemical, biochemical or supramolecular properties are altered adversely. In another embodiment, the attachment of a dye having many anionic groups or many cationic groups to a biological molecule produces a bioconjugate that when introduced into an animal is not likely to be cleared primarily from the bloodstream by the kidney, which complicates imaging performance. These problems are solved, in embodiments, by creating squaraine rotaxanes with one or more polyethyleneglycol or zwitterionic groups for water solubility and one or more reactive sites for bioconjugation. In embodiments, the overall net charge of these compounds is zero or close to zero. In embodiments, these compounds have excellent water solubility and excellent stability, do not form non-fluorescent aggregates in PBS, and have a greater tendency to clear from the bloodstream of animals through the kidney.

Surprisingly, in embodiments, squaraine rotaxanes with one or more attached sulfonates or attached zwitterionic groups are very photostable, even when they are associated with proteins that normally quench other dyes. The following exemplary probe molecule biotin-squaraine rotaxane (SQR-biotin) was synthesized:

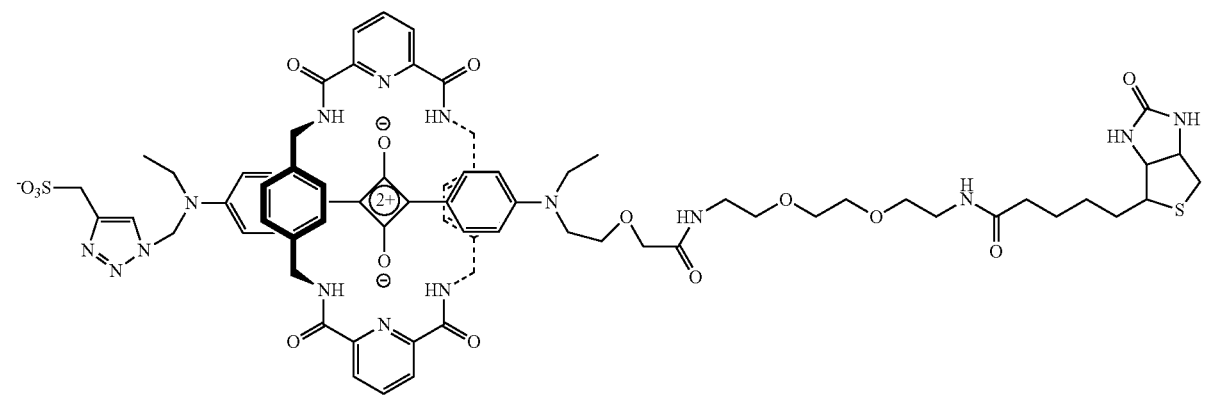

The probe SQR-biotin is a squaraine rotaxane with an attached sulfonate that gives excellent water solubility, and an attached biotin group that has strong affinity for the protein avidin or related variants such as streptavidin. The complex of this probe associated with streptavidin is very photostable compared to complexes made with other dyes.

Figure 6:
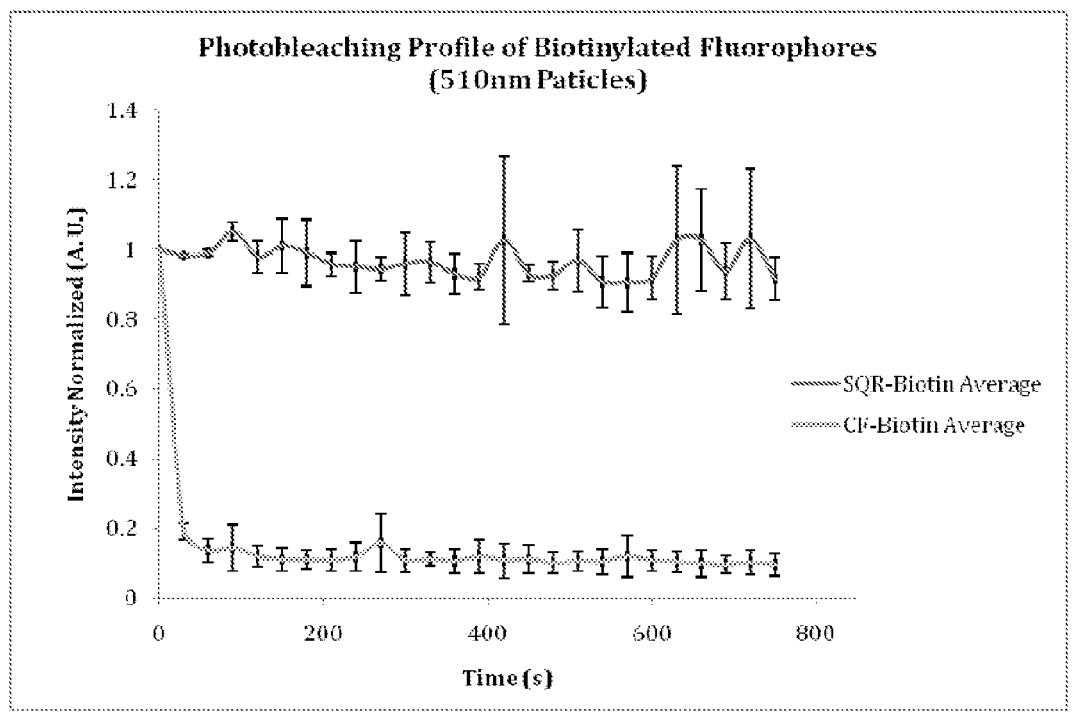
FIG. 6 illustrates a photobleaching profile of biotinylated fluorophores, in accordance with various embodiments.

In one specific, non-limiting example, the photobleaching of commercially available biotin-4-carboxyfluorescein (CF-biotin), and biotin-squaraine rotaxane (SQR-biotin) was examined by measuring the half-life of each of the probes. The dyes were incubated in excess with 1.3 μm magnetic particles coated in avidin. Following the incubation, the particles were washed of any unbound fluorophore, and the samples were then imaged on an epifluorescent microscope. The samples remained under constant excitation and images were captured every 30 seconds. Using ImageJ software, a region of interest (ROI) was drawn around the imaged magnetic particles and the mean pixel intensity was measured for each image. These data were then plotted versus time, and the half-life was calculated. FIG. 6 shows the photobleaching profile of the two biotinylated fluorophores. The biotin-4-carboxyfluorescein probe showed dramatic photobleaching, but the biotin-squaraine rotaxane probe retained fluorescence intensity throughout the duration of the test.

Figure 7:
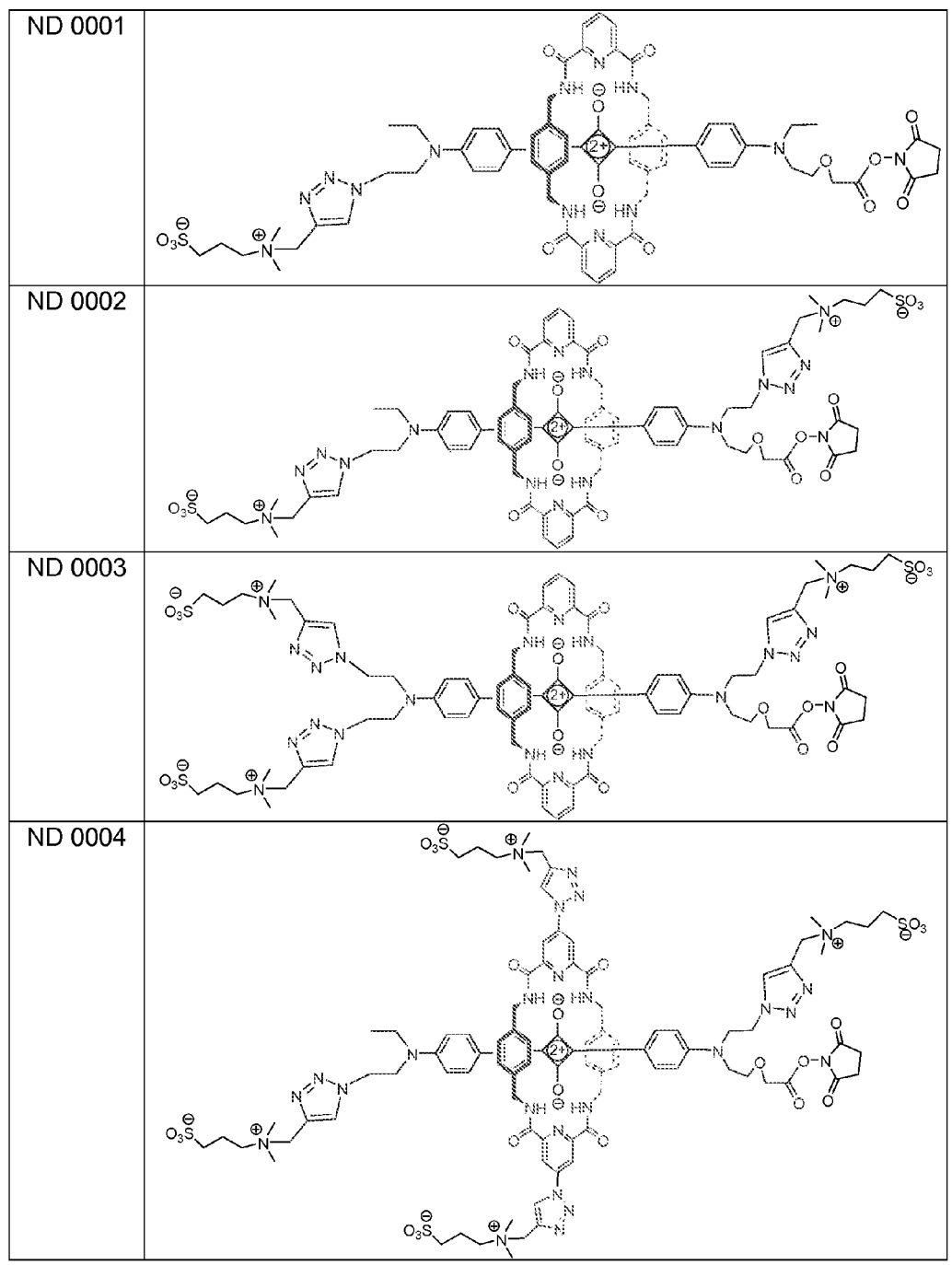
FIG. 7 illustrates exemplary squaraine rotaxane dyes, in accordance with various embodiments.
Figure 7:
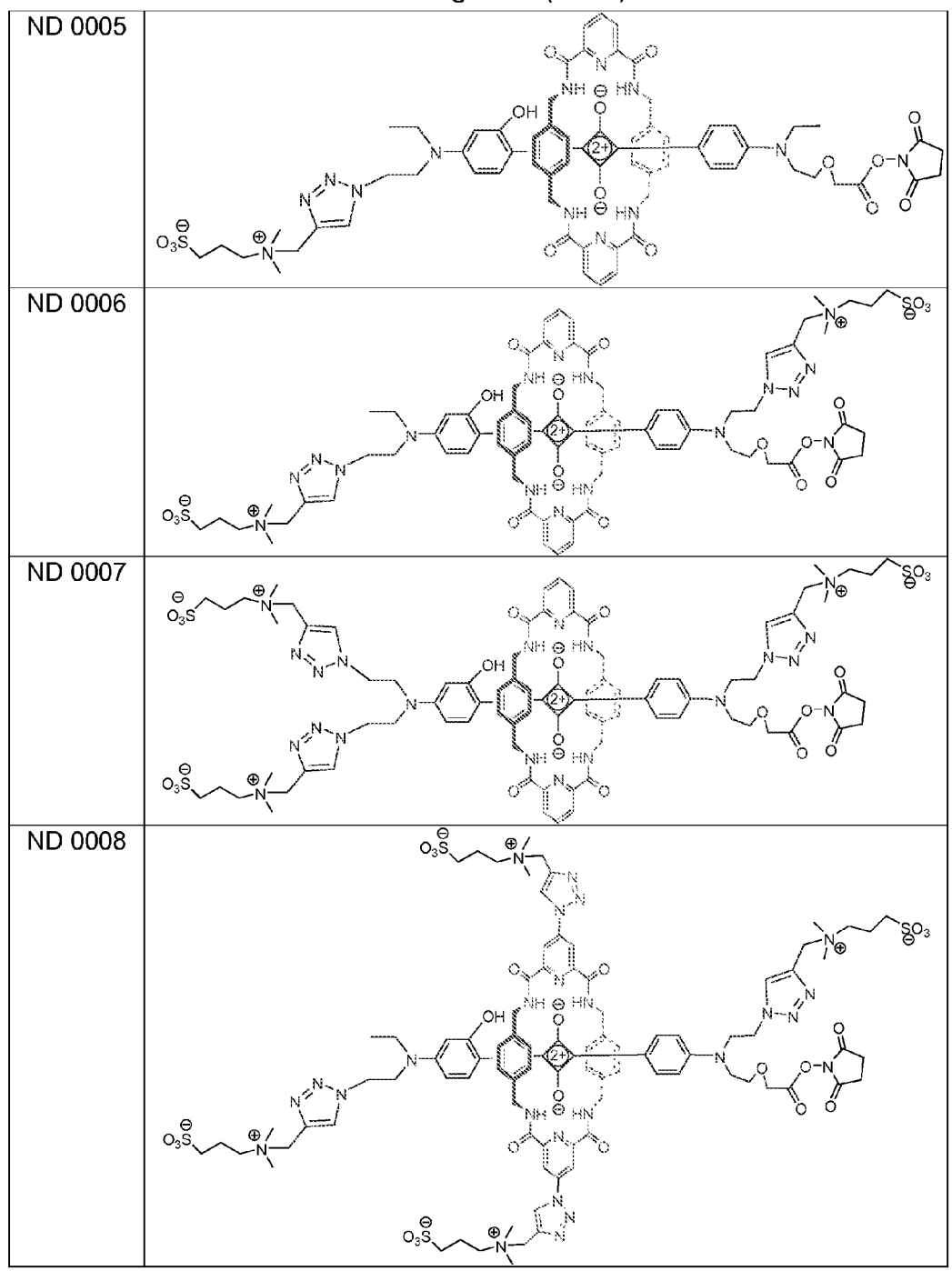
Figure 7:
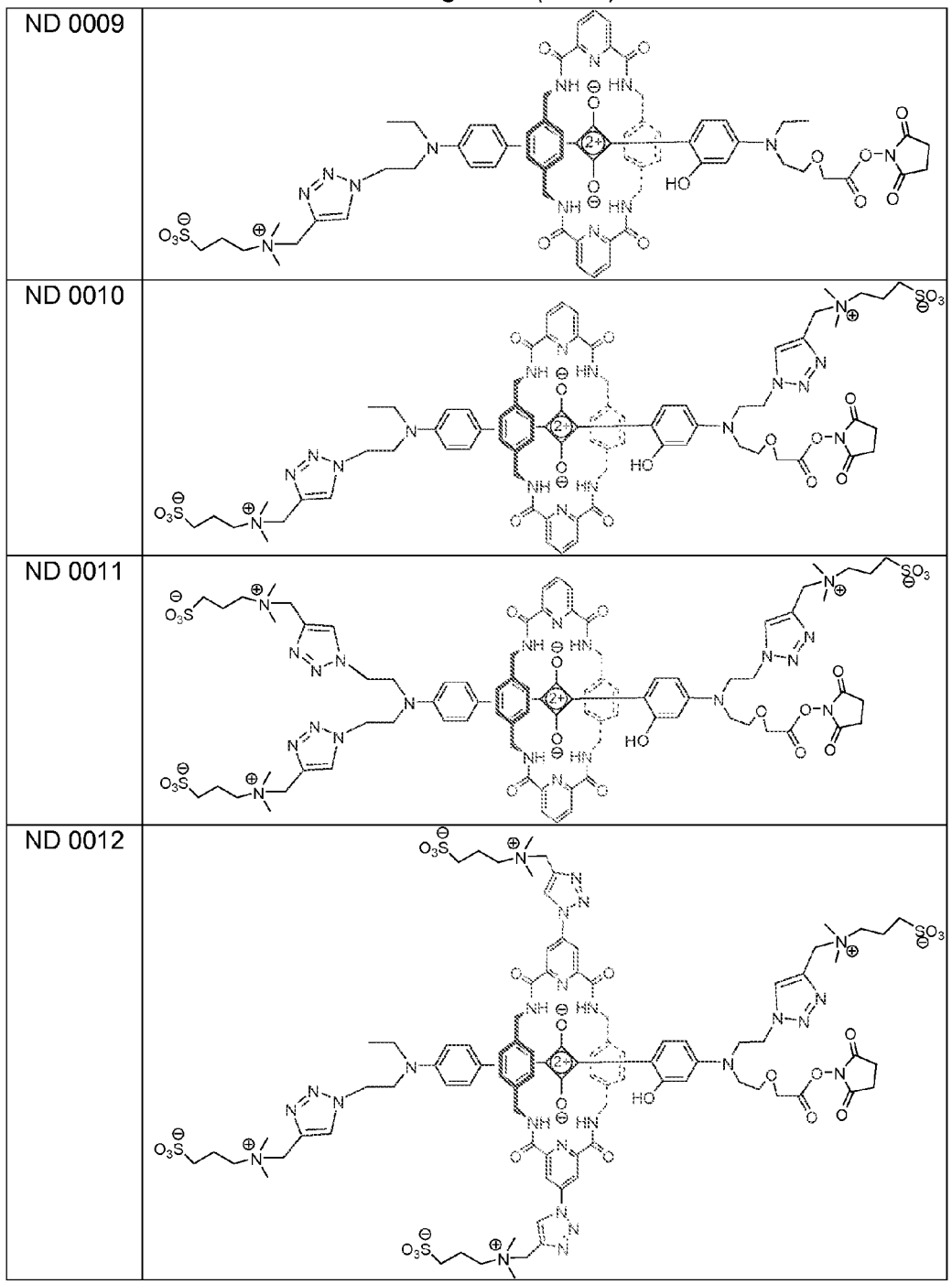
Figure 7:
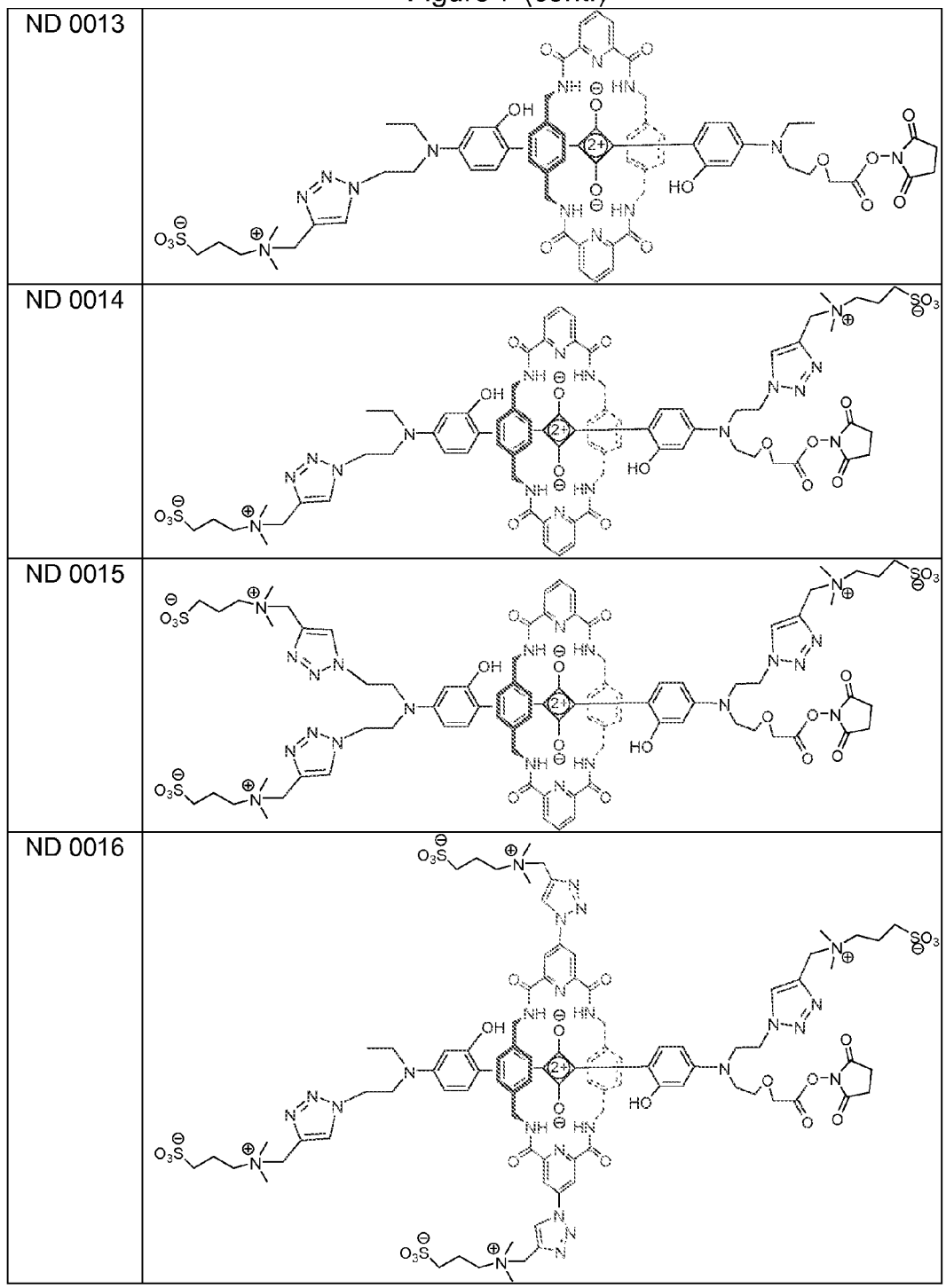
Figure 7:
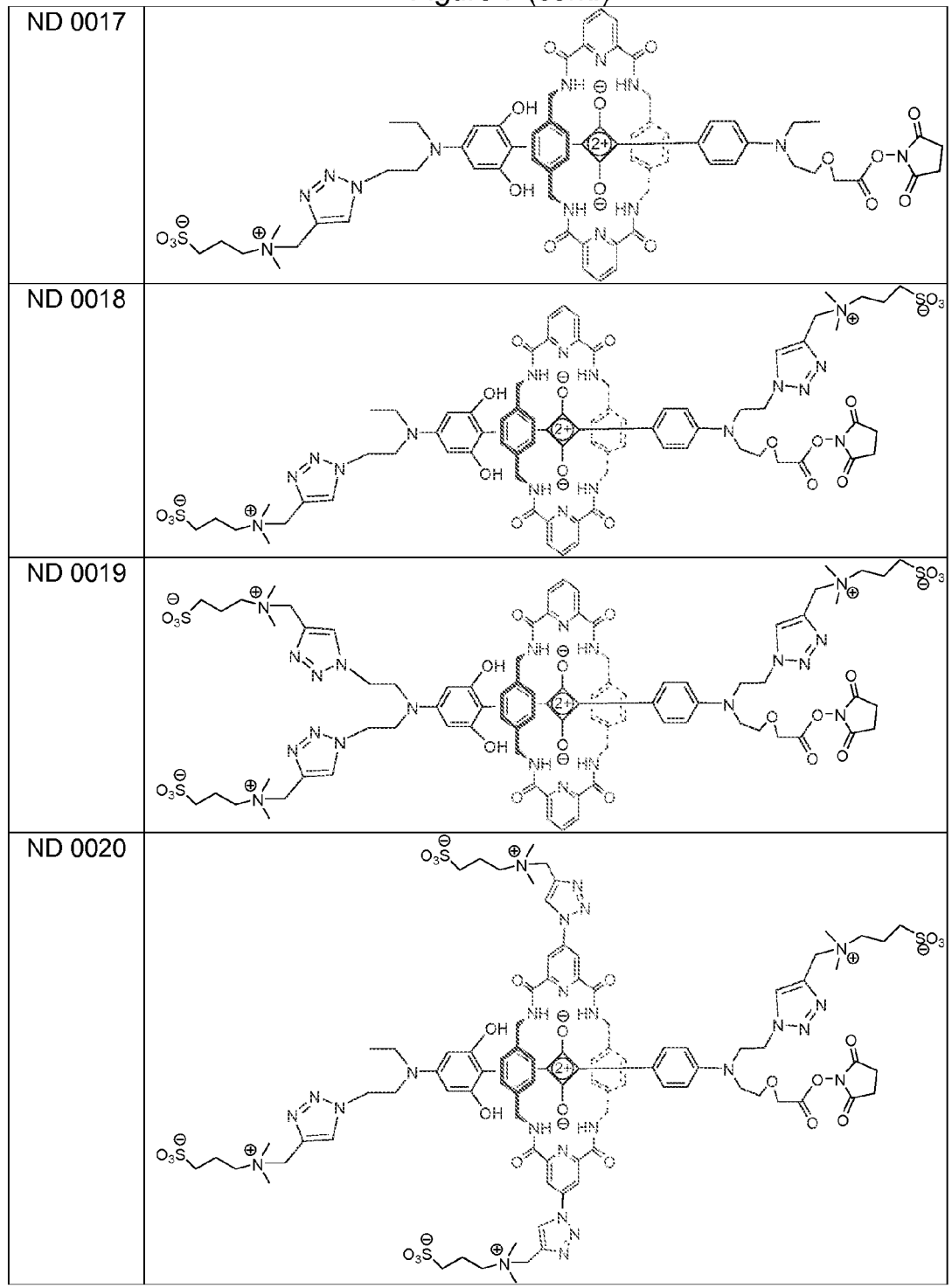
Figure 7:
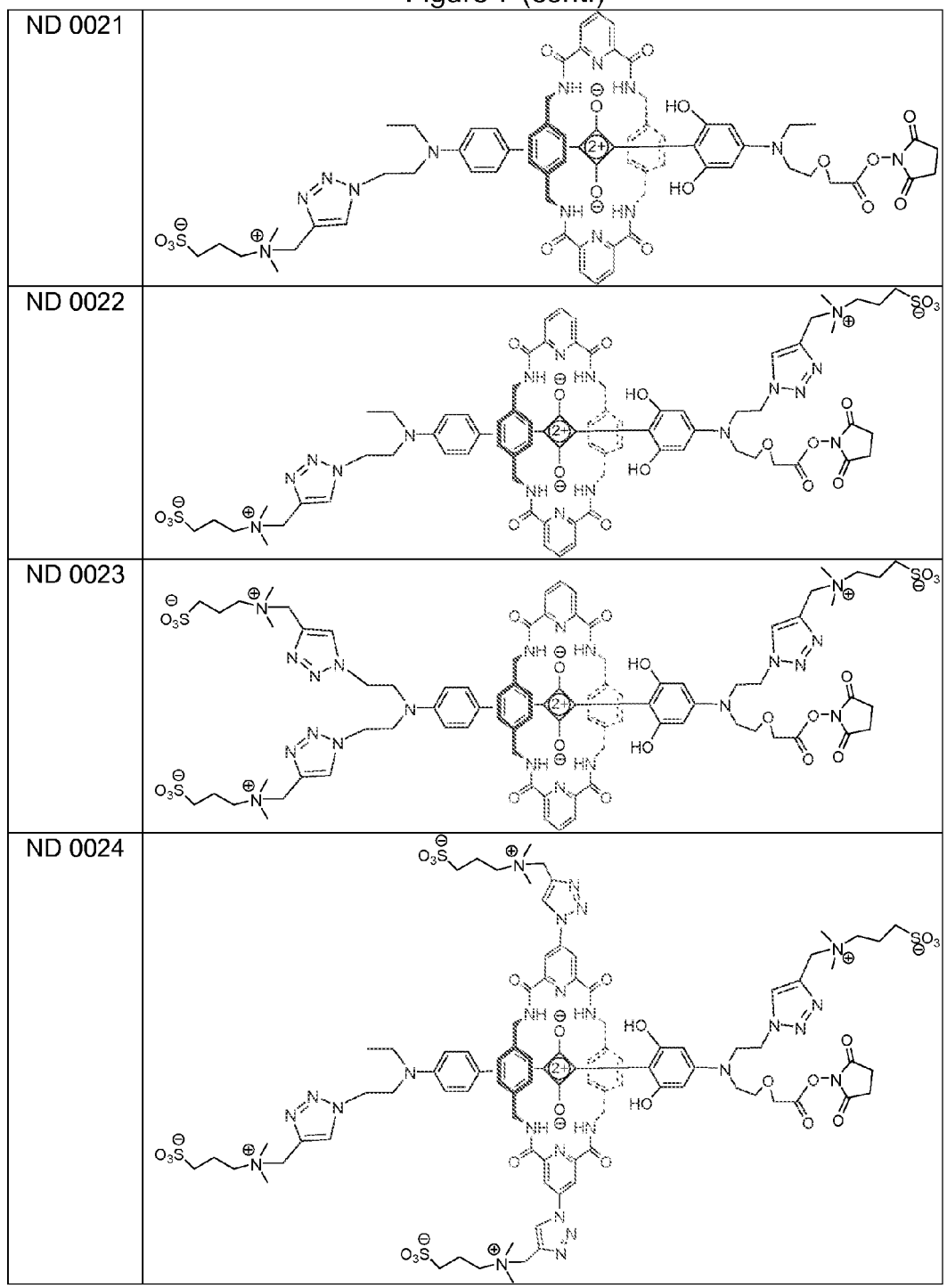
Figure 7:
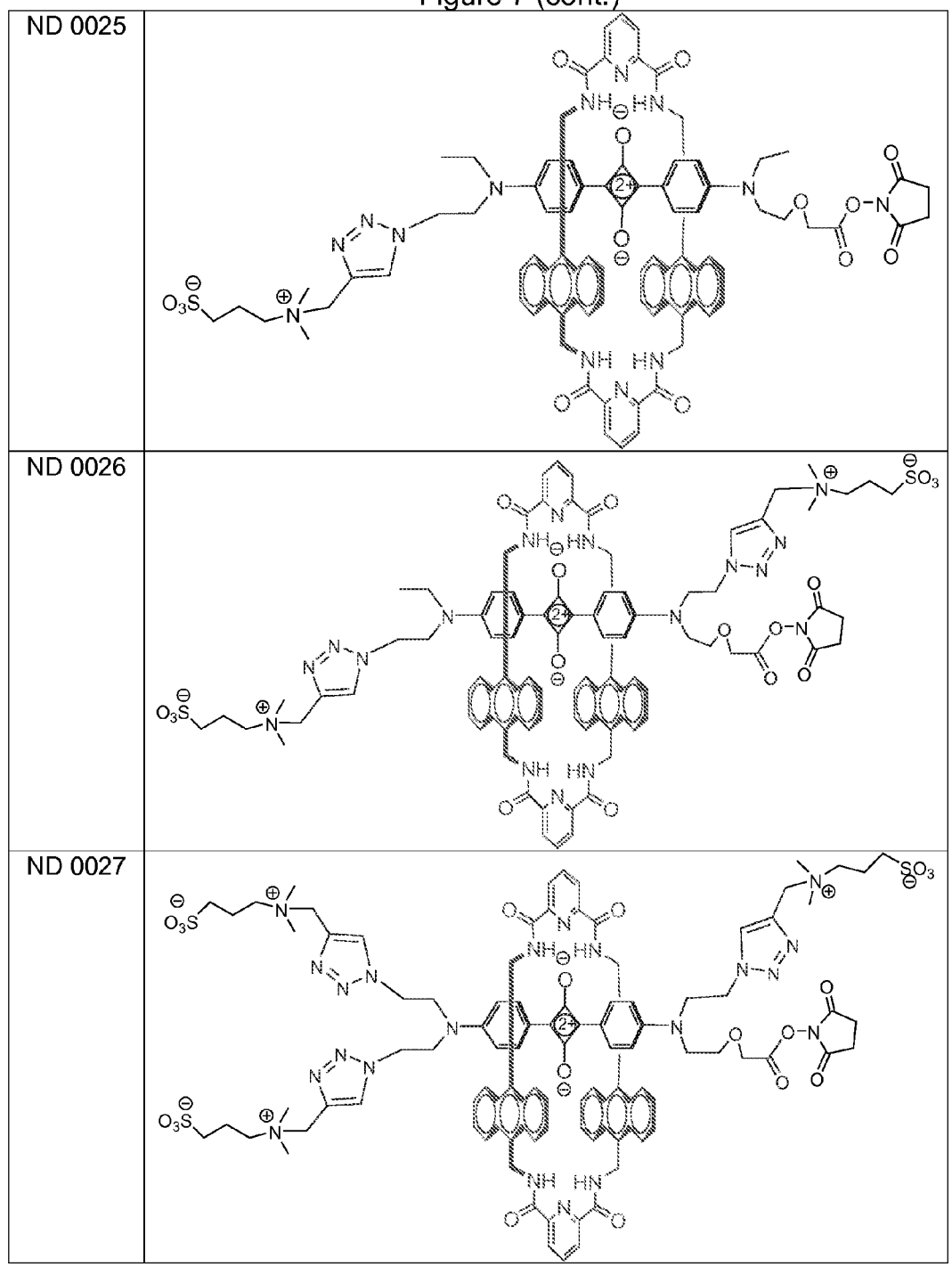
Figure 7:
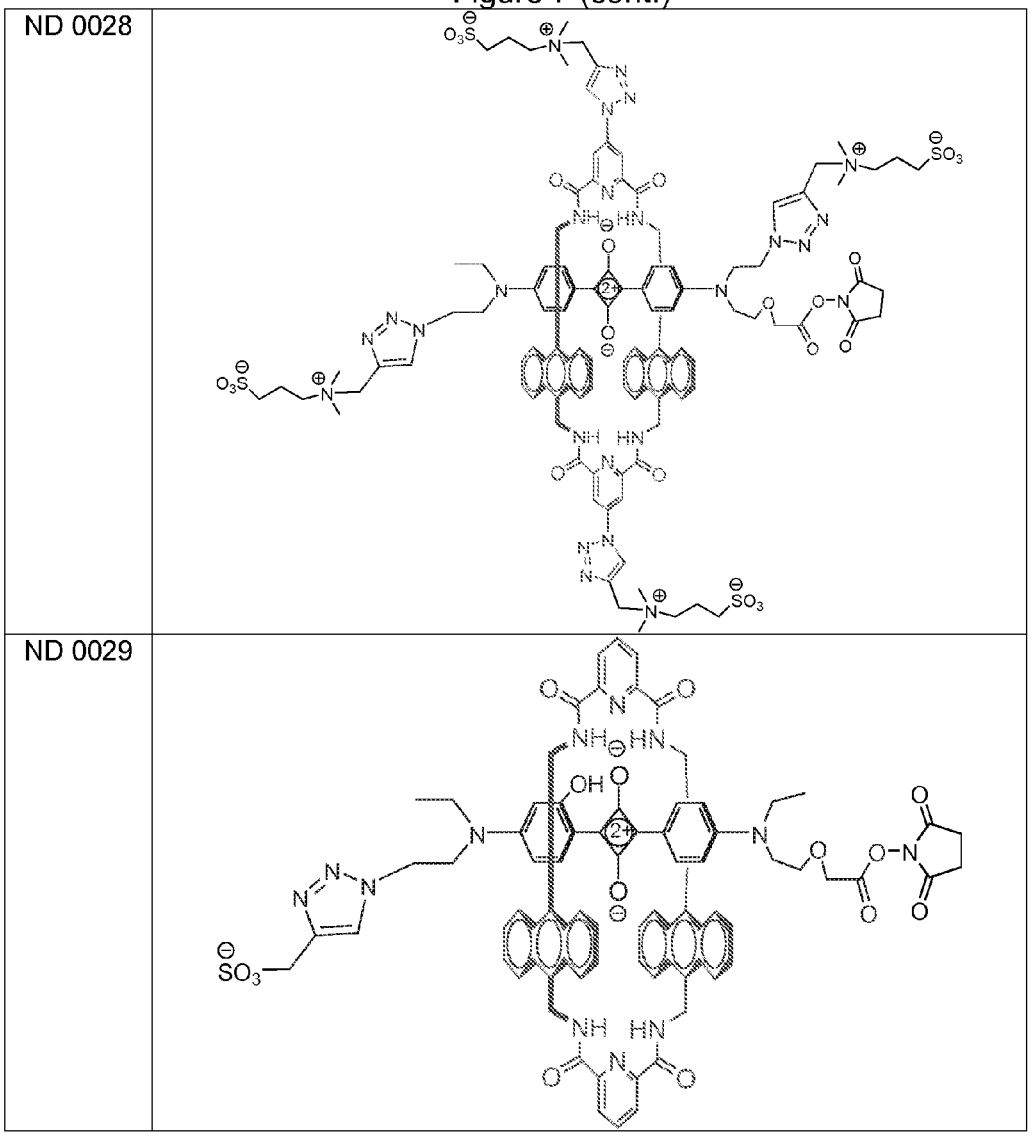
Figure 7:
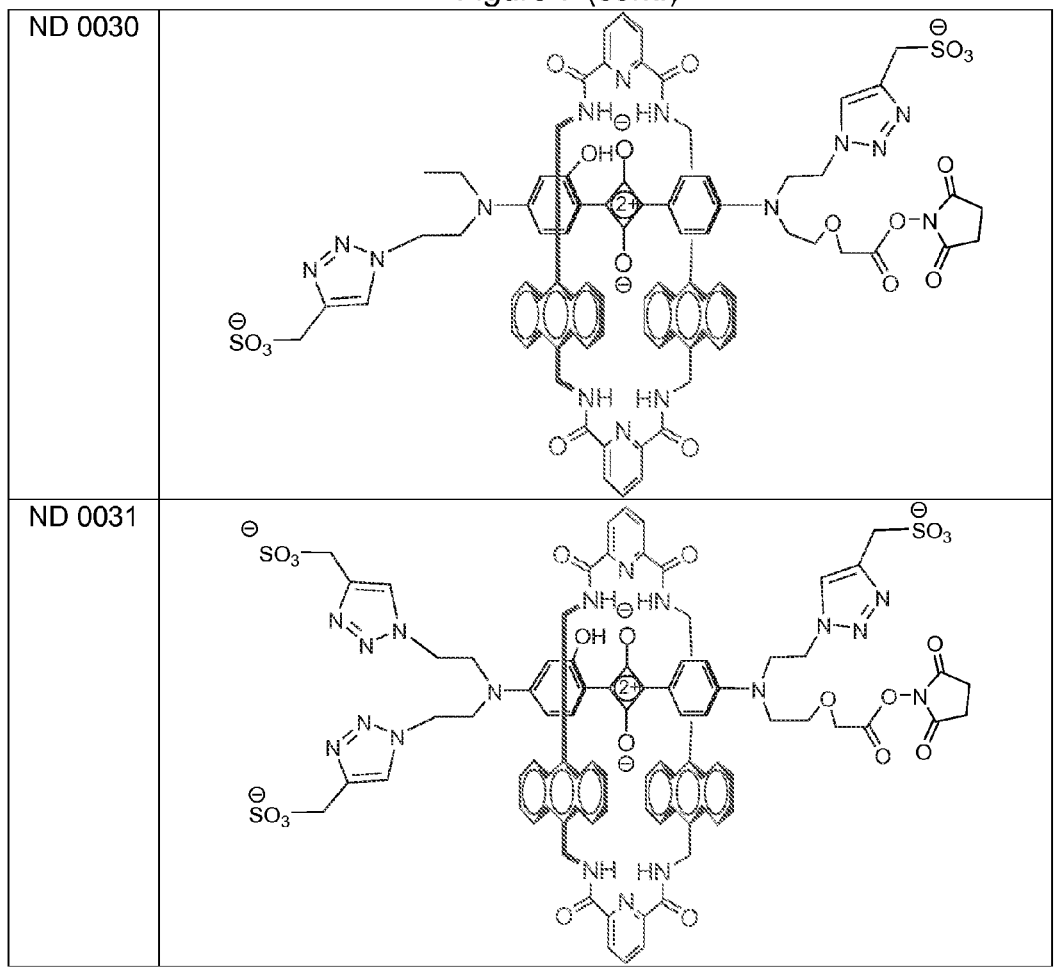
Figure 7:
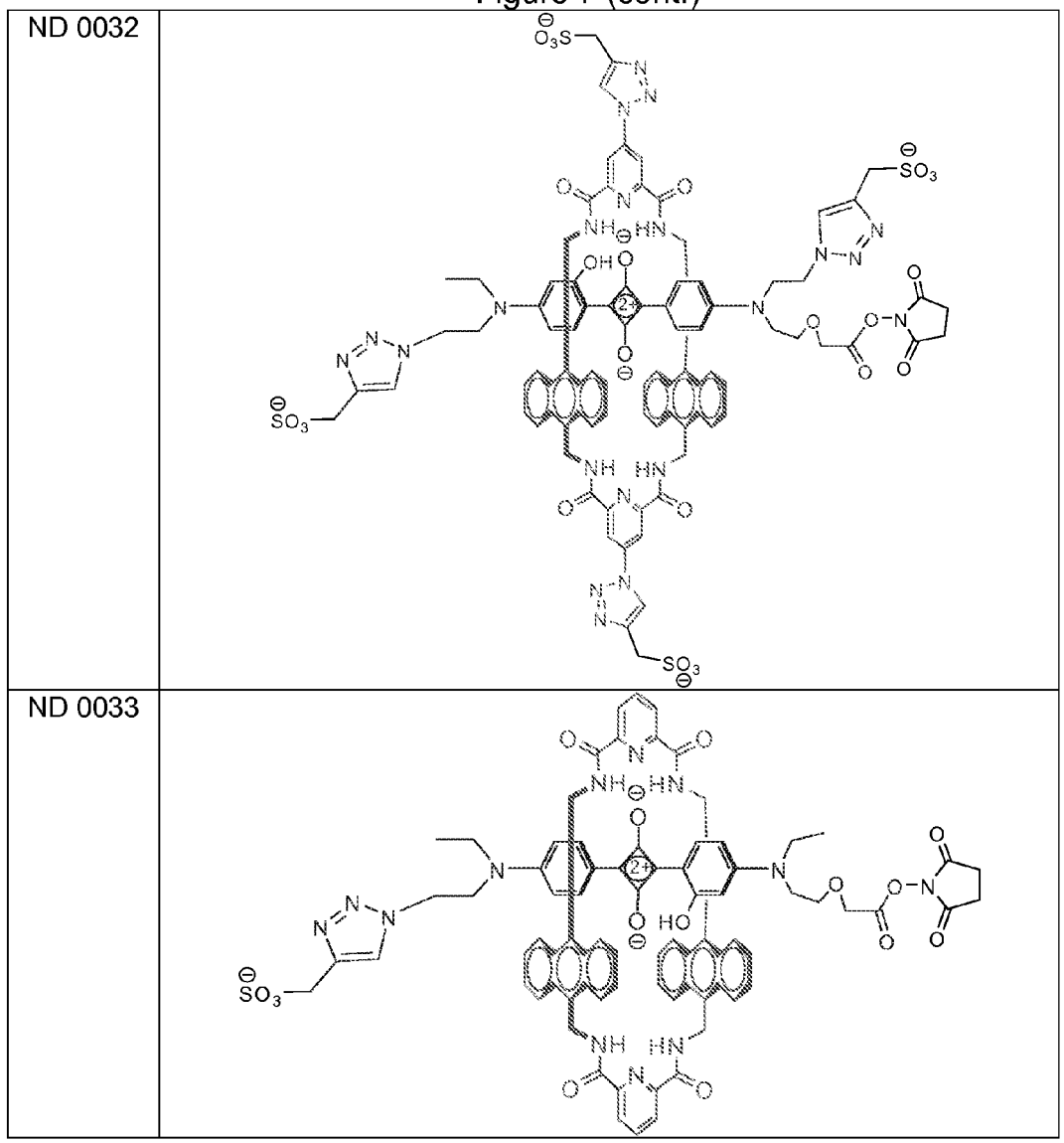
Figure 7:
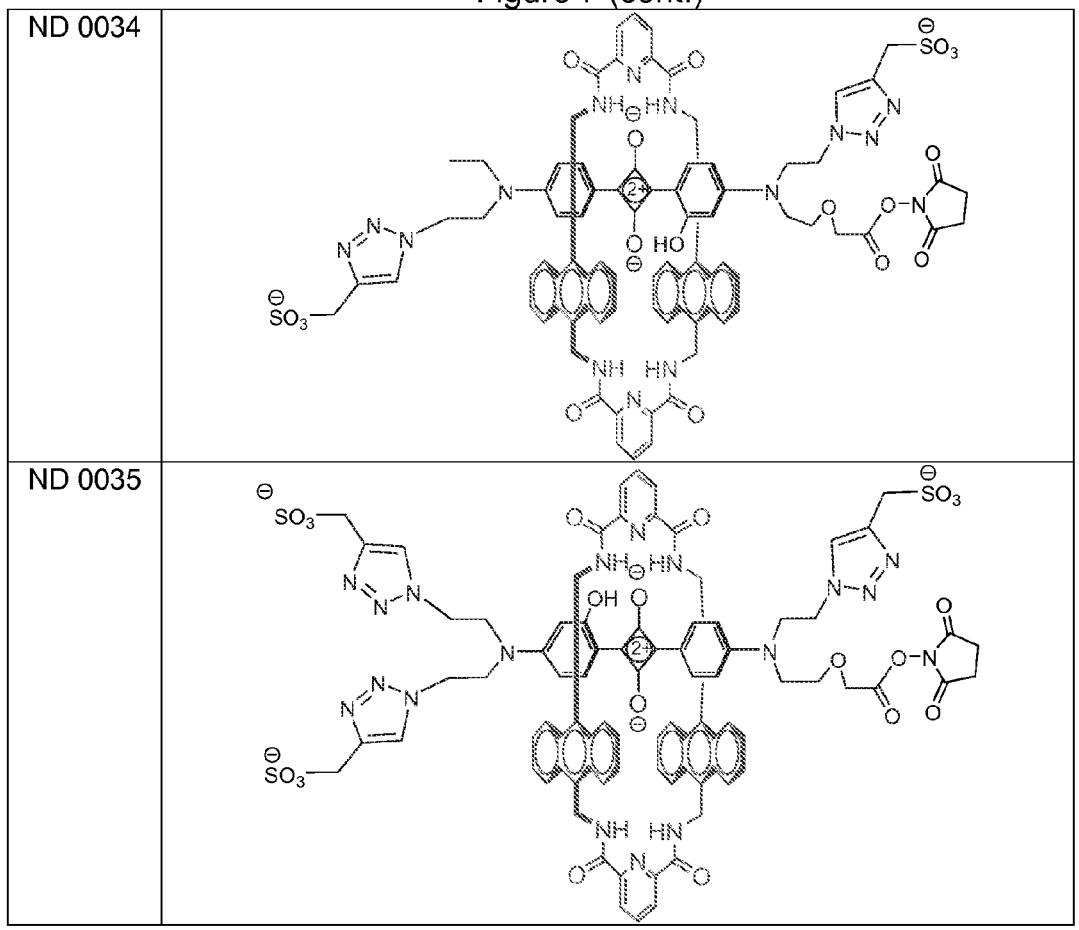
Figure 7:
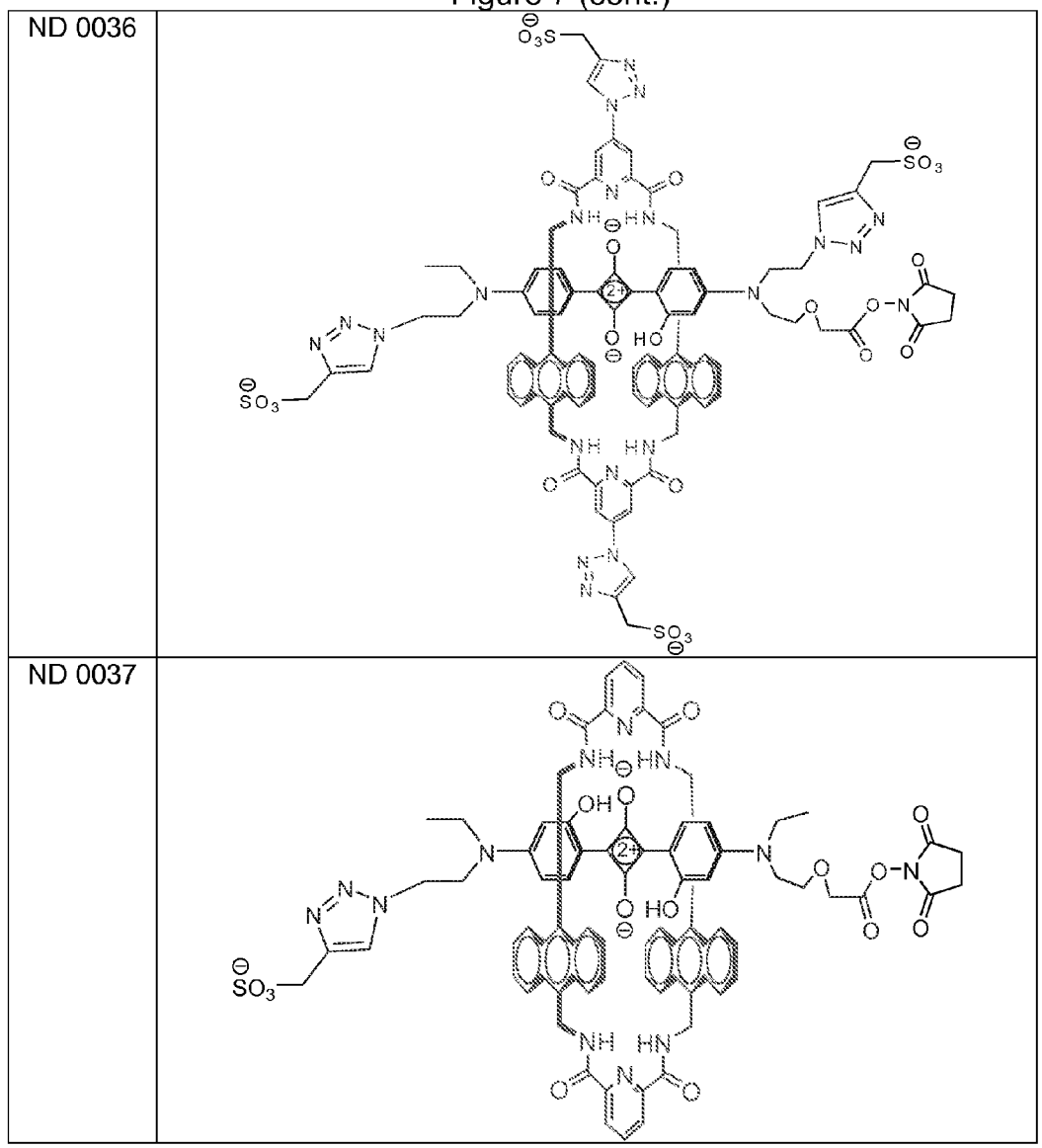
Figure 7:
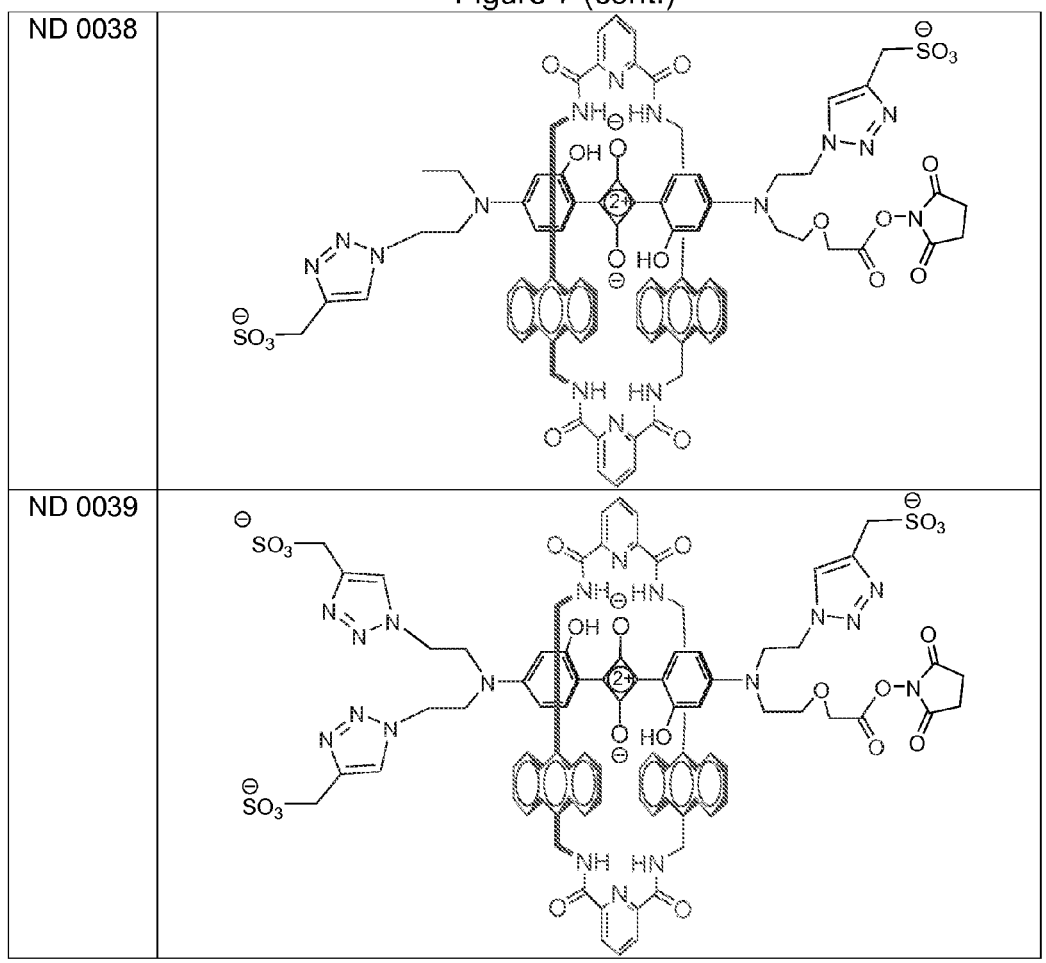
Figure 7:
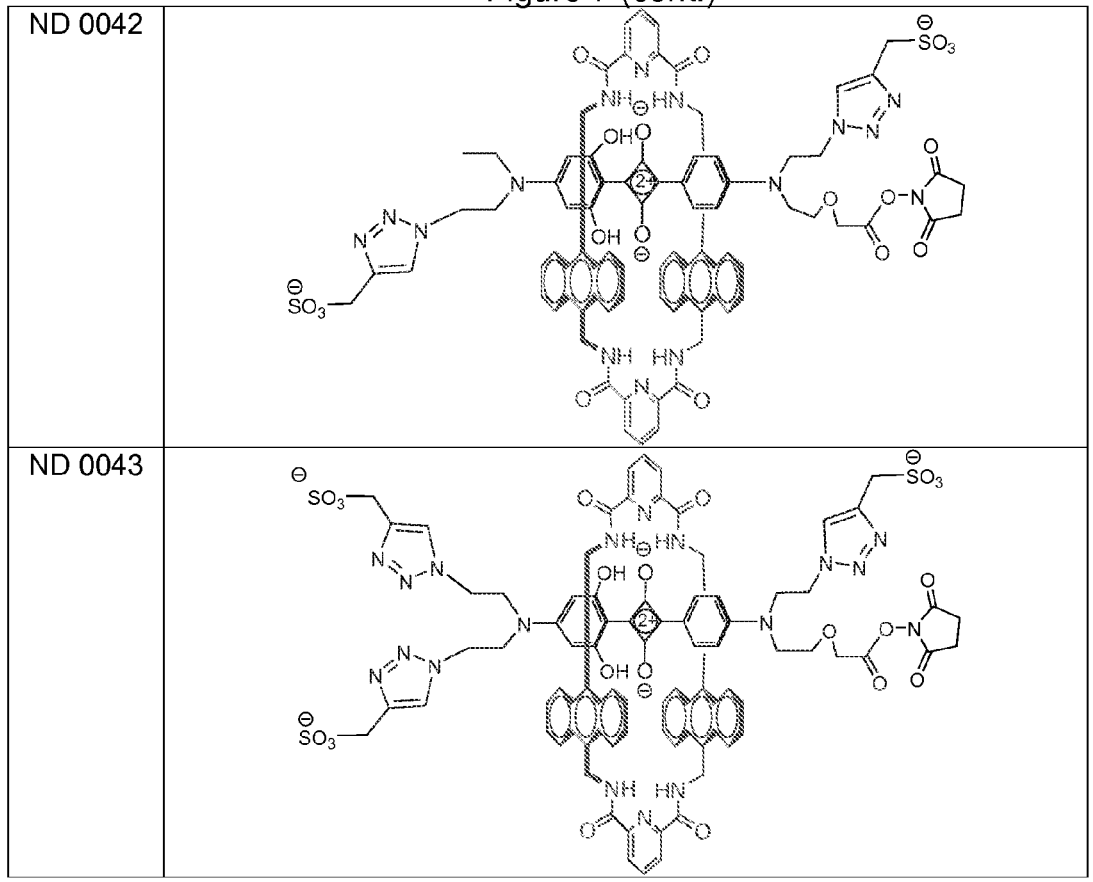
Figure 7:
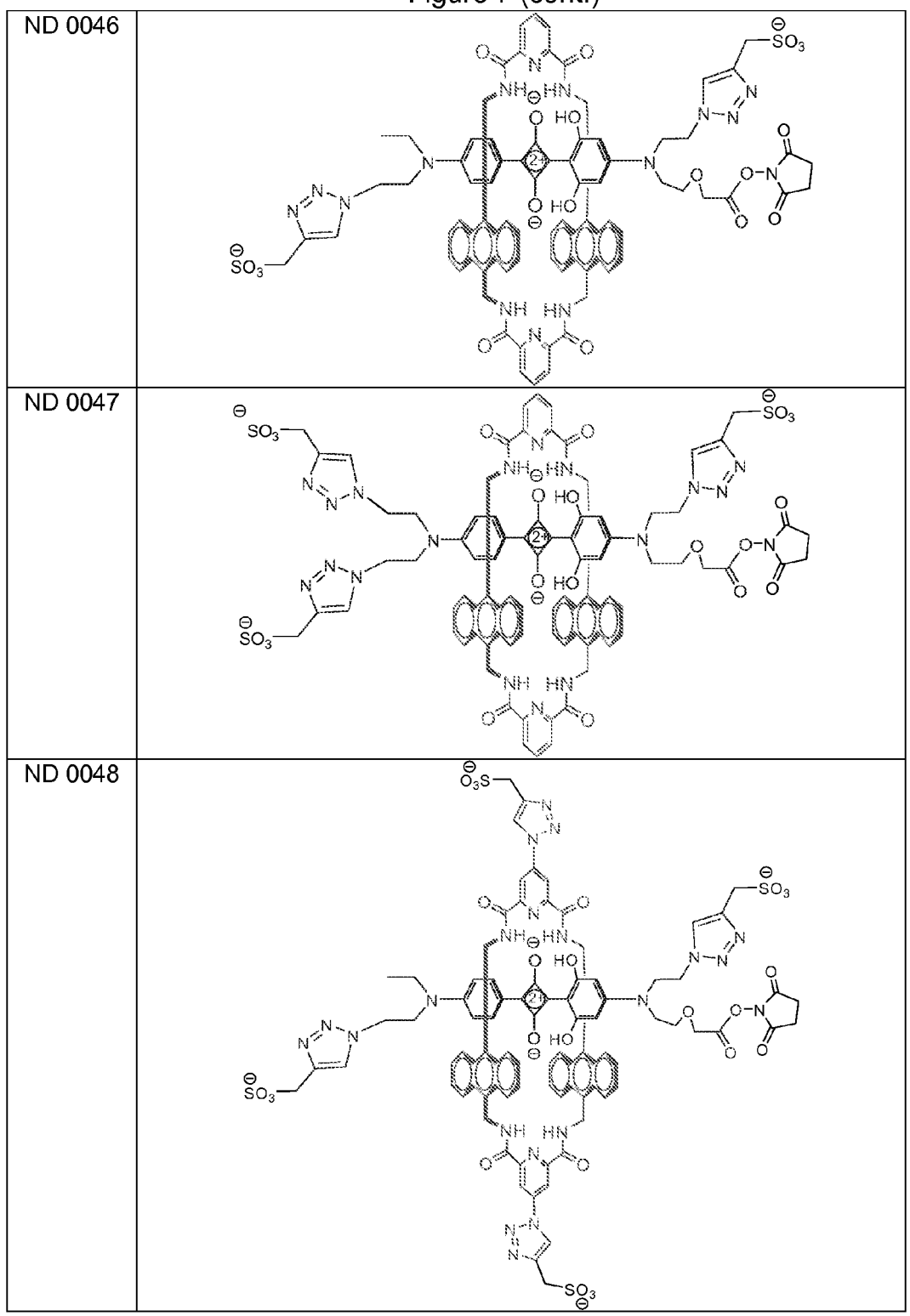

FIG. 7 illustrates a number of specific, non-limiting examples of squaraine rotaxanes.

1. Synthesis of Squaraine Rotaxanes with the Following General Structure (or a Pharmaceutically Acceptable Salt Thereof)

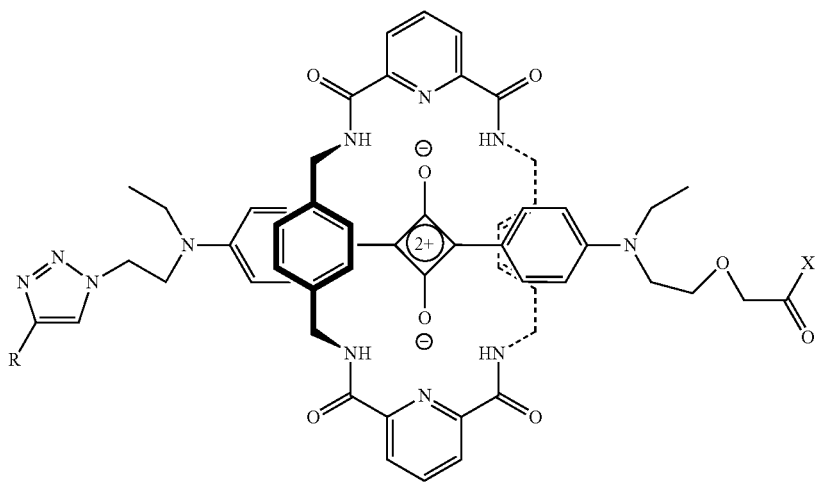

According to embodiments, X=OH, alkoxy, aryloxy, NH-alkyl, NH-aryl, N-succinimide, NH-alkyl-maleimide, NH-polyethylene glycol-biotin, polyethylene glycol, methylene-sulfonate, methylene-dimethylammonium-alkyl-sulfonate, methylene-phosphonate, or methylene-dimethylammonium-alkyl-phosphonate.

In one specific, non-limiting example, the synthesis of a typical example (below) from this series is as follows:

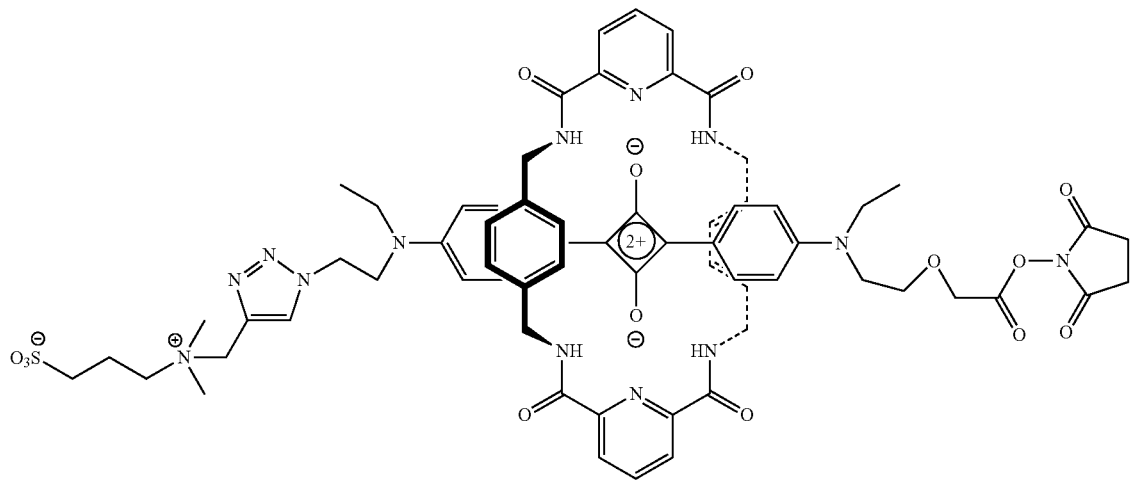

| 25 | 26 |
|---|---|
| (a) Synthesis of Semi Squaraine | (b) Synthesis of Aniline Derivative |

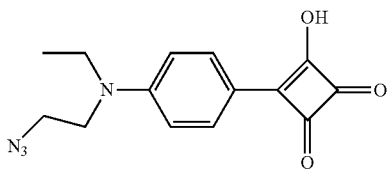

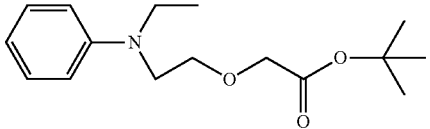

An azide derivative of aniline (1 mmol) is mixed with squaryl chloride (1.1 mmol) in dry benzene. The mixture is refluxed for 16 hours. Later, the benzene is evaporated to dryness and the crude product is treated with 50% acetic acid (30 mL) and 4N HCl (4 mL) and refluxed for 6 hours. The cooled reaction mixture is transferred to crushed ice. The precipitated product is washed with cold water to remove any presence of acid and dried under high vacuum.

N-(ethyl)-anilino ethanol (1 mmol) is mixed with tertiary butyl bromoacetate (1.1 mmol) in benzene. A 50% NaOH solution is added to the reaction along with tetrabutyl ammonium hydrogen sulfate (phase transfer agent). Stirring continues at room temperature for 3 hours. The organic layer is evaporated to dryness and the product is purified using silica gel chromatography using hexane:ethyl acetate (19:1).

(c) Synthesis of Squaraine Dye

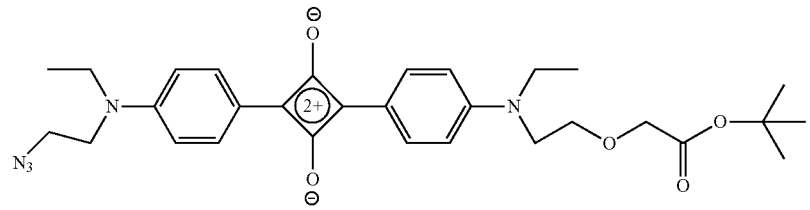

An aniline derivative (1 mmol) and semisquaraine (1.1 mmol) is mixed in anhydrous 2-propanol. To this mixture 1 mL of dehydrating agent tributylorthoformate is added. The reaction mixture is refluxed for 3 hours. After cooling, the solvents are evaporated to dryness. Silica gel chromatography in dichloromethane:methanol (97:3) gives the pure product.

(d) Synthesis of Squaraine Rotaxane

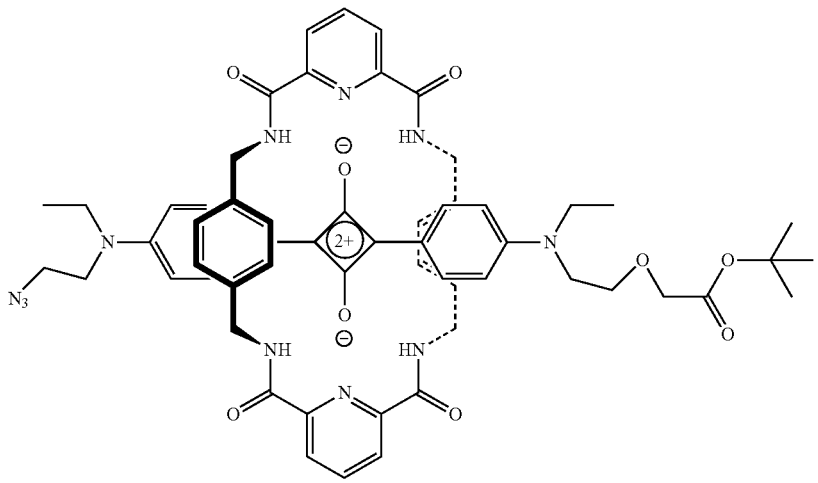

Clear solutions of the diacid dichloride (4 mmol) and p-xylylenediamine (4 mmol) in 5 mL chloroform are simultaneously added dropwise using a mechanical syringe pump apparatus over five hours to a stirred solution of squaraine dye (1 mmol) and triethylamine (4 mmol) in 40 mL of $CHCl_3$. After stirring overnight, the reaction mixture is filtered through a pad of celite to remove any polymeric material, and the resulting crude product chromatographed using a silica gel column and a mixture of methanol/chloroform (1/19) as eluent.

(e) Synthesis of Squaraine Rotaxane Carboxylic Acid

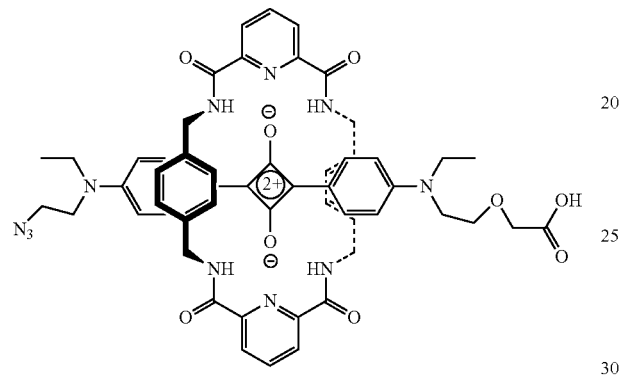

Trifluoroacetic acid (TFA; 1 mL) is added to a solution of squaraine rotaxane (0.1 mmol) in $CH_2Cl_2$ (5 mL). The mixture is stirred at room temperature for 6 hours, and the solvent and excess TFA evaporated under reduced pressure. The residue is washed with distilled water, and extracted with excess $CH_2Cl_2$. The organic layer is dried with $MgSO_4$, and the solvent is removed to afford azide-carboxylic acid rotaxane as a blue solid.

(f) Synthesis of Squaraine Rotaxane with Attached Zwitterionic Group

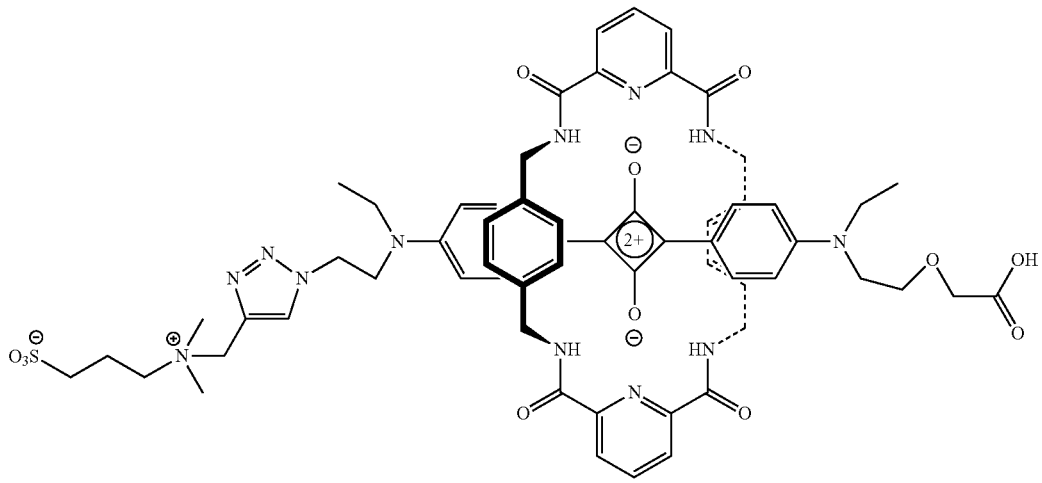

Azide squaraine rotaxane (0.1 mmol) is dissolved in a mixture of THF:t-butanol:water (10 mL each). Excess of alkyne reagent is added and a mixture of $CuSO_4 \cdot 5H_2O$ (75 mg in 2 mL $H_2O$) and sodium ascorbate (300 mg in 3 mL $H_2O$) are also added. The solution is stirred overnight and the product purified by reverse-phase chromatography.

(g) Synthesis of Zwitterionic Squaraine Rotaxane that is Activated for Bioconjugation

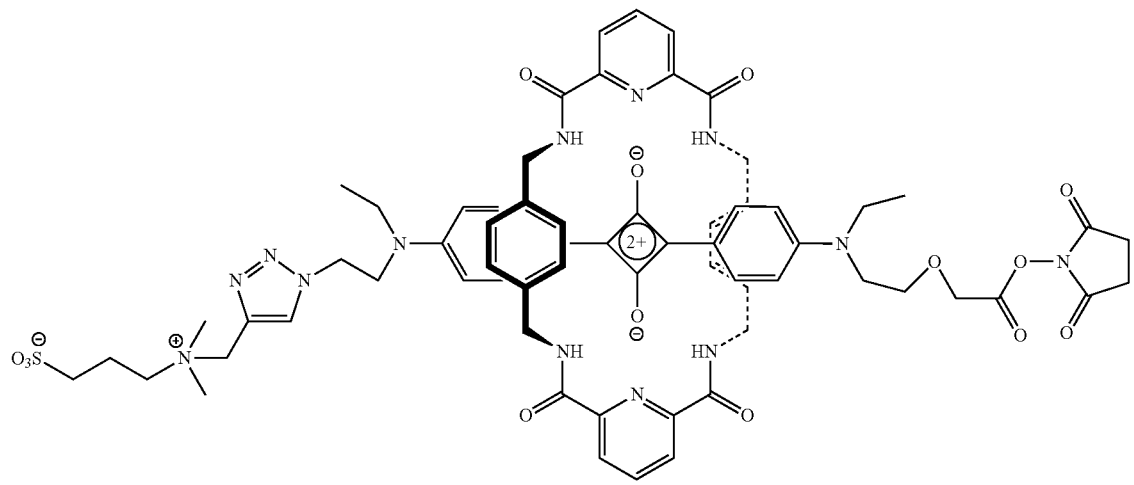

Zwitterionic squaraine rotaxane carboxylic acid (0.1 mmol) is dissolved in 2 mL dimethylformamide (DMF). O—(N-Succinimidyl)-1,1,3,3-tetramethyluronium tetrafluoroborate (TSTU) (1.1 eq) and diisopropylethylamine (1.1 eq) are added into the mixture and stirred overnight. Solvent is evaporated off and the crude product is washed with ether. The product is then dissolved in DMF and reprecipitated with ether, then dried under vacuum.

2. Synthesis of Squaraine Rotaxanes with the Following General Structure (or a Pharmaceutically Acceptable Salt Thereof)

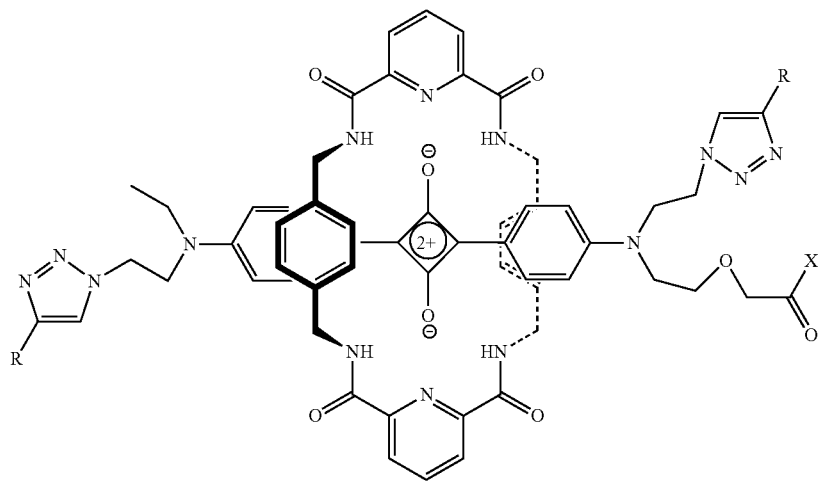

According to embodiments, X=OH, alkoxy, aryloxy, NH-alkyl, NH-aryl, N-succinimide, NH-alkyl-maleimide, NH-polyethylene glycol-biotin, polyethylene glycol, methylene-sulfonate, methylene-dimethylammonium-alkyl-sulfonate, methylene-phosphonate, or methylene-dimethylammonium-alkyl-phosphonate.

In one specific, non-limiting example, the synthesis of a typical example (below) from this series is as follows:

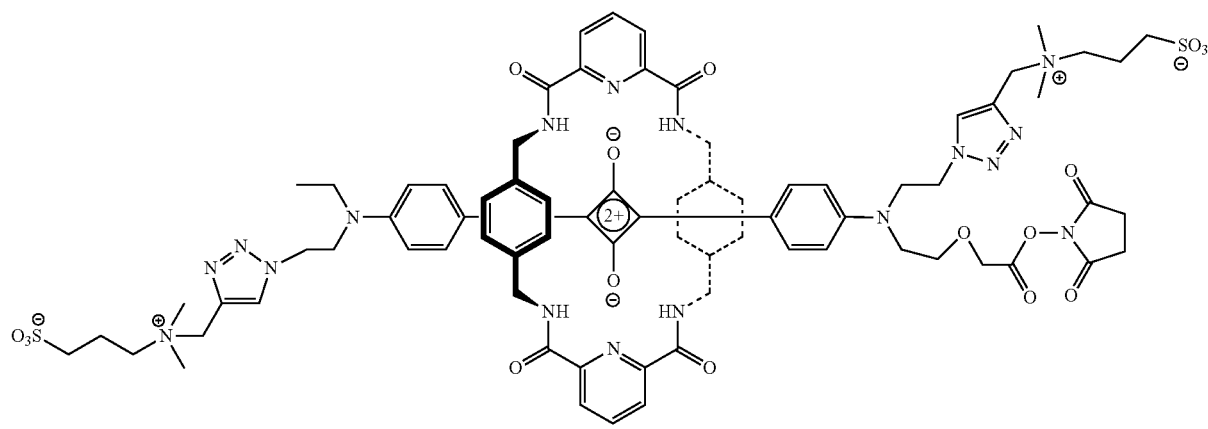

(a) Synthesis of Aniline Substituted Tert-Butyl Ester

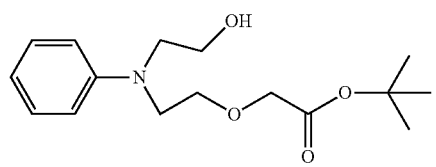

N-(diethanol) aniline (1 mmol) is mixed with tertiary butyl bromoacetate (1.1 mmol) in benzene. A 50% NaOH solution is made and added to the reaction along with tetrabutyl ammonium hydrogen sulfate (phase transfer agent). Stirring continued at room temperature for 3 hours. The organic layer is evaporated to dryness and the product purified using silica gel chromatography using hexane:ethyl acetate (9:1).

(b) Synthesis of Tosylate

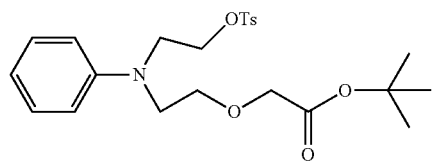

To a cooled solution of (1 mmol) in anhydrous pyridine (8 mmol) tosyl chloride (1.1 mmol) is added in small amounts. The solution is allowed to stir for 4 hours. Reaction mixture is quenched with 30% HCl (100 mL) and extracted with dichloromethane. The organic layer is evaporated to dryness.

(c) Synthesis of Azide

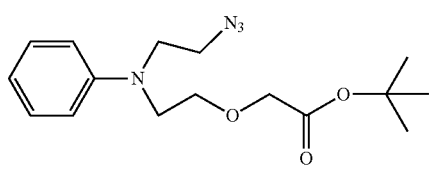

Tosylate is dissolved in DMF and treated with an excess of NaN$_3$. This is refluxed for 16 hours. The reaction mixture was filtered and the solution was evaporated to dryness. This is purified using column chromatography using hexane:ethyl acetate (49:1).

(d) Synthesis of Squaraine Dye

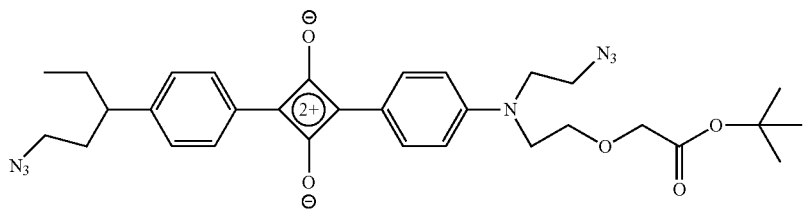

Aniline derivatve (1 mmol) and semisquaraine (1.1 mmol) are mixed in anhydrous 2-propanol. To this mixture 1 mL of dehydrating agent tributylorthoformate is added. The reaction mixture is refluxed for 3 hours. After cooling, the solvents are evaporated to dryness. Silica gel chromatography in dichloromethane:methanol (19:1) gives the pure product.

(e) Synthesis of Squaraine Rotaxane

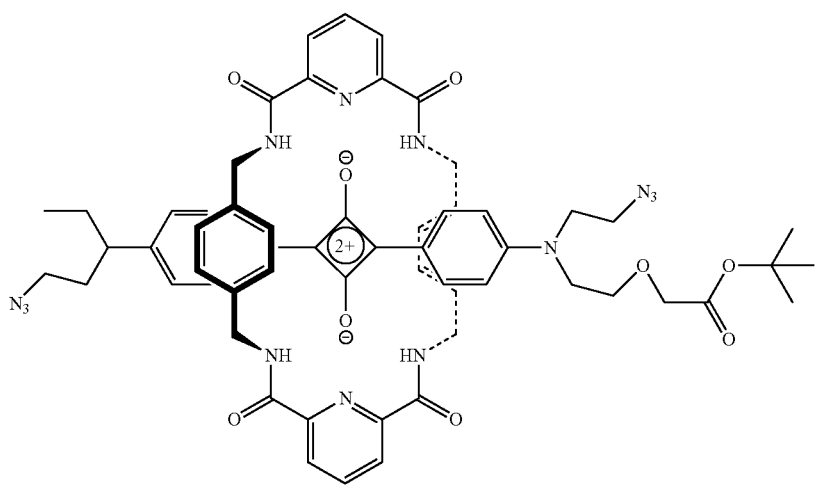

Clear solutions of the diacid dichloride (4 mmol) and p-xylenediamine (4 mmol) in 5 mL chloroform are simultaneously added dropwise using a mechanical syringe pump apparatus over five hours to a stirred solution of squaraine dye (1 mmol) and triethylamine (4 mmol) in 40 mL of $CHCl_3$. After stirring overnight, the reaction mixture is filtered through a pad of celite to remove any polymeric material, and the resulting crude product chromatographed using a silica gel column and a mixture of methanol/chloroform (1/19) as eluent.

(f) Synthesis of Squaraine Rotaxane Carboxylic Acid

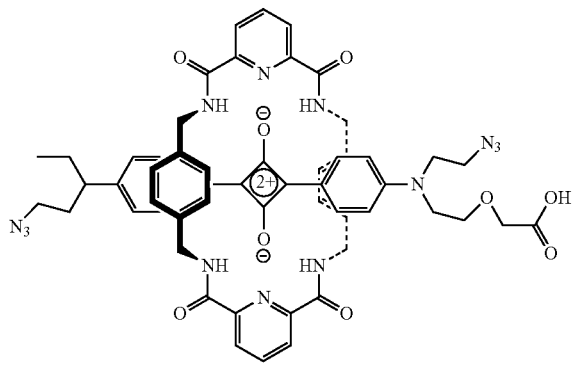

Trifluoroacetic acid (TFA; 1 mL) is added to a solution of rotaxane (0.1 mmol) in $CH_2Cl_2$ (5 mL). The mixture is stirred at room temperature for 6 hours, and the solvent and excess TFA evaporated under reduced pressure. The residue is washed with distilled water, and extracted with excess $CH_2Cl_2$. The organic layer is dried with $MgSO_4$ and the solvent removed to afford carboxylic acid rotaxane as a blue solid.

(g) Synthesis of Squaraine Rotaxane with Two Attached Zwitterionic Groups

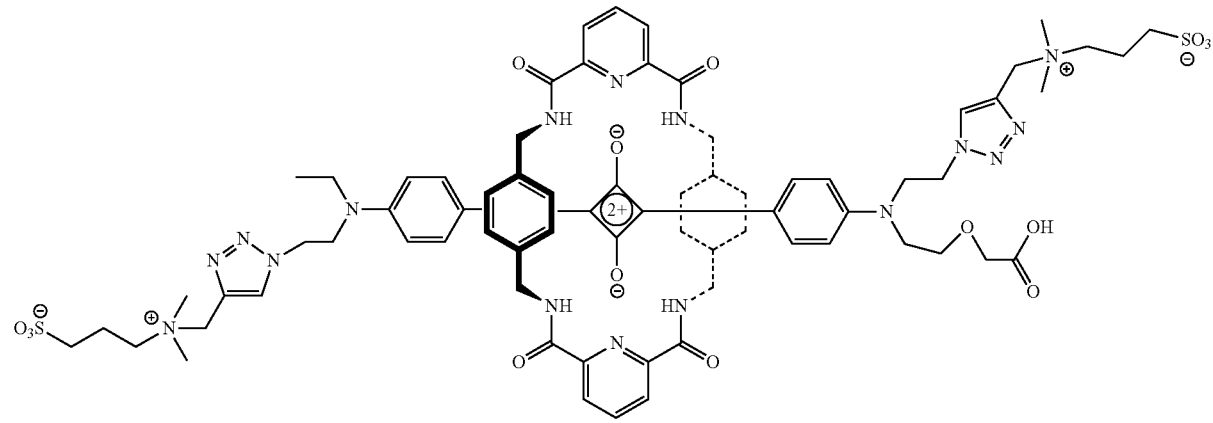

Squaraine rotaxane (0.1 mmol) is dissolved in a mixture of THF:t-butanol:water (10 mL each). Excess of alkyne reagent is added and a mixture of CuSO$_4$.5H$_2$O (75 mg in 2 mL H$_2$O) and sodium ascorbate (300 mg in 3 mL H$_2$O) is also added. The solution is stirred overnight. Purification in reverse phase column gives the pure product.

(h) Synthesis of Zwitterionic Squaraine Rotaxane that is Activated for Bioconjugation

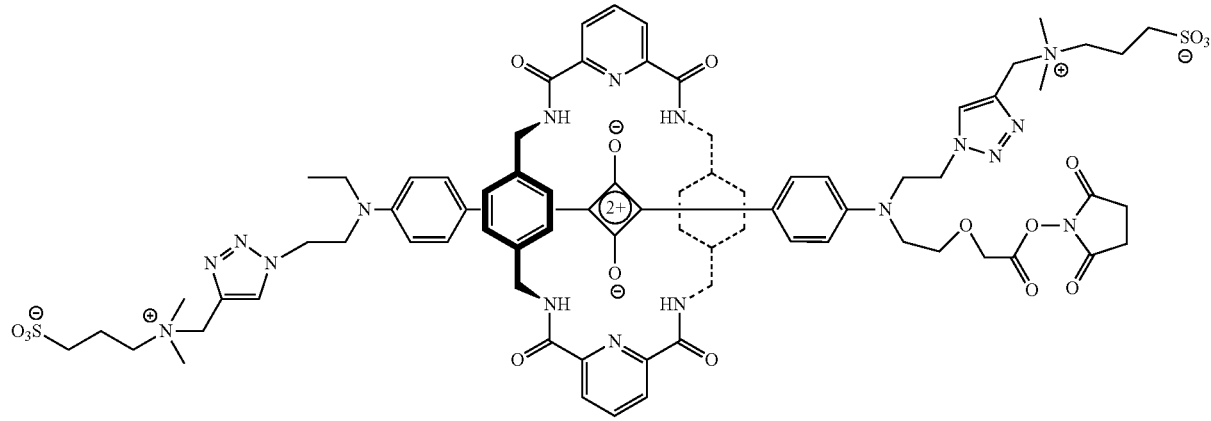

Zwitterionic squaraine rotaxane carboxylic acid (0.1 mmol) is dissolved in 2 mL DMF. TSTU (1.1 eq) and diisopropylethylamine (1.1 eq) are added into the mixture and stirred overnight. Solvent is evaporated off and the crude product is washed with ether. The product is then dissolved in DMF and reprecipitated with ether, and dried under vacuum.

3. Synthesis of Squaraine Rotaxanes with the Following General Structure (or a Pharmaceutically Acceptable Salt Thereof)

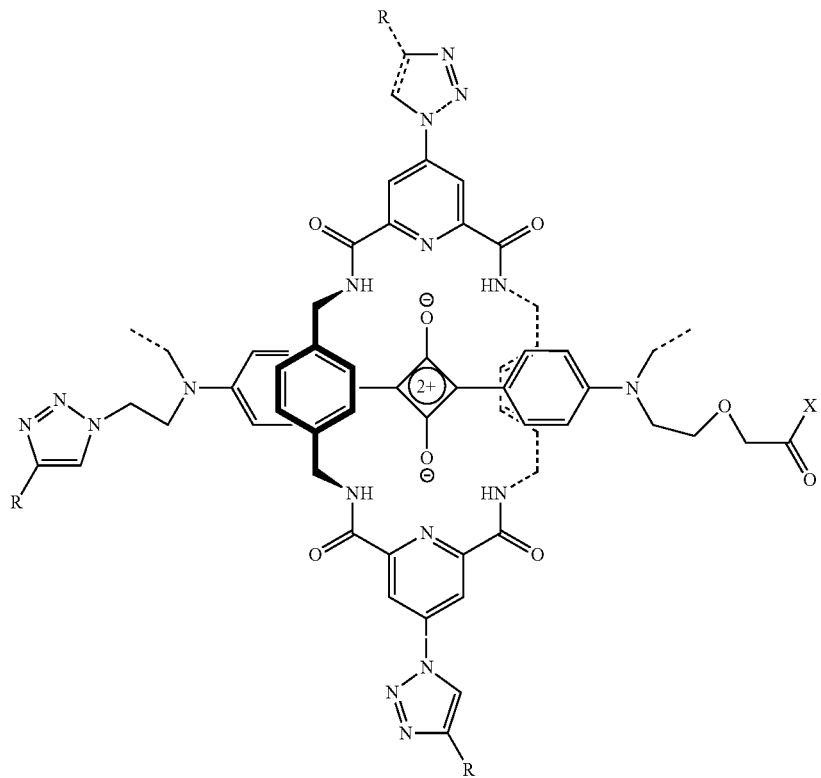

According to embodiments, X=OH, alkoxy, aryloxy, NH-alkyl, NH-aryl, N-succinimide, NH-alkyl-maleimide, NH-polyethylene glycol-biotin, polyethylene glycol, methylene-sulfonate, methylene-dimethylammonium-alkyl-sulfonate, methylene-phosphonate, or methylene-dimethylammonium-alkyl-phosphonate.

In one specific, non-limiting example, the synthesis of a typical example (below) from this series is as follows:

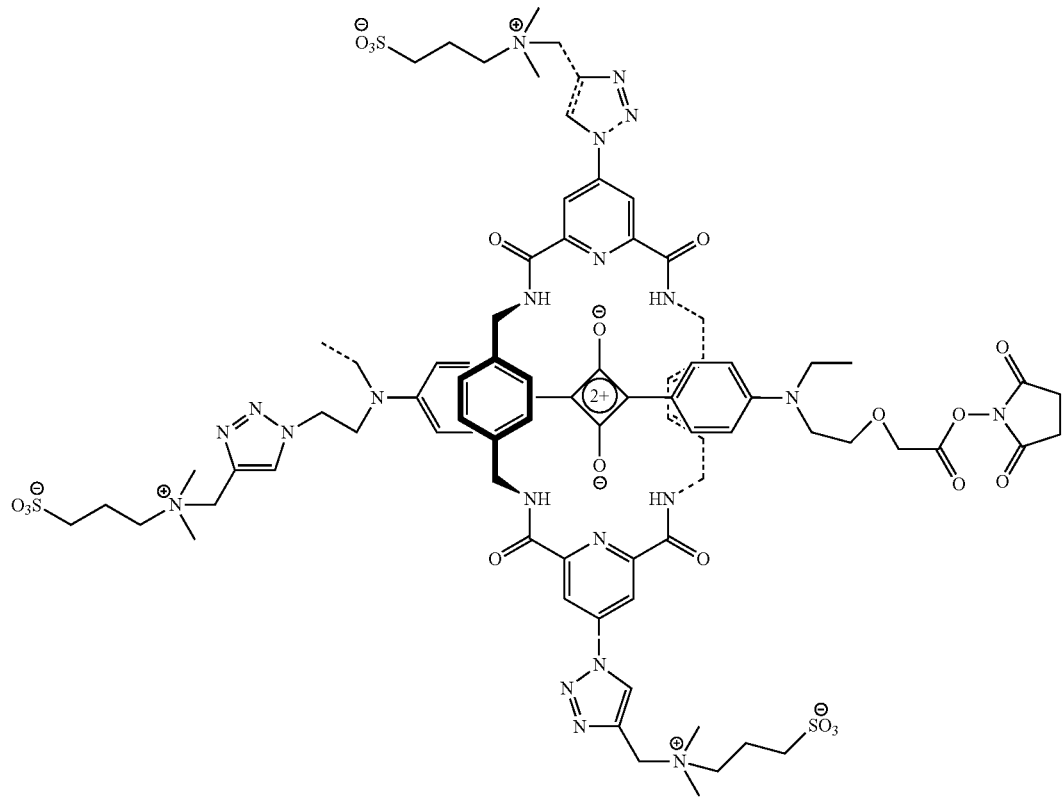

(a) Synthesis of 4-azidopyridine-2,6-diacid dichloride

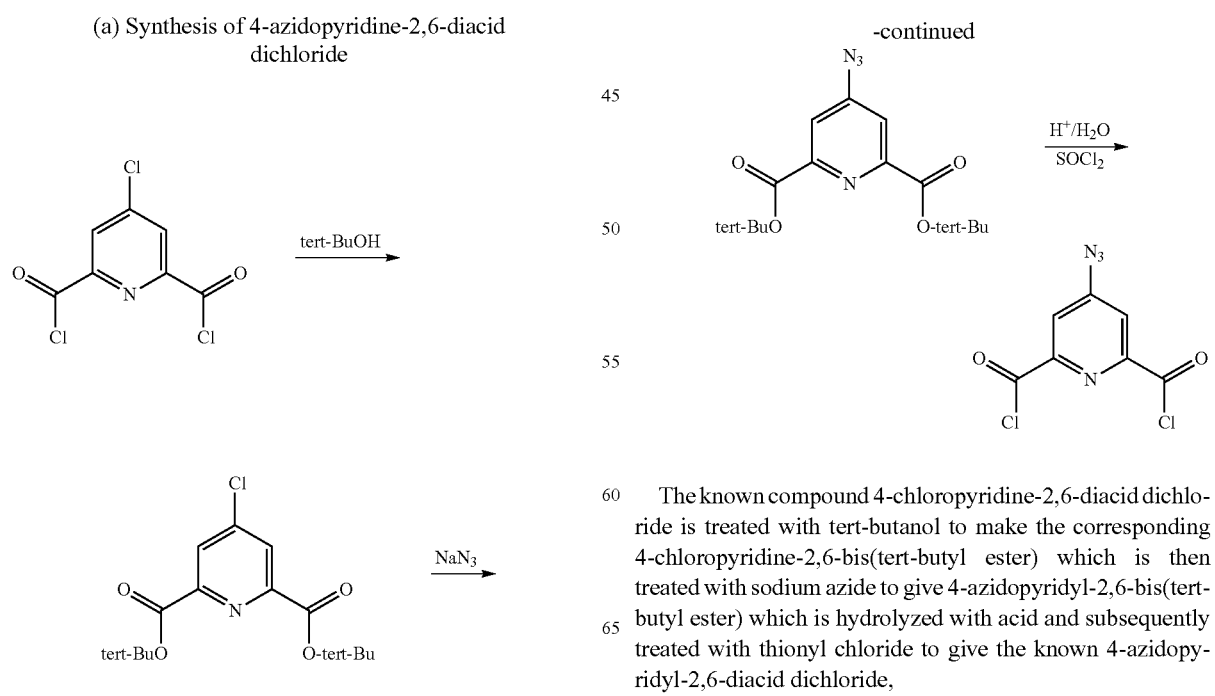

The known compound 4-chloropyridine-2,6-diacid dichloride is treated with tert-butanol to make the corresponding 4-chloropyridine-2,6-bis(tert-butyl ester) which is then treated with sodium azide to give 4-azidopyridyl-2,6-bis(tert-butyl ester) which is hydrolyzed with acid and subsequently treated with thionyl chloride to give the known 4-azidopyridyl-2,6-diacid dichloride, (b) Synthesis of Squaraine Rotaxane

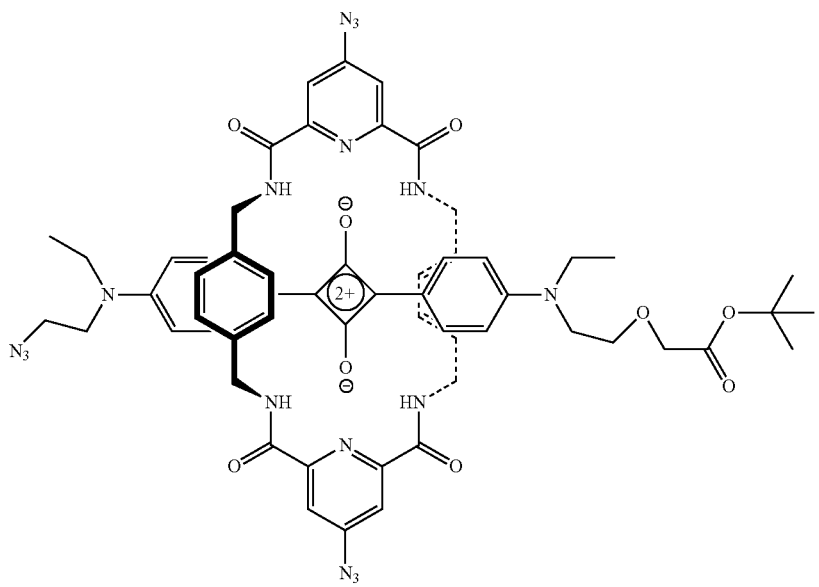

Clear solutions of the 4-azidopyridyl-2,6-diacid dichloride (4 mmol) and p-xylylenediamine (4 mmol) in 5 mL chloroform are simultaneously added dropwise using a mechanical syringe pump apparatus over five hours to a stirred solution of squaraine dye (1 mmol) and triethylamine (4 mmol) in 40 mL of $CHCl_3$. After stirring overnight, the reaction mixture is filtered through a pad of celite to remove any polymeric material, and the resulting crude product was chromatographed using a silica gel column and a mixture of methanol/chloroform (1/19) as eluent.

(c) Synthesis of Squaraine Rotaxane Carboxylic Acid

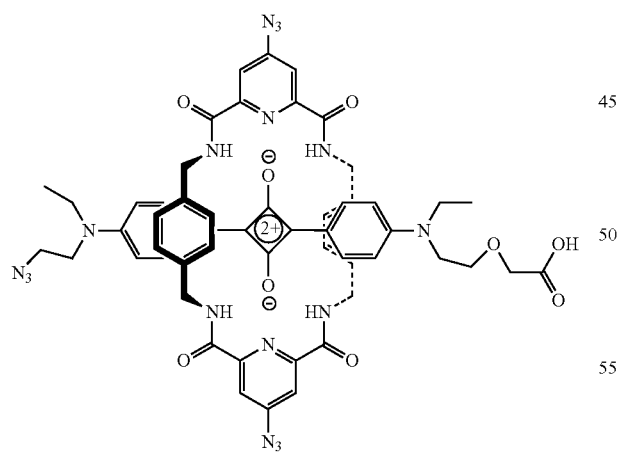

Trifluoroacetic acid (1 mL) is added to a solution of azide squaraine rotaxane (0.1 mmol) in $CH_2Cl_2$ (5 mL). The mixture is stirred at room temperature for 6 hours, and the solvent and excess TFA are evaporated under reduced pressure. The residue is washed with distilled water, and extracted with excess $CH_2Cl_2$. The organic layer is dried with $MgSO_4$ and the solvent removed to afford carboxylic acid rotaxane as a blue solid.

(d) Synthesis of Squaraine Rotaxane with Three Attached Zwitterionic Groups

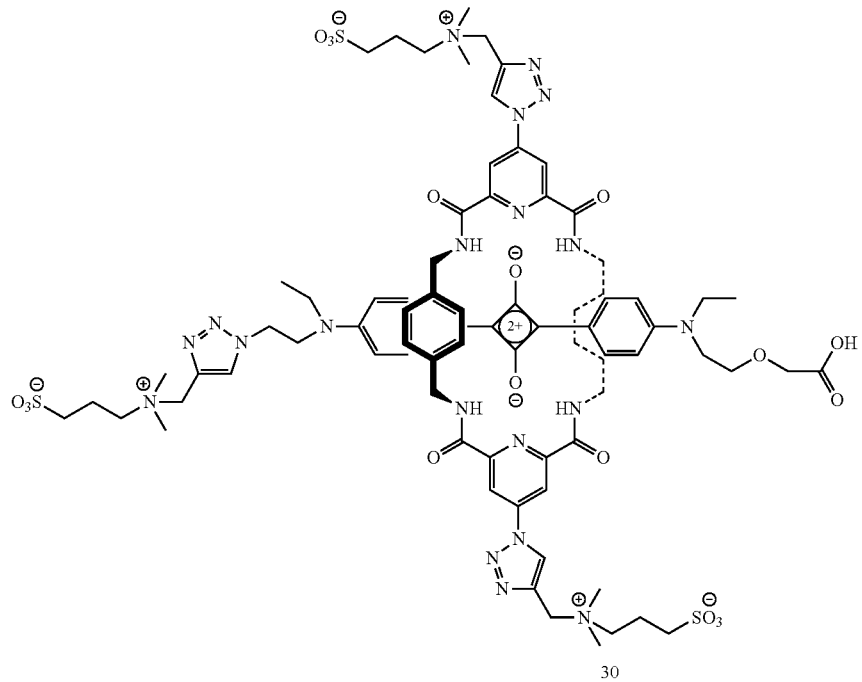

Azide squaraine rotaxane (0.1 mmol) is dissolved in a mixture of THF:t-butanol:water (10 mL each). Excess of alkyne reagent is added and a mixture of $CuSO_4 \cdot 5H_2O$ (75 mg in 1 mL $H_2O$) and sodium ascorbate (300 mg in 3 mL $H_2O$) is also added. The solution is stirred overnight. Purification in reverse phase column gives the pure product.

(e) Synthesis of Zwitterionic Squaraine Rotaxane that is Activated for Bioconjugation

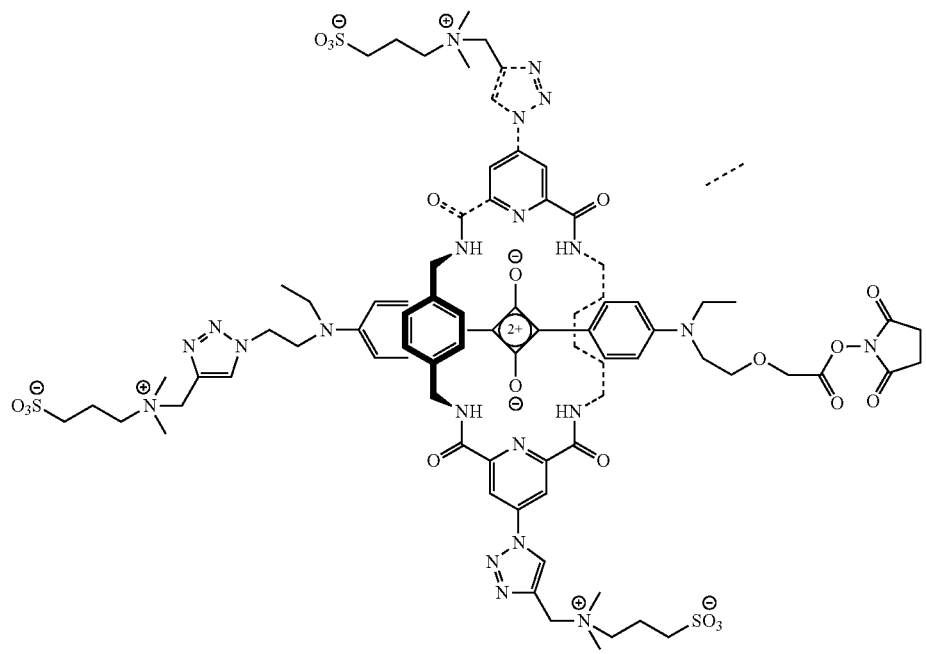

Zwitterionic squaraine rotaxane carboxylic acid (0.1 mmol) is dissolved 2 mL DMF. TSTU (1.1 eq) and diisopropylethylamine (1.1 eq) are added into the mixture and stirred overnight. Solvent is evaporated and the crude product is washed with ether. The product is then dissolved in DMF and reprecipitated with ether, then dried under vacuum.

4. Synthesis of Squaraine Rotaxanes with the Following General Structure (or a Pharmaceutically Acceptable Salt Thereof)

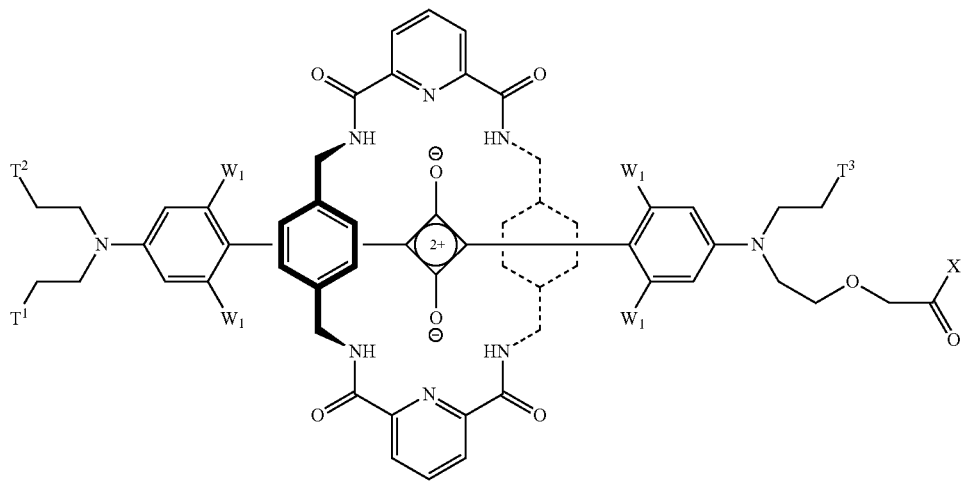

where $T^1$, $T^2$, $T^3$, $T^4$, and $T^5$ are each independently H or 1,3-triazole rings; and $W^1$, $W^2$, $W^3$, and $W^4$ are each independently H or OH In one specific, non-limiting example, the synthesis of a typical intermediate in this series is as follows:

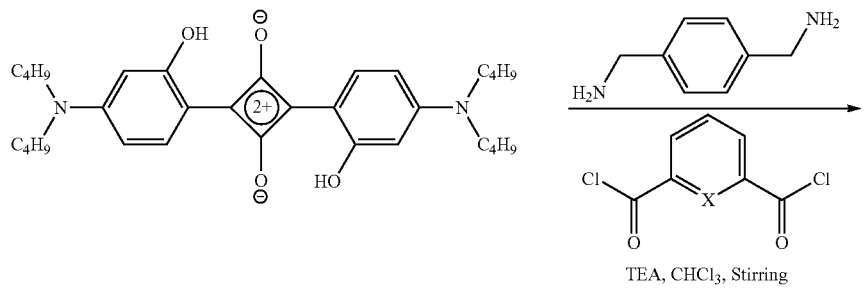

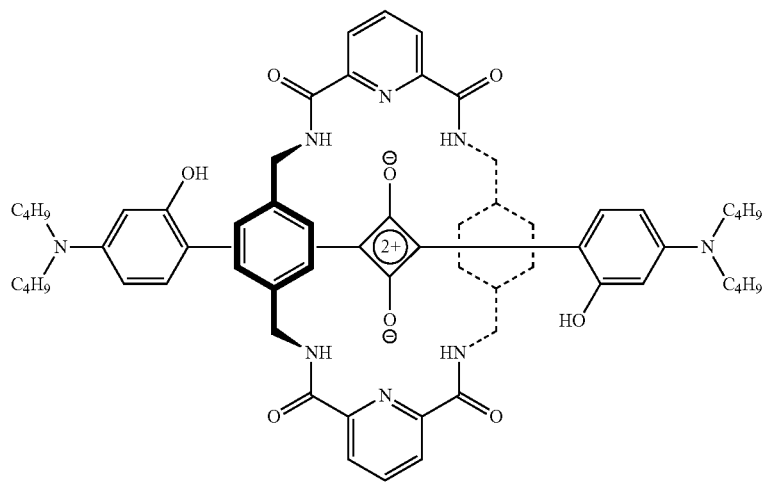

Clear solutions of the pyridine-2,6-dicarbonyl dichloride (1.92 mmol) and 1,4-xylylenediamine (1.92 mmol) in anhydrous chloroform (30 mL) are added dropwise over 5 hours, using a mechanical syringe pump, to a stirred solution containing the squaraine dye (0.38 mmol) and triethylamine (4.42 mmol) in anhydrous chloroform (150 mL). After stirring overnight, the reaction is filtered through a pad of Celite to remove any polymeric material. The solvent is removed by rotary evaporation, and the crude product purified by column chromatography using a column of silica gel with MeOH/CHCl$_3$ (1:19).

In one specific, non-limiting example, the synthesis of a typical example in this series is as follows:

(a) Rotaxane Synthesis

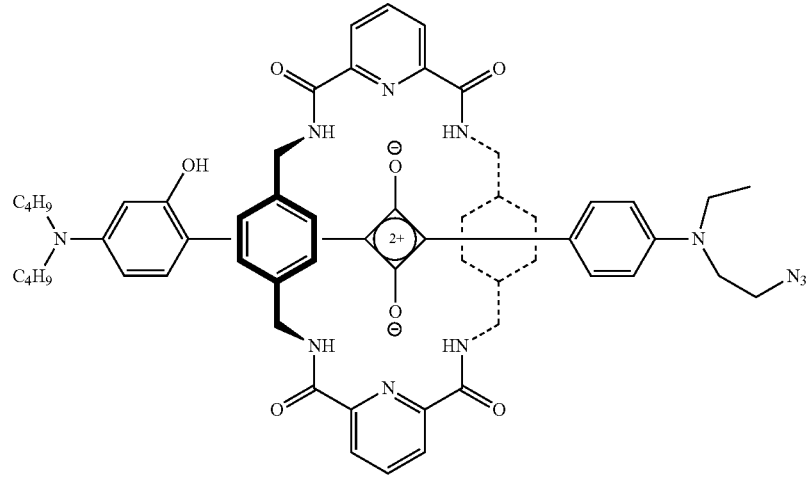

Clear solutions of the pyridine-2,6-dicarbonyl dichloride (2 mmol) and 1,4-xylylenediamine (2 mmol) in anhydrous chloroform (30 mL) are added dropwise over 5 hours, using a mechanical syringe pump, to a stirred solution containing the squaraine dye (0.4 mmol) and triethylamine (4 mmol) in anhydrous chloroform (150 mL). After stirring overnight, the reaction is filtered through a pad of Celite to remove any polymeric material. The solvent is removed by rotary evaporation, and the crude product purified by column chromatography using a column of silica gel.

(b) Attachment of Zwitterionic Group

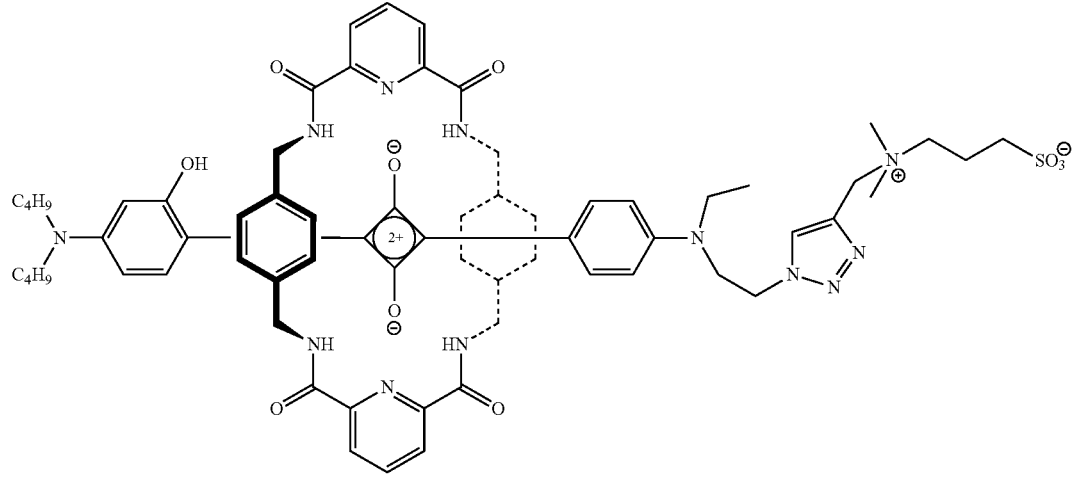

Azide squaraine rotaxane (0.1 mmol) is dissolved in a mixture of THF:t-butanol:water (10 mL each). Excess of alkyne reagent is added and a mixture of CuSO$_4$.5H$_2$O (75 mg in 1 mL H$_2$O) and sodium ascorbate (300 mg in 3 mL H$_2$O) is also added. The solution is stirred overnight. Purification in reverse phase column gives the pure product.

In one specific, non-limiting example, the synthesis of a typical intermediate in this series is as follows:

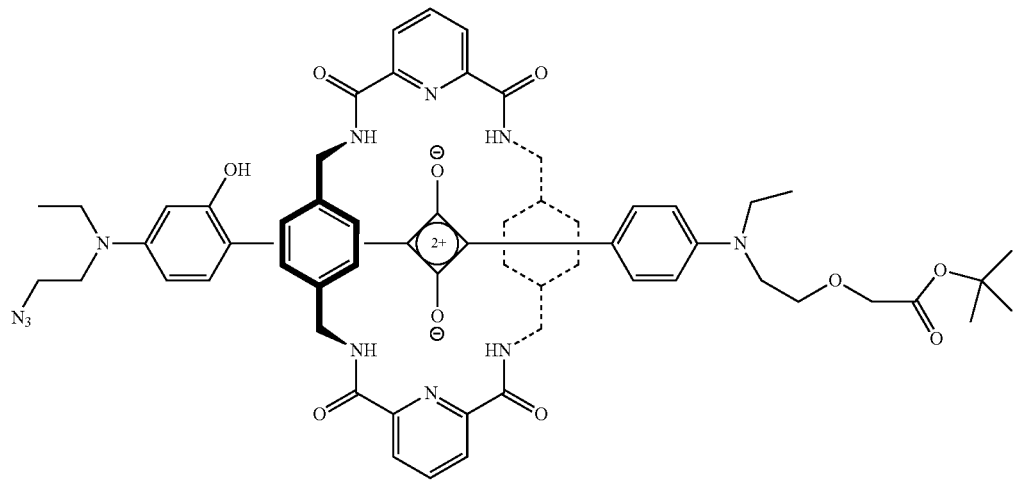

Clear solutions of the pyridine-2,6-dicarbonyl dichloride (2 mmol) and 1,4-xylylenediamine (2 mmol) in anhydrous chloroform (30 mL) are added dropwise over 5 hours, using a mechanical syringe pump, to a stirred solution containing the squaraine dye (0.4 mmol) and triethylamine (4 mmol) in anhydrous chloroform (150 mL). After stirring overnight, the reaction is filtered through a pad of Celite to remove any polymeric material. The solvent is removed by rotary evaporation, and the crude product purified by column chromatography using a column of silica gel.

In one specific, non-limiting example, the synthesis of a typical intermediate in this series is as follows:

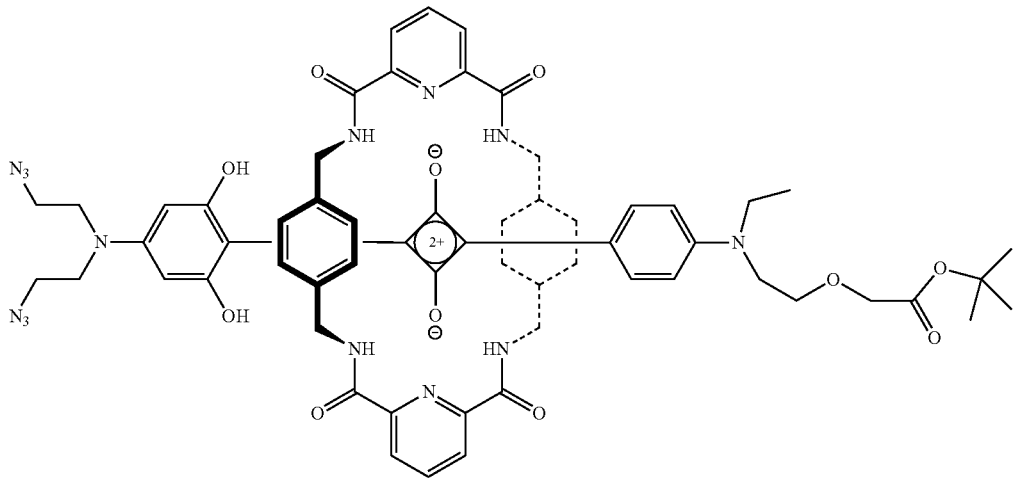

Clear solutions of the pyridine-2,6-dicarbonyl dichloride (2 mmol) and 1,4-xylylenediamine (2 mmol) in anhydrous chloroform (30 mL) are added dropwise over 5 hours, using a mechanical syringe pump, to a stirred solution containing the squaraine dye (0.4 mmol) and triethylamine (4 mmol) in anhydrous chloroform (150 mL). After stirring overnight, the reaction is filtered through a pad of Celite to remove any polymeric material. The solvent is removed by rotary evaporation, and the crude product purified by column chromatography using a column of silica gel.

5. Synthesis of Squaraine Rotaxanes with the Following General Structure (or a Pharmaceutically Acceptable Salt Thereof)

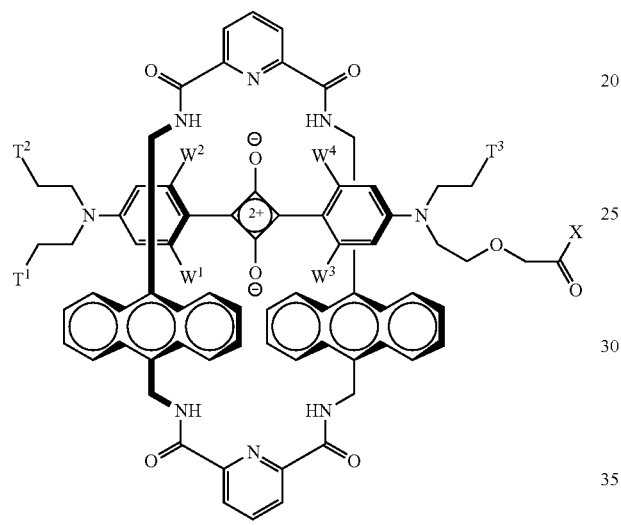

where $T^1$, $T^2$, $T^3$, $T^4$, $T^5$ are each independently H or a 1,3-triazole rings, and $W^1$, $W^2$, $W^3$, and $W^4$ are each independently H or OH In one specific, non-limiting example, the synthesis of a typical intermediate in this series is as follows:

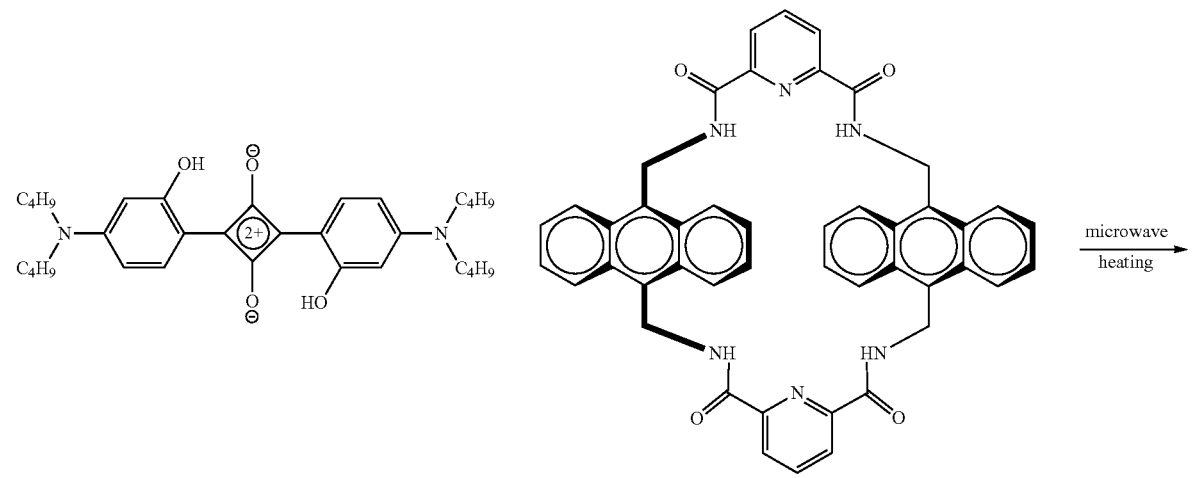

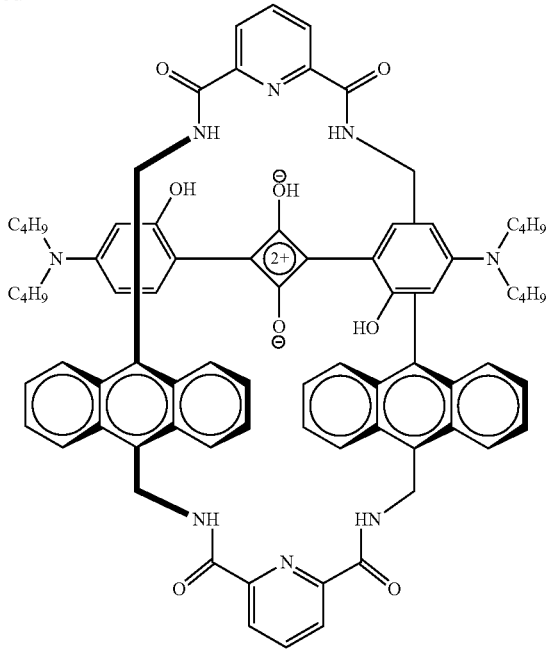
The pyridyl anthracene macrocycle (10 mmol) is mixed with the squaraine dye (10 mmol) in chloroform (19 mL) and the solution heated to 160° C. using a microwave oven. After 5 minutes the desired squaraien rotaxane is obtained after removal of the solvent and chromatography.
In one specific, non-limiting example, the synthesis of a typical intermediate in this series is as follows:
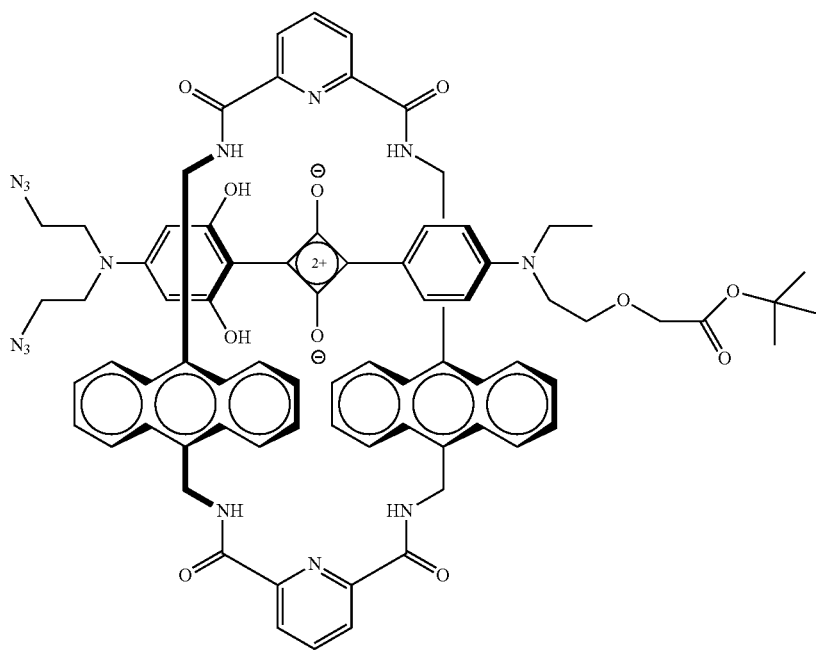

The pyridyl anthracene macrocycle (10 mmol) is mixed with the squaraine dye (10 mmol) in chloroform (19 mL) and the solution heated to 160° C. using a microwave oven. After 5 minutes the desired squaraien rotaxane is obtained after removal of the solvent and chromatography.

In one specific, non-limiting example, the synthesis of a typical intermediate in this series is as follows:

(a) Rotaxane Synthesis

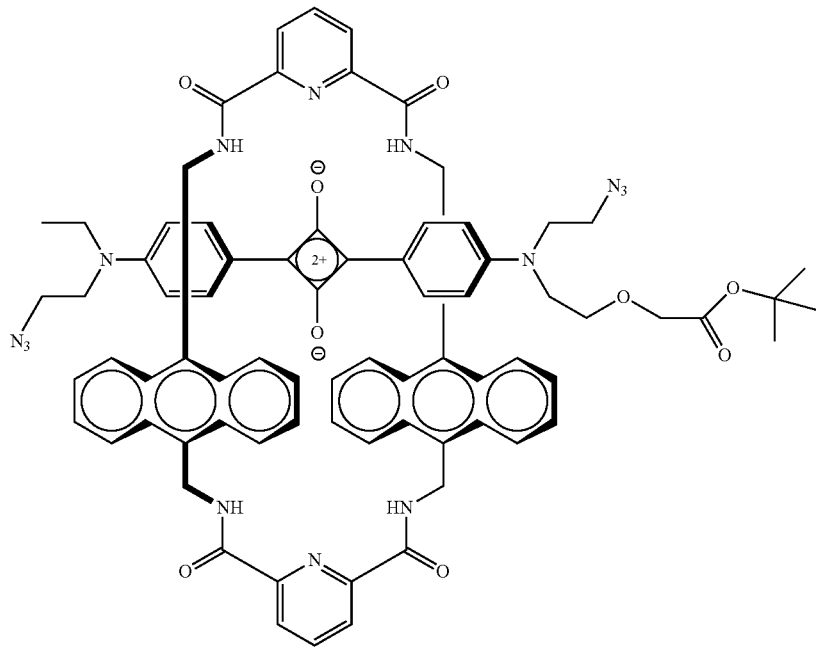

The pyridyl anthracene macrocycle (10 mmol) is mixed with the squaraine dye (10 mmol) in chloroform (19 mL) and the solution heated to 160° C. using a microwave oven. After 5 minutes the desired squaraine rotaxane is obtained in quantitative yield.

(b) Attachment of Zwitterionic Groups

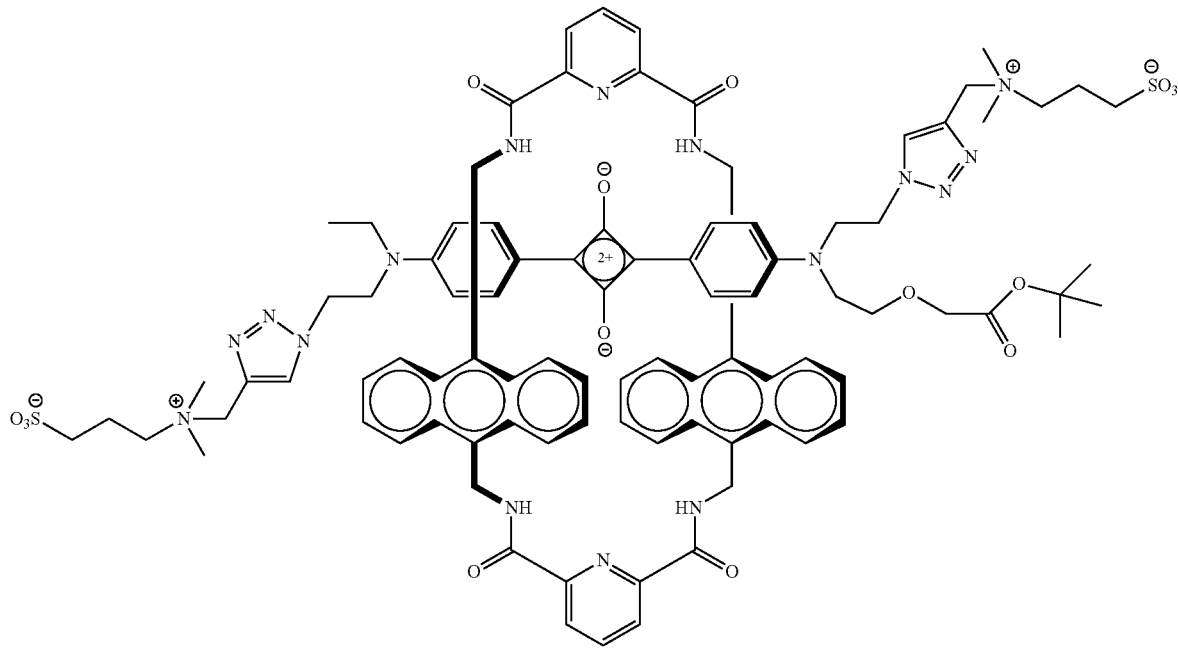

Azide squaraine rotaxane (0.1 mmol) is dissolved in a mixture of THF:t-butanol:water (10 mL each). Excess of alkyne reagent is added and a mixture of CuSO$_4$.5H$_2$O (75 mg in 1 mL H$_2$O) and sodium ascorbate (300 mg in 3 mL H$_2$O) is also added. The solution is stirred overnight. Purification in a reverse phase column gives the pure product.

Cell Labeling

Fluorescent dyes are often used to covalently label cells and allow studies of cell motility, proliferation, and migration.

Cells are washed and resuspended in 0.1% (bovine serum albumin) BSA/PBS to a concentration of 10$^7$ cells/mL. Labeling with squaraine rotaxane N-hydroxysuccinimde ester is performed by adding an aliquot of the squaraine rotaxane N-hydroxysuccinimde ester (50 mM stock in DSMO) to a give a final concentration of 0.5 µM, and incubating the cells for 30 minutes at 37° C. The cells are washed extensively and resuspended in the appropriate buffer for microscopic studies. The cells are imaged by confocal microscopy using a Cy-5 filter set.

Protein Labeling

Fluorescent dyes are often used to covalently label proteins, especially antibodies, and allow detection assays for various applications in biotechnology, medicine, public health, and national security.

Anti-rabbit IgG antibodies (2 mg/mL) in sodium bicarbonate buffer (0.1 M, pH 8.3) are labeled by adding an aliquot of squaraine rotaxane N-hydroxysuccinimde ester (50 mM stock in DSMO) to a give a final concentration of 5 mg/mL, and incubating for one hour at 37° C. in the dark. Unconjugated dye is separated from the labeled protein by size-exclusion chromatography using 30,000 MW resin and sodium phosphate buffer (50 mM, pH 7.3) as eluent. The dye/protein ratio is determined spectrometrically from the molar absorptivity of 180,000 cm$^{-1}$ M$^{-1}$ for the dye at 640 nm, and 203,000 cm$^{-1}$ M$^{-1}$ for the antibody at 280 nm (this includes the contribution from attached dye).

Oligonucleotide Labeling

Fluorescent dyes are often used to covalently label oligonucleotides, especially DNA, and allow detection assays for various applications in biotechnology, medicine, public health, and national security.

Oligonucleotide (2 mg/mL) is desalted with a NAP 5 column and placed in sodium bicarbonate buffer (0.1 M, pH 8.3). Labeling is achieved by adding an aliquot of squaraine rotaxane N-hydroxysuccinimde ester (50 mM stock in DSMO) to a give a final concentration of 5 mg/mL, and incubating for one hour at 37° C. in the dark. Unconjugated dye was separated from the oligonucleotide by size-exclusion chromatography using a Sephadex 25 column followed by ethanol precipitation and the labeled and unlabeled oligonucleotides are separated by gel electrophoresis. The bands containing the labeled oligonucleotide are identified and excised. The oligonucleotide is extracted using 10 mM tris-HCl and then purified by extraction with phenol/chloroform/isoamyl alcohol, ethanol precipitation, and desalting with a NAP 5 column.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A compound having the formula:

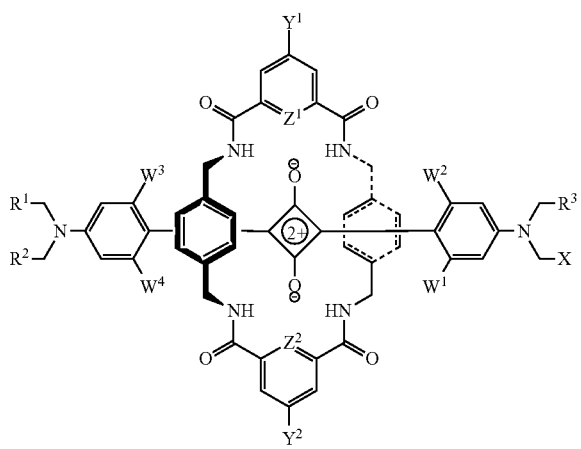

or a pharmaceutically acceptable salt thereof, wherein:

R$^1$, R$^2$, and R$^3$ are each independently alkyl, phenyl, polyethylene glycol, alkyl-phosphonate, alkyl-sulfonate, methylene-triazole-alkyl-sulfonate, methylene-triazole-alkyl-phosphonate, methylene-triazole-methylene-dimethylammonium-alkyl-sulfonate, or methylene-dimethylammonium-alkyl-phosphonate;

X=alkyl, phenyl, alkyl-carboxylic acid, alkyl ester, alkyl hydroxysuccinimde ester, alkyl maleimide, alkyl isothiocyanate, alkyl azide, alky alkyne, alkyl haloacetamido, aryl ester, aryl hydroxysuccinimde ester, aryl maleimide, aryl isothiocyanate, aryl azide, aryl alkyne, or aryl haloacetamido;

Y$^1$ and Y$^2$ are each independently H, alkoxy-triazole-methylene-sulfonate, alkoxy-triazole-methylene-dimethylammonium-alkyl-sulfonate, alkoxy-triazole-methylene-phosphonate, alkoxy-triazole-methylene-dimethylammonium-alkyl-phosphonate, triazole-methylene-sulfonate, triazole-methylene-phosphonate; triazole-methylene-dimethylammonium-alkyl-sulfonate, triazole-methylene-methylene-dimethylammonium-alkyl-phosphonate, alkyl, phenyl, alkyl-carboxylic acid, alkyl ester, alkyl hydroxysuccinimde ester, alkyl maleimide, alkyl isothiocyanate, alkyl azide, alky alkyne, alkyl haloacetamido, aryl ester, aryl hydroxysuccinimde ester, aryl maleimide, aryl isothiocyanate, aryl azide, aryl alkyne, or aryl haloacetam;

Z$^1$ and Z$^2$ are each independently CH or N; and

W$^1$, W$^2$, W$^3$, and W$^4$ are each independently H or OH, at least one of W$^1$, W$^2$, W$^3$, and W$^4$ being OH.

2. The compound of claim 1, wherein the compound has the formula:

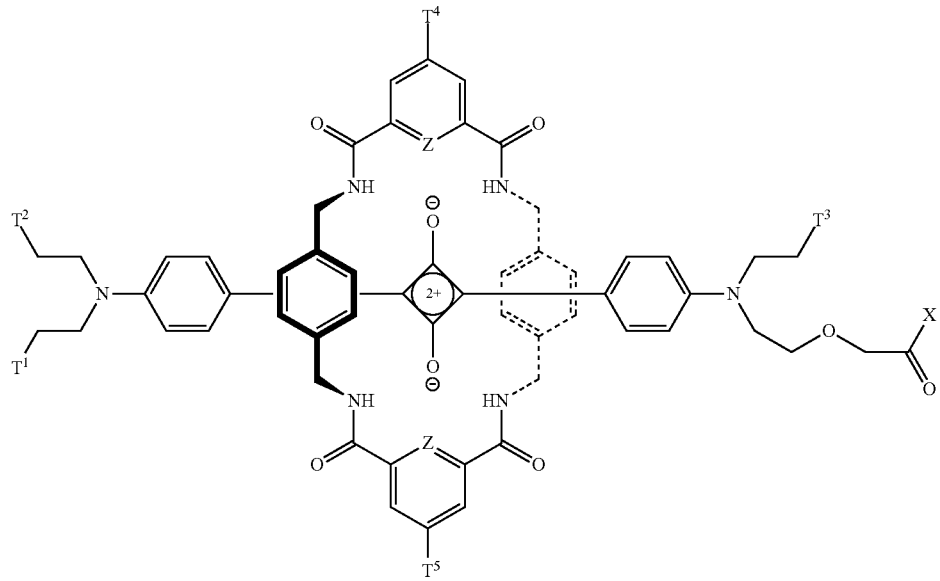

or a pharmaceutically acceptable salt thereof, wherein:

X=OH, alkoxy, aryloxy, oxy-succinimide, NH-alkyl-maleimide, or NH-polyethylene glycol-biotin;

$T^1$, $T^2$, $T^3$, $T^4$, and $T^5$ are each independently H or a 1,2,3-triazole ring that is substituted with a group R, wherein R=polyethylene glycol, methylene-dimethylammonium-alkyl-sulfonate, or methylene-dimethylammonium-alkyl-phosphonate; and Z=CH or N.

3. The compound of claim 2, wherein the compound has the formula:

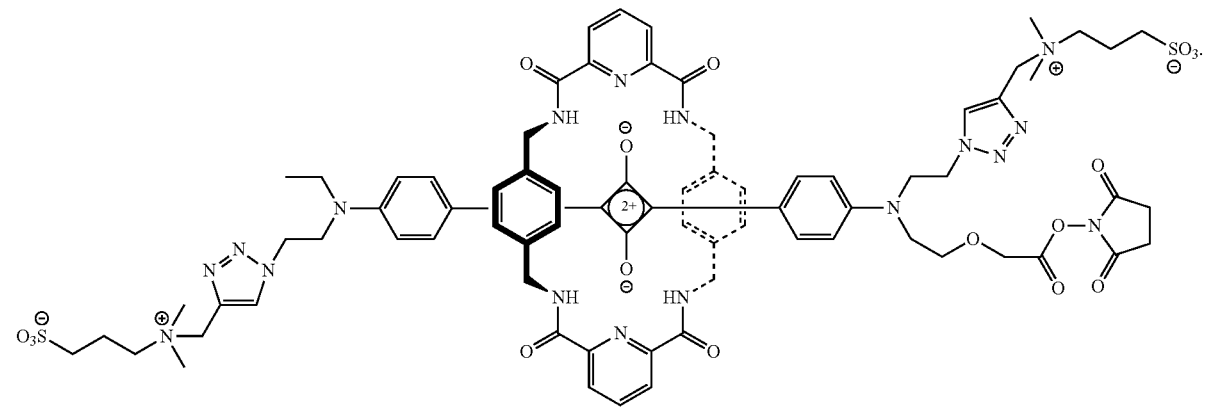

4. The compound of claim 1, wherein the compound has the formula:

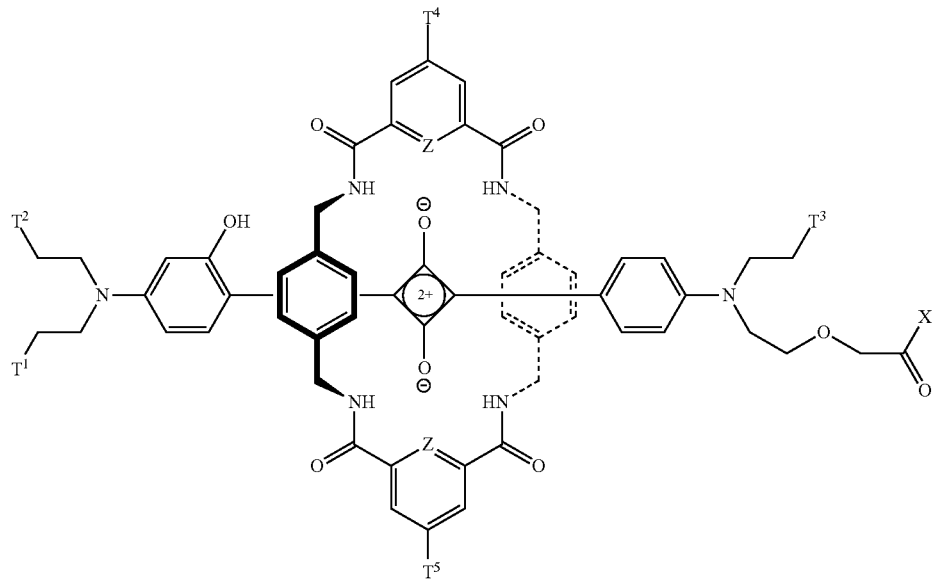

or a pharmaceutically acceptable salt thereof, wherein

X=OH, alkoxy, aryloxy, oxy-succinimide, NH-alkyl-maleimide, NH-polyethylene glycol-biotin;

$T^1$, $T^2$, $T^3$, $T^4$, and $T^5$ are each independently H or a 1,2,3-triazole ring that is substituted with a group R, wherein R=polyethylene glycol, alkyl-sulfonate, alkyl-phosphonate, methylene-dimethylammonium-alkyl-sulfonate, or methylene-dimethylammonium-alkyl-phosphonate; and Z=CH or N.

5. The compound of claim 1, wherein the compound has the formula:

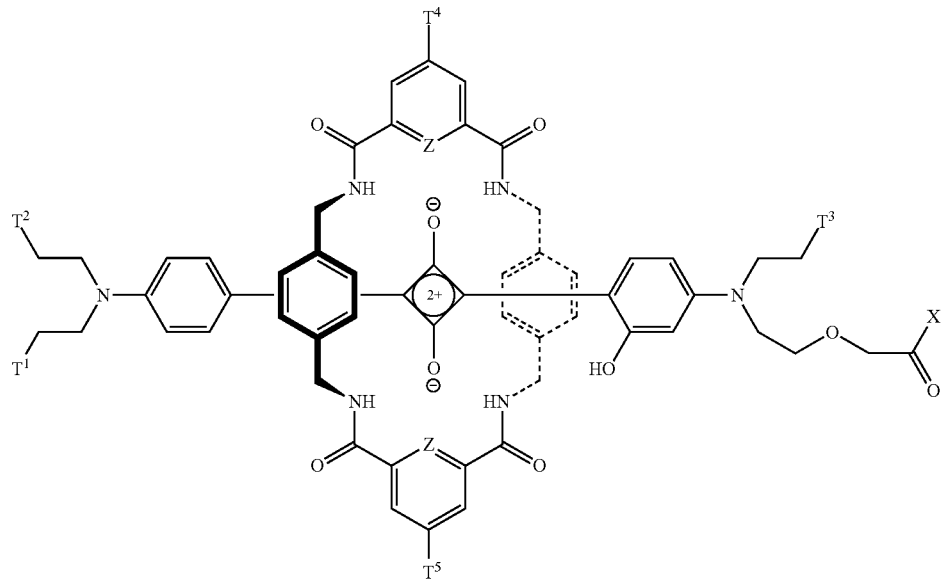

or a pharmaceutically acceptable salt thereof, wherein;
X=OH, alkoxy, aryloxy, oxy-succinimide, NH-alkyl-maleimide, or NH-polyethylene glycol-biotin;
$T^1$, $T^2$, $T^3$, $T^4$, and $T^5$ are each independently H or a 1,2,3-triazole ring that is substituted with a group R, wherein R=polyethylene glycol, alkyl-sulfonate, alkyl-phosphonate, methylene-dimethylammonium-alkyl-sulfonate, or methylene-dimethylammonium-alkyl-phosphonate; and
Z=CH or N.

6. The compound of claim 1, wherein the compound has the formula:

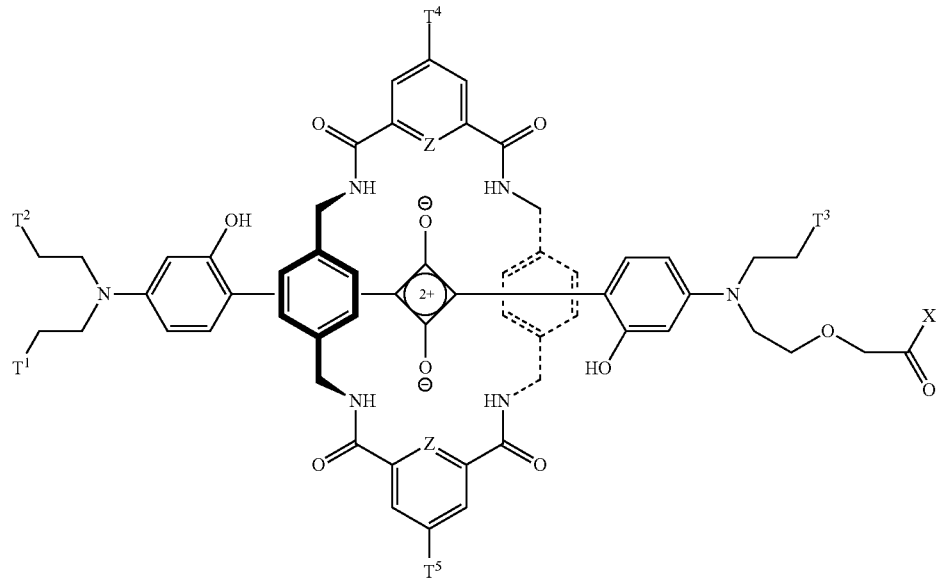

or a pharmaceutically acceptable salt thereof, wherein
X=OH, alkoxy, aryloxy, oxy-succinimide, NH-alkyl-maleimide, or NH-polyethylene glycol-biotin;
$T^1$, $T^2$, $T^3$, $T^4$, and r are each independently H or a 1,2,3-triazole ring that is substituted with a group R, wherein R=polyethylene glycol, alkyl-sulfonate, alkyl-phosphonate, methylene-dimethylammonium-alkyl-sulfonate, or methylene-dimethylammonium-alkyl-phosphonate; and
Z=CH or N.

7. The compound of claim 6, wherein the compound has the formula:

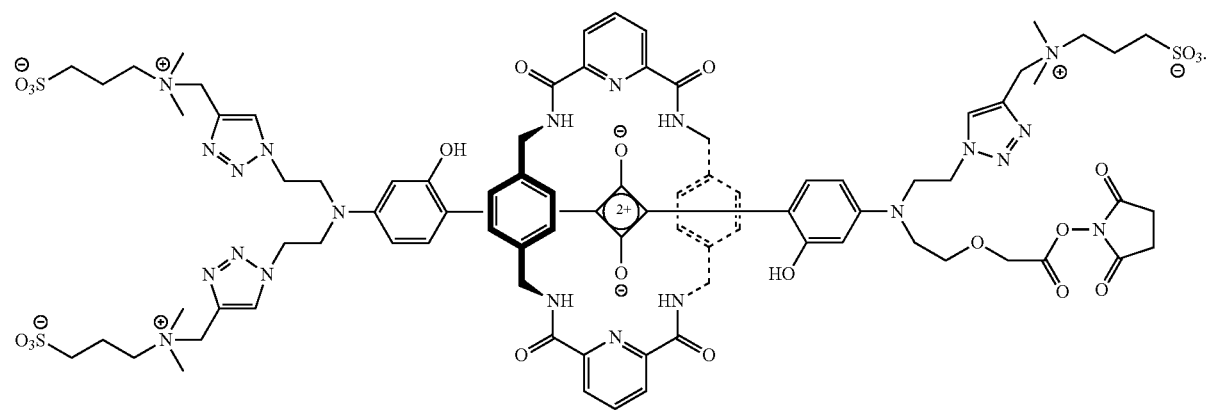

8. The compound of claim 1, wherein the compound has the formula:

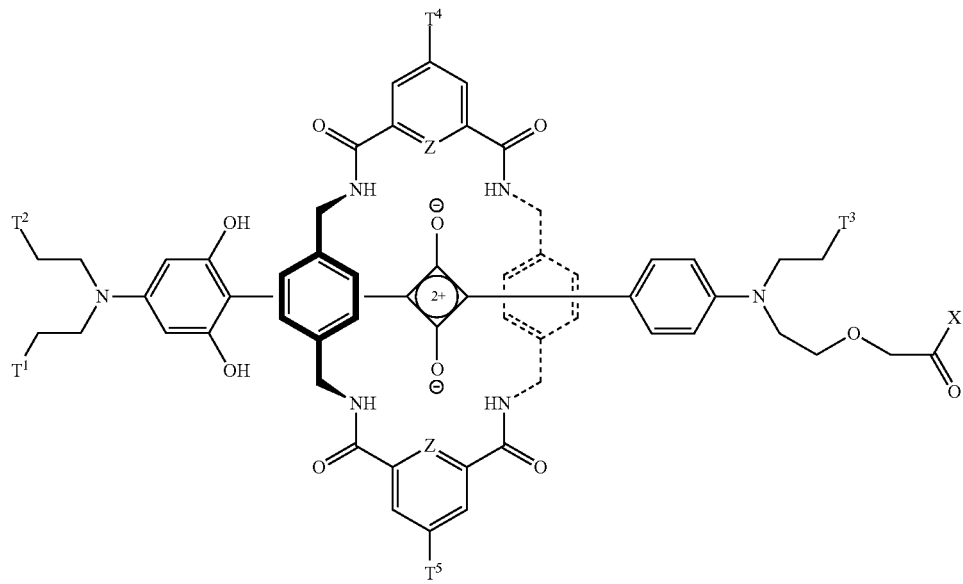

or a pharmaceutically acceptable salt thereof, wherein:

X=OH, alkoxy, aryloxy, oxy-succinimide, NH-alkyl-maleimide, or NH-polyethylene glycol-biotin;

$T^1$, $T^2$, $T^3$, $T^4$, and $T^5$ are each independently H or a 1,2,3-triazole ring that is substituted with a group R, wherein R=polyethylene glycol, alkyl-sulfonate, alkyl-phosphonate, methylene-dimethylammonium-alkyl-sulfonate, or methylene-dimethylammonium-alkyl-phosphonate; and Z=CH or N.

9. The compound of claim 1, wherein the compound has the formula:

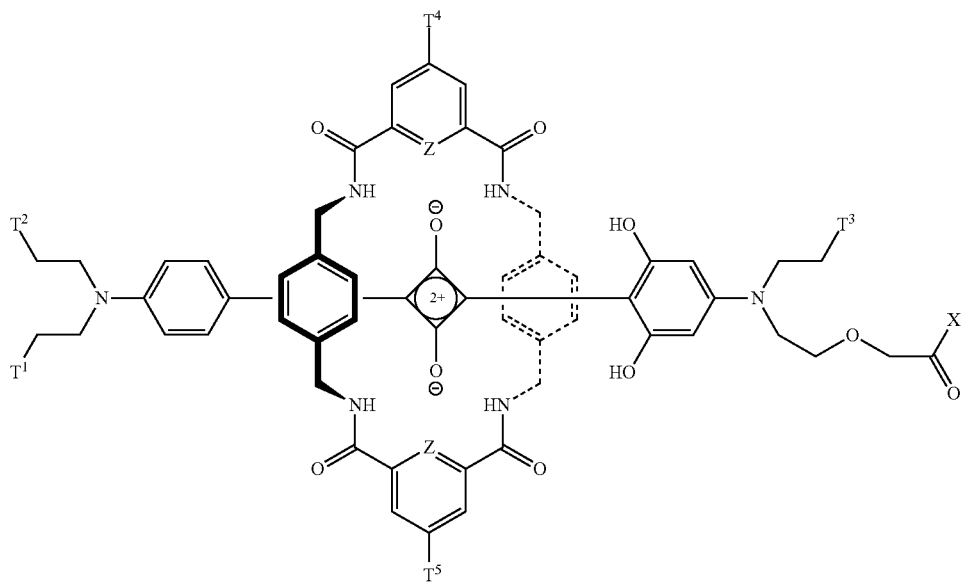

or a pharmaceutically acceptable salt thereof, wherein:

X=OH, alkoxy, aryloxy, oxy-succinimide, NH-alkyl-maleimide, or NH-polyethylene glycol-biotin;

$T^1$, $T^2$, $T^3$, $T^4$, and $T^5$ are each independently H or a 1,2,3-triazole ring that is substituted with a group R, wherein R=polyethylene glycol, alkyl-sulfonate, alkyl-phosphonate, methylene-dimethylammonium-alkyl-sulfonate, or methylene-dimethylammonium-alkyl-phosphonate; and Z=CH or N.

10. A compound having the formula:

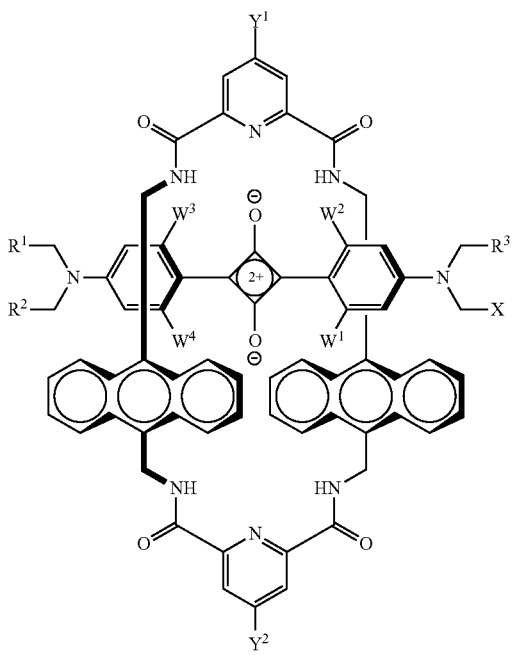

or a pharmaceutically acceptable salt thereof, wherein:

$R^1$, $R^2$, and $R^3$ are each independently alkyl, phenyl, polyethylene glycol, alkyl-phosphonate, alkyl-sulfonate, methylene-triazole-alkyl-sulfonate, methylene-triazole-alkyl-phosphonate, methylene-triazole-methylene-dimethylammonium-alkyl-sulfonate, or methylene-dimethylammonium-alkyl-phosphonate;

X=alkyl, phenyl, alkyl-carboxylic acid, alkyl ester, alkyl hydroxysuccinimde ester, alkyl maleimide, alkyl isothiocyanate, alkyl azide, alky alkyne, alkyl haloacetamido, aryl ester, aryl hydroxysuccinimde ester, aryl maleimide, aryl isothiocyanate, aryl azide, aryl alkyne, or aryl haloacetamido;

$Y^1$ and $Y^2$ are each independently H, alkoxy-triazole-methylene-sulfonate, alkoxy-triazole-methylene-dimethylammonium-alkyl-sulfonate, alkoxy-triazole-methylene-phosphonate, alkoxy-triazole-methylene-dimethylammonium-alkyl-phosphonate, triazole-methylene-sulfonate, triazole-methylene-phosphonate, triazole-methylene-dimethylammonium-alkyl-sulfonate, triazole-methylene-methylene-dimethylammonium-alkyl-phosphonate, alkyl, phenyl, alkyl-carboxylic acid, alkyl ester, alkyl hydroxysuccinimde ester, alkyl maleimide, alkyl isothiocyanate, alkyl azide, alkyl alkyne, alkyl haloacetamido, aryl ester, aryl hydroxysuccinimde ester, aryl maleimide, aryl isothiocyanate, aryl azide, aryl alkyne, or aryl haloacetamido; and $W^1$, $W^2$, $W^3$, and $W^4$ are each independently H or OH, at least one of $W^1$, $W^2$, $W^3$, and $W^4$ being OH.

11. The compound of claim 10, wherein the compound has the formula:

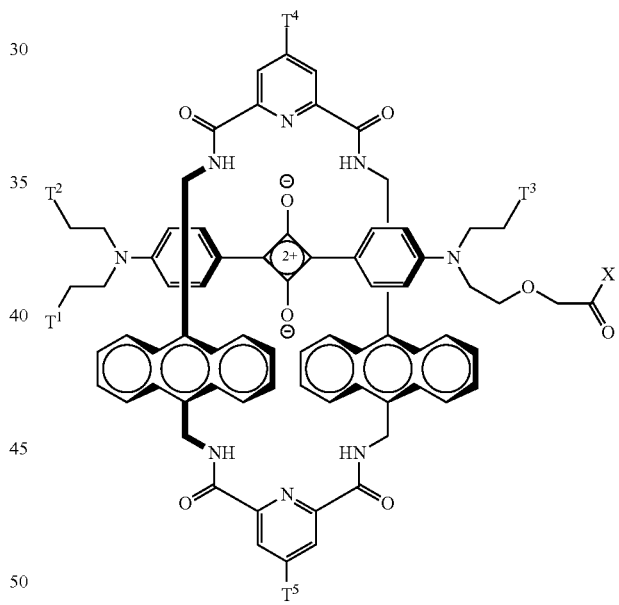

or a pharmaceutically acceptable salt thereof, wherein:

X=OH, alkoxy, aryloxy, oxy-succinimide, NH-alkyl-maleimide, or NH-polyethylene glycol-biotin; and $T^1$, $T^2$, $T^3$, $T^4$, and $T^5$ are each independently H or a 1,2,3-triazole ring that is substituted with a group R, wherein R=polyethylene glycol, methylene-dimethylammonium-alkyl-sulfonate, or methylene-dimethylammonium-alkyl-phosphonate.

12. The compound of claim 10, wherein the compound has the formula:
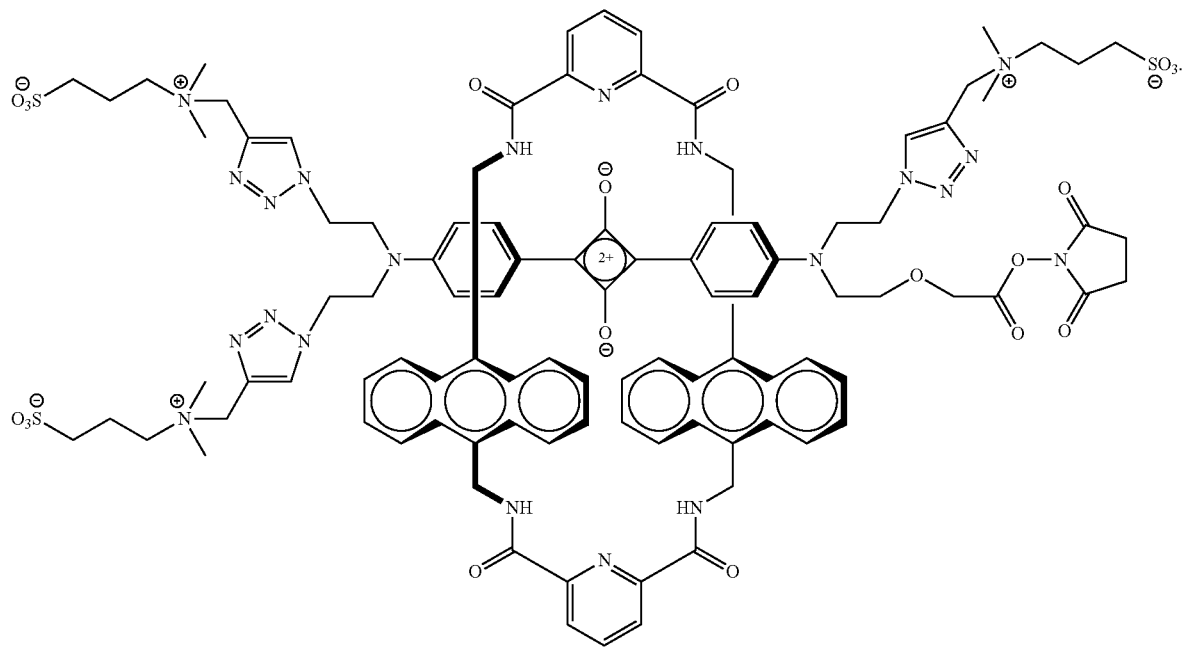
13. The compound of claim 10, wherein the compound has the formula:
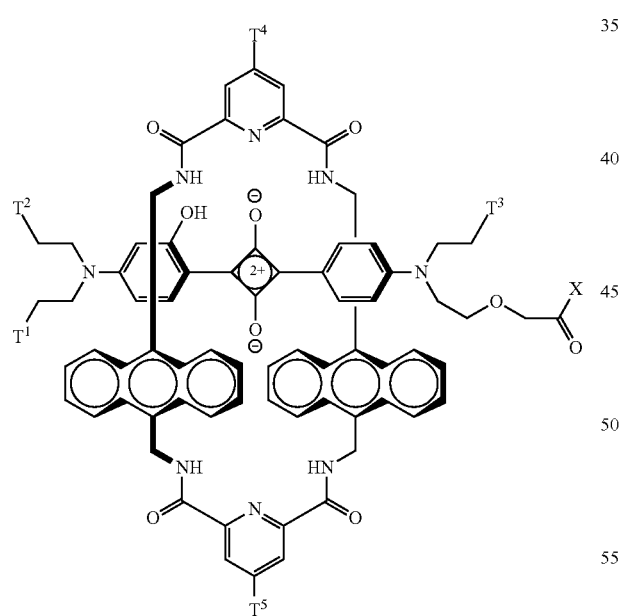

or a pharmaceutically acceptable salt thereof, wherein:
X=OH, alkoxy, aryloxy, oxy-succinimide, NH-alkyl-maleimide, or NH-polyethylene glycol-biotin; and
$T^1$, $T^2$, $T^3$, $T^4$, and $T^5$ are each independently H or a 1,2,3-triazole ring that is substituted with a group R, wherein R=polyethylene glycol, alkyl-sulfonate, alkyl-phosphonate, methylene-dimethylammonium-alkyl-sulfonate, or methylene-dimethylammonium-alkyl-phosphonate.

14. The compound of claim 13, wherein the compound has the formula:

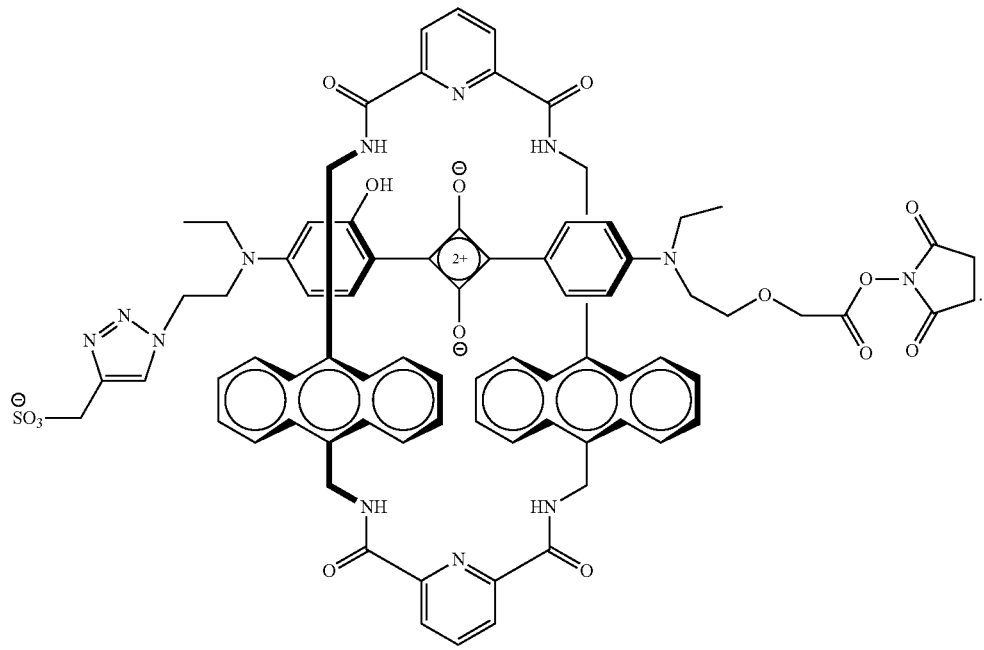

15. The compound of claim 10, wherein the compound has the formula:

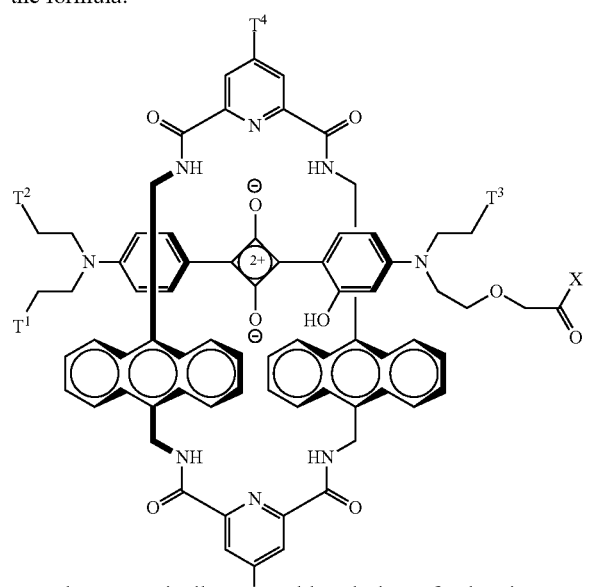

or a pharmaceutically acceptable salt thereof, wherein:
X=OH, alkoxy, aryloxy, oxy-succinimide, NH-alkyl-maleimide, or NH-polyethylene glycol-biotin; and
$T^1$, $T^2$, $T^3$, $T^4$, and $T^5$ are each independently H or a 1,2,3-triazole ring that is substituted with a group R, wherein R=polyethylene glycol, alkyl-sulfonate, alkyl-phosphonate, methylene-dimethylammonium-alkyl-sulfonate, or methylene-dimethylammonium-alkyl-phosphonate.

16. The compound of claim 10, wherein the compound has the formula:

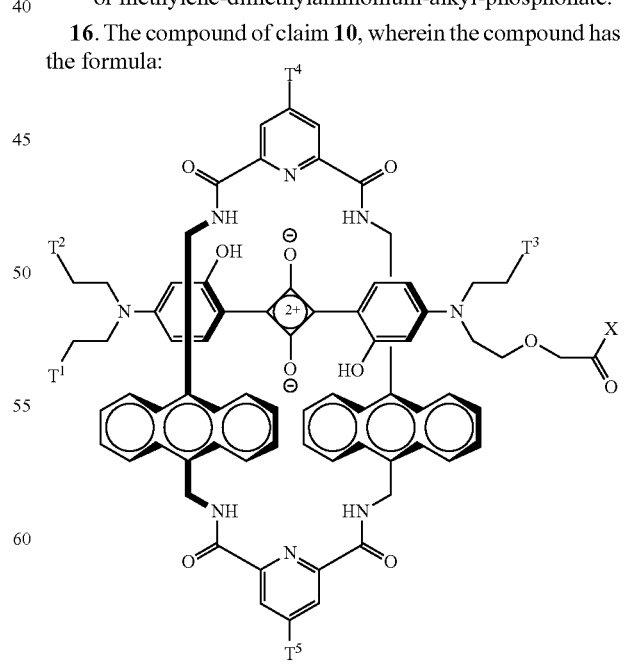

or a pharmaceutically acceptable salt thereof, wherein:

X=OH, alkoxy, aryloxy, oxy-succinimide, NH-alkyl-maleimide, or NH-polyethylene glycol-biotin; and $T^1$, $T^2$, $T^3$, $T^4$, and $T^5$ are each independently H or a 1,2,3-triazole ring that is substituted with a group R, wherein R=polyethylene glycol, alkyl-sulfonate, alkyl-phosphonate, methylene-dimethylammonium-alkyl-sulfonate, or methylene-dimethylammonium-alkyl-phosphonate.

17. The compound of claim 10, wherein the compound has the formula:

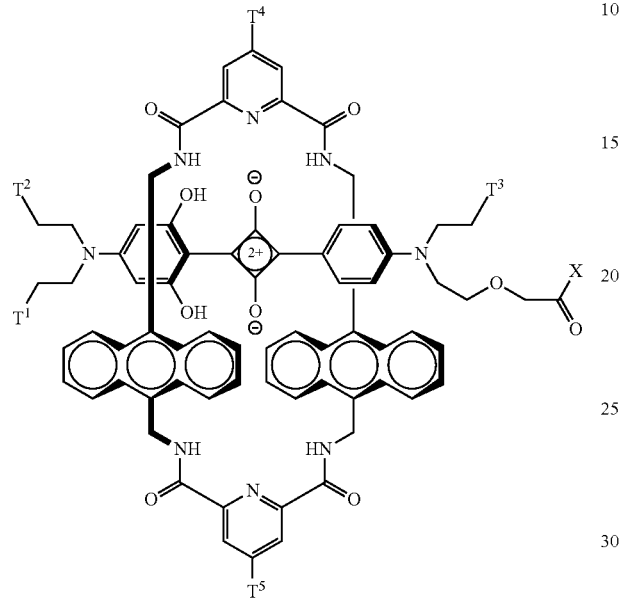

or a pharmaceutically acceptable salt thereof, wherein:
X=OH, alkoxy, aryloxy, oxy-succinimide, NH-alkyl-maleimide, or NH-polyethylene glycol-biotin; and $T^1$, $T^2$, $T^3$, $T^4$, and $T^5$ are each independently H or a 1,2,3-triazole ring that is substituted with a group R, wherein R=polyethylene glycol, alkyl-sulfonate, or alkyl-phosphonate.

18. The compound of claim 10, wherein the compound has the formula:

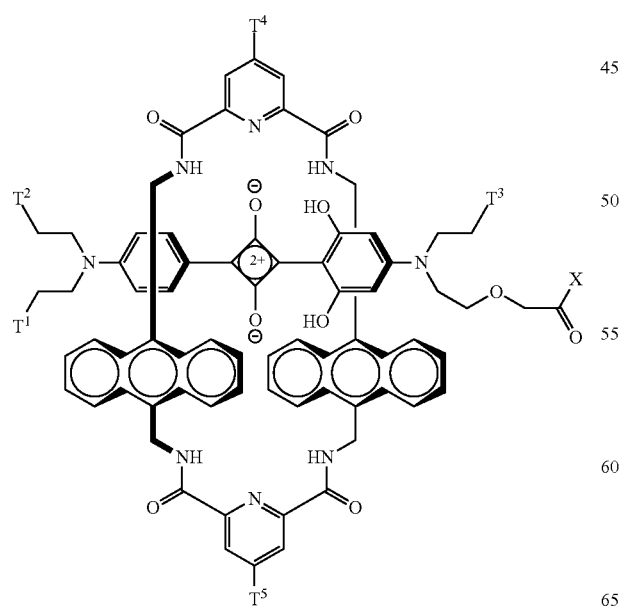

or a pharmaceutically acceptable salt thereof, wherein:
X=OH, alkoxy, aryloxy, oxy-succinimide, NH-alkyl-maleimide, or NH-polyethylene glycol-biotin;

$T^1$, $T^2$, $T^3$, $T^4$, and $T^5$ are each independently H or a 1,2,3-triazole ring that is substituted with a group R, wherein R=polyethylene glycol, alkyl-sulfonate, or alkyl-phosphonate.

19. A compound having the formula:

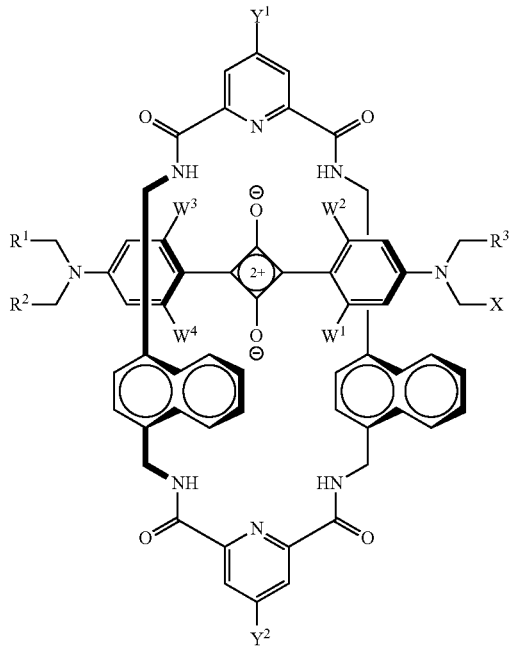

or a pharmaceutically acceptable salt thereof, wherein:
$R^1$, $R^2$, and $R^3$ are each independently alkyl, phenyl, polyethylene glycol, alkyl-phosphonate, alkyl-sulfonate, methylene-triazole-alkyl-sulfonate, or methylene-triazole-alkyl-phosphonate, methylene-triazole-methylene-dimethylammonium-alkyl-sulfonate, or methylene-dimethylammonium-alkyl-phosphonate;

X=alkyl, phenyl, alkyl-carboxylic acid, alkyl ester, alkyl hydroxysuccinimde ester, alkyl maleimide, alkyl isothiocyanate, alkyl azide, alky alkyne, alkyl haloacetamido, aryl ester, aryl hydroxysuccinimde ester, aryl maleimide, aryl isothiocyanate, aryl azide, aryl alkyne, or aryl haloacetamido;

$Y^1$ and $Y^2$ are each independently H, alkoxy-triazole-methylene-sulfonate, alkoxy-triazole-methylene-dimethylammonium-alkyl-sulfonate, alkoxy-triazole-methylene-phosphonate, alkoxy-triazole-methylene-dimethylammonium-alkyl-phosphonate, triazole-methylene-sulfonate, triazole-methylene-phosphonate; triazole-methylene-dimethylammonium-alkyl-sulfonate, triazole-methylene-methylene-dimethylammonium-alkyl-phosphoriate, alkyl, phenyl, alkyl-carboxylic acid, alkyl ester, alkyl hydroxysuccinimde ester, alkyl maleimide, alkyl isothiocyanate, alkyl azide, alky alkyne, alkyl haloacetamido, aryl ester, aryl hydroxysuccinimde ester, aryl maleimide, aryl isothiocyanate, aryl azide, aryl alkyne, or aryl haloacetamido; and $W^1$, $W^2$, $W^3$, and $W^4$ are each independently H or OH.

* * * * *